US008293929B2

(12) United States Patent
Tanoury et al.

(10) Patent No.: US 8,293,929 B2
(45) Date of Patent: Oct. 23, 2012

(54) PROCESSES AND INTERMEDIATES

(75) Inventors: Gerald J. Tanoury, Hudson, MA (US);
Minzhang Chen, Acton, MA (US);
Andrew D. Jones, Needham, MA (US);
Philip L. Nyce, Milbury, MA (US);
Martin Trudeau, Shannon, CA (US);
David J. Guerin, Natick, MA (US);
John R. Snoonian, Bolton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/902,811

(22) Filed: Oct. 12, 2010

(65) Prior Publication Data

US 2011/0071298 A1    Mar. 24, 2011

Related U.S. Application Data

(62) Division of application No. 12/074,983, filed on Mar. 7, 2008, now Pat. No. 7,834,200, which is a division of application No. 11/078,147, filed on Mar. 11, 2005, now Pat. No. 7,381,827.

(60) Provisional application No. 60/552,480, filed on Mar. 12, 2004.

(51) Int. Cl.
*C07D 307/02*      (2006.01)
*C07C 205/00*      (2006.01)
*C07C 233/00*      (2006.01)

(52) U.S. Cl. .................. 549/505; 548/950; 564/189

(58) Field of Classification Search .................. None
See application file for complete search history.

(56) References Cited

U.S. PATENT DOCUMENTS

| | | | |
|---|---|---|---|
| 5,656,627 A | 8/1997 | Bemis et al. | |
| 5,716,929 A | 2/1998 | Bemis et al. | |
| 5,756,466 A | 5/1998 | Bemis et al. | |
| 5,817,848 A | 10/1998 | Kamer et al. | |
| 5,843,904 A | 12/1998 | Bemis et al. | |
| 5,847,135 A | 12/1998 | Bemis et al. | |
| 5,874,424 A | 2/1999 | Batchelor et al. | |
| 5,919,790 A | 7/1999 | Allen et al. | |
| 6,184,210 B1 | 2/2001 | Keana et al. | |
| 6,184,244 B1 | 2/2001 | Karanewsky et al. | |
| 6,187,771 B1 | 2/2001 | Karanewsky et al. | |
| 6,197,750 B1 | 3/2001 | Karanewsky et al. | |
| 6,204,261 B1 | 3/2001 | Batchelor et al. | |
| 6,225,288 B1 | 5/2001 | Han et al. | |
| 6,235,899 B1 | 5/2001 | Bouchet et al. | |
| 6,242,422 B1 | 6/2001 | Karanewsky et al. | |
| 6,265,380 B1 | 7/2001 | Tung et al. | |
| 6,268,207 B1 | 7/2001 | Bailey | |
| 6,316,415 B1 | 11/2001 | Albrecht et al. | |
| 6,323,180 B1 | 11/2001 | Llinas-brunet et al. | |
| 6,329,379 B1 | 12/2001 | Llinas-brunet et al. | |
| 6,329,417 B1 | 12/2001 | Llinas-brunet et al. | |
| 6,410,531 B1 | 6/2002 | Llinas-brunet et al. | |
| 6,420,380 B2 | 7/2002 | Llinas-brunet et al. | |
| 6,420,522 B1 | 7/2002 | Bemis et al. | |
| 6,423,840 B1 | 7/2002 | Batchelor et al. | |
| 6,495,522 B1 | 12/2002 | Wang et al. | |
| 6,531,474 B1 | 3/2003 | Wannamaker et al. | |
| 6,534,523 B1 | 3/2003 | Llinas-burnet et al. | |
| 6,617,309 B2 | 9/2003 | Tung et al. | |
| 6,620,782 B1 | 9/2003 | Cai et al. | |
| 6,632,962 B2 | 10/2003 | Golec et al. | |
| 6,689,784 B2 | 2/2004 | Bebbington et al. | |
| 6,699,856 B2 | 3/2004 | Han et al. | |
| 6,716,818 B2 | 4/2004 | Cai et al. | |
| 6,800,619 B2 | 10/2004 | Charrier et al. | |
| 6,844,363 B2 | 1/2005 | Murakami et al. | |
| 6,846,806 B2 | 1/2005 | Priestley | |
| 6,909,000 B2 | 6/2005 | Farmer et al. | |
| 6,939,854 B2 | 9/2005 | Priestley | |
| 7,109,357 B2 * | 9/2006 | Wannamaker et al. ....... 549/313 |
| 2002/0013278 A1 | 1/2002 | Wannamaker et al. | |
| 2002/0016321 A1 | 2/2002 | Karanewsky et al. | |
| 2002/0045623 A1 | 4/2002 | Charrier et al. | |
| 2002/0061853 A1 | 5/2002 | Golec | |
| 2002/0147171 A1 | 10/2002 | Fritz et al. | |
| 2002/0169177 A1 | 11/2002 | Kay et al. | |
| 2003/0092703 A1 | 5/2003 | Mortimore et al. | |
| 2003/0096737 A1 | 5/2003 | Diu-Hercend et al. | |
| 2003/0119748 A1 | 6/2003 | Karanewsky et al. | |
| 2003/0119899 A1 | 6/2003 | Wannamaker et al. | |
| 2003/0162993 A1 | 8/2003 | Mortimore et al. | |
| 2003/0236242 A1 | 12/2003 | Perni et al. | |
| 2004/0009966 A1 | 1/2004 | Wos et al. | |

(Continued)

FOREIGN PATENT DOCUMENTS

WO        WO93/09135        5/1993

(Continued)

OTHER PUBLICATIONS

"Crystallization and Precipitation" in Ullmann's Encyclopedia of Industrial Chemistry, Published Online: Jan. 15, 2003, Copyright © 2002 by Wiley-VCH Verlag GmbH & Co. KGaA.*
"Chromatography" in Kirk-Othmer Encyclopedia of Chemical Technology, Published Online: Jan. 25, 2002, Copyright John Wiley & Sons, Inc.*
Brown, J.M., et al., Red. Tray. Chim. Pays-Bas, vol. 114, 1995, pp. 242-251.
Burk, M.J., et al., J. Amer. Chem. Soc., vol. 115, 1993, pp. 10125-10138.
Burk, M.J., et al., J. Amer. Chem. Soc., vol. 120, 1998, pp. 657-663.
C. Escobar, et al., Ann. Quim. (1971), 67,43-57.
Chapman, Bioorg. Med. Chem. Lett. 1992, 2(6), 613.
Dolle, et al., J. Med. Chem., 40, 1941 (1997).
Ellis, et al., Ann. Rev. Cell. Biol., 1991, 7, 663.
Feringa, Ben L., et al., "Asymmetric 1,4-additions to 5-alkoxy-2(5H)-furanones. An Efficient synthesis of (R)- and (S)-3,4-epoxy-l-butanol," Tetrahedron, vol. 44, No. 23, 1988, pp. 7213-7222.

(Continued)

*Primary Examiner* — Karl J Puttlitz
(74) *Attorney, Agent, or Firm* — Honigman Miller Schwartz and Cohn LLP; Heidi M. Berven; Jonathan P. O'Brien

(57) ABSTRACT

The invention relates to processes and compounds useful for producing modified aspartic acid derivatives, such as aspartic acid aldehyde moieties. Aspartic acid derivatives are useful for preparing caspase inhibitors and/or prodrugs thereof.

6 Claims, No Drawings

U.S. PATENT DOCUMENTS

| | | |
|---|---|---|
| 2004/0014753 A1 | 1/2004 | O'Neil et al. |
| 2004/0019017 A1 | 1/2004 | Mortimore et al. |
| 2004/0048797 A1 | 3/2004 | Miller et al. |
| 2004/0072850 A1 | 4/2004 | Knegtel et al. |
| 2004/0142876 A1 | 7/2004 | Colarusso et al. |
| 2004/0192612 A1 | 9/2004 | Charrier et al. |
| 2004/0242494 A1 | 12/2004 | Brenchley et al. |
| 2004/0254117 A9 | 12/2004 | Saksena et al. |

FOREIGN PATENT DOCUMENTS

| | | |
|---|---|---|
| WO | WO99/36426 | 1/1998 |
| WO | WO98/16502 | 4/1998 |
| WO | WO99/47545 | 11/1999 |
| WO | WO01/42216 | 6/2001 |
| WO | WO01/81330 | 11/2001 |

OTHER PUBLICATIONS

Jiang, L., et al., "Copper-catalyzed coupling of amides and carbamates with vinyl halides," Organic Letters, vol. 5, No. 20, 2003, pp. 3667-3669.

Matteoli, U., et al., J. Molecular Catalysis A: Chemical, vol. 140, 1999, pp. 131-137.

Saburi, M., et al., Tetrahedron Lett. vol. 33, 1992, pp. 5783-5786.

Thornberry, Chem. Biol. ., 1998, 5, R97-R103.

Wallace, D. J., et al. "Palladium-catalyzed amidation of enol triflates: a new synthesis of enamides," Organic Letters, vol. 5, No. 24, 2003, pp. 4749-4752.

Zhu, G., et al., J. Org. Chem., vol. 64, 1999, pp. 6907-6910.

* cited by examiner

PROCESSES AND INTERMEDIATES

CLAIM OF PRIORITY

The present application is a divisional application of and claims priority to U.S. application Ser. No. 12/074,983 filed Mar. 7, 2008, to application Ser. No. 11/078,147 filed on Mar. 11, 2005, and to U.S. Application 60/552,480 filed on Mar. 12, 2004, the entire contents of which are hereby incorporated by reference.

FIELD OF THE INVENTION

This invention relates to processes for preparing caspase inhibitors and intermediates derivatives thereof.

BACKGROUND OF THE INVENTION

Caspases are a family of cysteine protease enzymes that are key mediators in the signaling pathways for apoptosis and cell disassembly (Thornberry, *Chem. Biol.*, 1998, 5, R97-R103). Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, and certain neurodegenerative disorders (see generally *Science*, 1998, 281, 1283-1312; Ellis et al., *Ann. Rev. Cell. Biol.*, 1991, 7, 663). Caspase-1, the first identified caspase, is also known as interleukin-1β converting enzyme or "ICE." Caspase-1 converts precursor interleukin-1β ("pIL-1β") to the pro-inflammatory active form by specific cleavage of pIL-1β between Asp-116 and Ala-117. Besides caspase-1 there are also eleven other known human caspases which have been classified into families based on their biological function.

A number of useful caspase inhibitors have been reported that contain an aspartic acid aldehyde moiety, which will exist in equilibrium with its cyclic hemiacetal form as shown below:

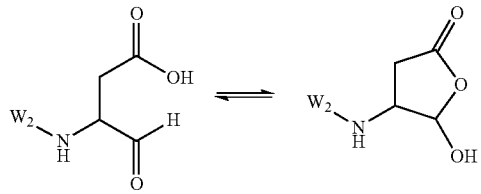

where $W_2$ represents the rest of the caspase inhibitor molecule. Based on the hemiacetal, orally available prodrugs of these inhibitors have been developed having the acetal structure 1, including the compound 2 in which $R_1$ is alkyl. The ICE inhibitor 2 is a prodrug being developed as a treatment for rheumatoid arthritis (see U.S. Pat. No. 5,716,929).

1

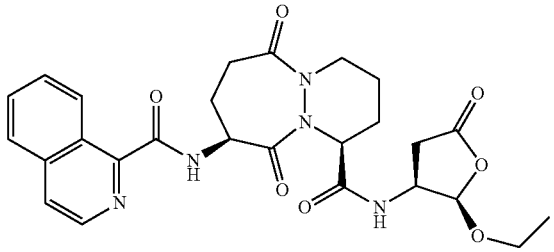

Processes for the preparation of a peptidic caspase inhibitor prodrug of formula 1 have been reported (see, e.g., *Bioorg. Med. Chem. Lett.* 1992, 2(6), 613 and WO 99/03852. However, reported routes have disadvantages, especially for preparing chiral compounds. For example, the routes require expensive starting materials, chromatographic separation of diastereomers, and/or disadvantageous synthetic steps.

It would be desirable to have a synthetic route to aspartic acetal caspase inhibitors, or prodrugs thereof, that is amenable to large-scale synthesis and overcomes the aforementioned shortcomings or otherwise improves upon the current methods.

SUMMARY OF THE INVENTION

In general, the invention relates to processes and compounds useful for producing modified aspartic acid derivatives, such as aspartic acid aldehyde moieties. Aspartic acid derivatives are useful for preparing caspase inhibitors and/or prodrugs thereof.

In one aspect, the invention features a process for preparing a compound of formula GIA or GIB:

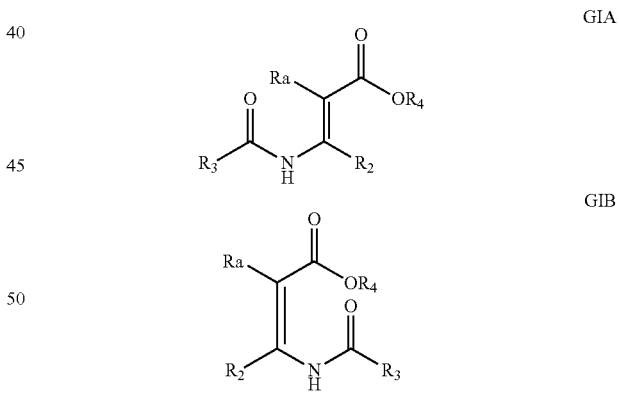

comprising the steps of:
(a) reacting a compound of formula GIIA or GIIB:

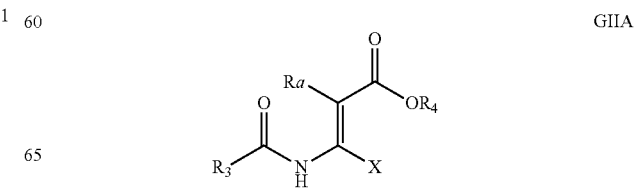

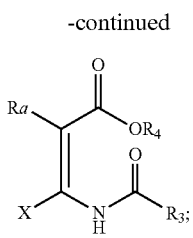

and a compound of formula GIII:

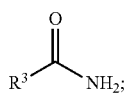

in the presence of a palladium catalyst, a palladium ligand, and a base in a solvent optionally including a phase transfer catalyst and optionally including water;
wherein:
X is a leaving group;
$R_a$ is H, an optionally substituted alkyl, an optionally substituted aryl, —CN, —C(O)—Oalkyl or halogen;
$R^3$ is an organic moiety;
$R^2$ is an optionally substituted alkyl, heterocyclic, alkylaryl, or aryl; and
$R^4$ is an optionally substituted aliphatic, a heterocyclic, or an aromatic; or
$R^2$ and $R^4$ together with the groups to which they are bound, form a 5- to 8-membered heterocyclic ring which is optionally substituted. Embodiments of this aspect may include using a phase transfer catalyst.

Other aspects of the invention are set forth herein.

DESCRIPTION OF THE INVENTION

I. Definitions

As used herein, the base used in connection with palladium catalyst and palladium ligand refers to an "inorganic base" or an "organic base".

As used herein, "inorganic bases" that may be used in a process of this invention include, but are not limited to a carbonate salt, a bicarbonate salt, and/or a phosphate salt (and mixtures thereof). In some embodiments of this invention, the inorganic base may be a carbonate salt having the formula $MCO_3$, wherein M is an appropriate counter-cation. Examples of carbonate salts include, but are not limited to, $K_2CO_3$, $K_2PO_4$, $Na_2CO_3$, $Li_2CO_3$, $Rb_2CO_3$, and $Cs_2CO_3$. In some specific embodiments, the inorganic base is $K_2CO_3$ or $Cs_2CO_3$.

As used herein, "organic bases" that may be used in a process of this invention include tertiary organic bases that include, but are not limited to trialkylamines, e.g. diethylisopropylamine, triethylamine, N-methylmorpholine and the like, and heteroaryl amines, e.g. pyridine, quinoline, and the like.

As used herein, "Palladium catalysts" that may be used in a process of this invention include, but are not limited to, Palladium II Salts such as $Pd(OAc)_2$ and $Pd_2 dba_3$.

As used herein, "Palladium ligand" and "Palladium II Ligand" refers to a ligand that is capable of forming a complex with the palladium catalyst. Palladium ligands include, but are not limited to, phosphine, bisphosphine, XantPhos, bis(diphenylphosphino)ferrocene and DPEPhos (see Aldrich catalog). See also, WO 95/30680 and U.S. Pat. No. 5,817,848.

"Solvents" for use in this invention include, but are not limited to, toluene, dioxane, and THF, and mixtures thereof.

The term "leaving group" refers to a moiety which is replaced by $R_3CONH_2$. Specific groups include, but are not limited to, chloro, bromo, iodo, pseudohalogens, triflate, tosylate, mesylate, and nosylate.

The term "organic moiety" as used in defining variable $R^3$ refers to any chemical moiety provided that the moiety does not contain a moiety that would interfere with the palladium catalysts. Such interfering moieties would be well known to skilled practitioners and include, e.g., a free sulfhydryl group. A group such as a sulfide or a thiol should not therefore be present in the $R^3$ organic moiety. Furthermore, the $R^3$ organic moiety should not contain an amine group, such as a primary or secondary amine that would be more reactive than the amide of formula (GIIA or GIIB). $R^3$ may contain primary and secondary amines that are capped with protecting groups that reduce the interaction between the protected amine and the palladium catalysts.

As used herein, the term "phase transfer catalyst" means a compound which is capable of transferring a water soluble anion into an organic phase. Phase transfer catalysts include tetralkylammonium salts, phosphonium salts and crown ethers. Examples of phase transfer catalysts include, but are not limited to tetrasubstituted ammonium salts and trisubstituted amines which may form tetrasubstituted ammonium salts in situ. Tetrasubstituted ammonium salts include, but are not limited to, tetrabutylammonium, benzyltrimethylammonium, tetraethylammonium, cetyltrimethylammonium salts in which the counter ion can be salts bromide, chloride, or iodide. In some examples, the phase transfer catalyst is cetyltrimethylammonium bromide. Trisubstituted amines include, but are not limited to triethylamine, tributylamine, benzyldiethylamine, and diisopropylethylamine.

As used herein, the terms "lactone" and "furanone" may be used interchangeably as will be understood by one skilled in the art.

As used herein, the term "aliphatic" means straight chained, branched or cyclic $C_1$-$C_{12}$ hydrocarbons which are completely saturated or which contain one or more units of unsaturation. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl.

The term "alkyl" and "alkoxy" used alone or as part of a larger moiety refers to both straight and branched chains containing one to twelve carbon atoms. The terms "alkenyl" and "alkynyl" used alone or as part of a larger moiety shall include both straight and branched chains containing two to twelve carbon atoms.

As used herein, the term "aryl", used alone or as part of a larger moiety as in "aralkyl", refers to aromatic ring groups having five to fourteen members, such as phenyl, benzyl, 1-naphthyl, 2-naphthyl, 1-anthracyl and 2-anthracyl, and heterocyclic aromatic groups or heteroaryl groups such as 2-furanyl, 3-furanyl, N-imidazolyl, 2-imidazolyl, 4-imidazolyl, 5-imidazolyl, 3-isoxazolyl, 4-isoxazolyl, 5-isoxazolyl, a 1,3,4-oxadiazolyl, a 1,2,4-oxadiazolyl, 2-oxadiazolyl, 5-oxadiazolyl, 2-oxazolyl, 4-oxazolyl, 5-oxazolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiadiazolyl, 5-thiadiazolyl, 2-thiazolyl, 4-thiazolyl, 5-thiazolyl, 5-tetrazolyl, 2-triazolyl, 5-triazolyl, 2-thienyl, or 3-thienyl. The term "aryl ring" also refers to rings that are optionally substituted. Aryl groups also include fused polycyclic aromatic ring systems in which a carbocyclic aromatic ring or heteroaryl ring is fused to one or more other rings. Examples include tetrahydronaphthyl, benzimidazolyl, benzothienyl, benzofuranyl, indolyl, quinolinyl, benzothiazolyl, benzooxazolyl, benzimidazolyl, isoquinolinyl, isoindolyl, acridinyl, benzoisoxazolyl, and the like. Also included within the scope of the term "aryl", as it is used herein, is a group in which one or more carbocyclic aromatic rings and/or heteroaryl rings are fused to a cycloalkyl or non-aromatic heterocyclic ring, for example, indanyl or tetrahydrobenzopyranyl. The term "aromatic ring" or "aromatic group" refers to aryl groups.

The term "heterocyclic" refers to saturated and partially unsaturated monocyclic or polycyclic ring systems containing one or more heteroatoms and a ring size of three to eight such as piperidinyl, piperazinyl, tetrahydrofuranyl, pyrrolidinyl, tetrahydropyranyl, morpholinyl, and the like.

As used herein, the term "bicyclic fused ring system" or "bicyclic ring system" refers to two rings which share two atoms. Either ring may be saturated, partially unsaturated, or aromatic. Each ring also may contain 1 to 3 heteroatoms. Examples of bicyclic fused ring systems include, but are not limited to, compounds g, j, k, l, and m shown in Table 1, and compounds g-1 and j-1, l-1, l-2, k-1, m-1 and m-2 shown in Table 2.

As used herein, the term "tricyclic fused ring system" or "tricyclic ring system" refers to a bicyclic ring system in which a third ring is fused to the bicyclic ring system such that the third ring shares at least two atoms with the bicyclic ring system. In some embodiments, all three rings share at least one common atom. Any of the rings in the tricyclic ring system may be saturated, particlly unsaturated, or aromatic. Each of the rings may include 1 to 3 heteroatoms. Examples of tricyclic ring systems include, but are not limited to, compounds e and q shown in Table 1, and compounds e-1 and q-1 shown in Table 2.

As used herein, the phrase "optionally substituted" followed by a chemical moiety (e.g., an optionally substituted aliphatic) means that the chemical moiety may be substituted with one or more (e.g., 1-4) substituents. In some embodiments, aliphatic groups, alkyl groups, aryl groups, heterocyclic groups, carbocyclic groups, and bicyclic or tricyclic ring systems contain one or more substituents. The substituents are selected from those that will be stable under the reaction conditions of the present process, as would be generally known to those skilled in the art. Examples of substituents include halogen, -$Q_1$, —$OQ_1$, —OH, protected OH (such as acyloxy), phenyl (Ph), substituted Ph, —OPh, substituted —OPh, —$NO_2$, —CN, —$NHQ_1$, —$N(Q_1)_2$, —$NHCOQ_1$, —$NHCONHQ_1$, —$NQ_1CONHQ_1$, —$NHCON(Q_1)_2$, —$NQ_1CON(Q_1)_2$, —$NQ_1COQ_1$, —$NHCO_2Q_1$, —$NQ_1CO_2Q_1$, —$COQ_1$, —$CONQ_1$, —$CON(Q_1)_2$, —$S(O)_2Q_1$, —$SONH_2$, —$S(O)Q_1$, —$SO_2NHQ_1$, —$SO_2N(Q_1)_2$, —$NHS(O)_2Q_1$, —$NQ_1S(O)_2Q_1$, =O, =S, =$NNHQ_1$, =$NN(Q_1)_2$, =N—$OQ_1$, =$NNHCOQ_1$, =$NNQ_1COQ_1$, =$NNHCO_2Q_1$, =$NNQ_1CO_2Q_1$, =$NNHSO_2Q_1$, =$NNQ_1SO_2Q_1$, or =$NQ_1$ where $Q_1$ is an optionally substituted aliphatic, aryl or aralkyl group.

As used herein, nitrogen atoms on a heterocyclic ring may be optionally substituted. Suitable substituents on the nitrogen atom include $Q_2$, $COQ_2$, $S(O)_2Q_2$, and $CO_2Q_2$, where $Q_2$ is an aliphatic group or a substituted aliphatic group.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

The term "substantially pure" refers to the stereochemical purity of a compound that is greater than 90%. In some embodiments, the stereochemical purity of a compound is greater than 95%. And in still others, the stereochemical purity of a compound is 99% or greater.

The term "selective crystallization" means crystallization of a substantially pure isomer from a solvent containing a mixture of isomers.

The term "dynamic crystallization" means crystallization of a substantially pure isomer from a solvent containing a mixture of isomers under conditions which cause isomerization of the mixture of isomers to an isomer which selectively crystallizes. For example, in the case of resolving enantiomers, isomerization of the more soluble enantiomer to the less soluble isomer results in crystallization of the less soluble isomer as the equilibrium between the isomers is driven by crystallization toward the less soluble enantiomer. A specific example of dynamic crystallization may include the epimerization of an anomeric carbon in a solvent under conditions which selectively crystallizes one substantially pure enantiomer.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention.

Various "protecting groups," "capping groups," or "amine capping groups" may be used in the methods of this invention (see, e.g., T. W. Greene & P. G. M Wutz, "Protective Groups in Organic Synthesis," 3$^{rd}$ Edition, John Wiley & Sons, Inc. (1999) and the earlier editions of this book). Examples of amine capping groups or protecting groups include, but are not limited to, —$R^7$, —$C(O)R^7$, —$C(O)OR^7$, —$SOR^7$, —$SO_2R^7$, —$SO_3R^7$, —$SO_2N(R^7)_2$, —$C(O)C(O)R^7$, —$C(O)C(O)OR^7$, —$C(O)CH_2C(O)R^7$, —$C(O)N(R^7)_2$, —$(CH_2)_{0-2}NHC(O)R^7$, —$C(=NH)N(R^7)_2$, —$C(O)N(OR^7)R^7$, —$C(=NOR^7)R^7$, —$P(O)(R^7)_2$, and —$P(O)(OR^7)_2$; wherein $R^7$ is hydrogen, an optionally substituted aliphatic group, an optionally substituted aryl group, or an optionally substituted heterocyclic group. Preferably, $R^7$ is (C1-C12)-aliphatic-, (C3-C10)-cycloaliphatic-, (C3-C10)-cycloaliphatic]-(C1-C12)-aliphatic-, (C6-C10)-aryl-, (C6-C10)-aryl-(C1-C12) aliphatic-, (C3-C10)-heterocyclyl-, (C6-C10)-heterocyclyl-(C1-C12)aliphatic-, (C5-C10)-heteroaryl-, or (C5-C10)-heteroaryl-(C1-C12)-aliphatic-.

As used herein, the term "lewis acid" refers to moiety capable of sharing or accepting an electron pair. Examples of lewis acids include, but are not limited to, $BF_3$-etherates and metal halides, alkoxides, and mixed halide/alkoxides (e.g., $Al(Oalkyl)_2Cl$, $Al(Oalkyl)Cl_2$). The metals can be aluminum, titanium, zirconium, magnesium, copper, zinc, iron, tin, boron, ytterbium, lanthanum, and samarium.

EDC is 1-(3-dimethylaminopropyl)-3-ethylcarbodiimide. HOBt is 1-hydroxybenzotriazole. THF is tetrahydrofuran. TFA is trifluoroacetic acid. DCM is dichloromethane. DMAP is 4-dimethylaminopyridine. DIPEA is diisopropylethylamine. DMF is dimethylformamide. TFA is trifluoroacetic acid. CBZ is benzyloxycarbonyl. $^1H$ NMR is nuclear magnetic resonance. TLC is thin layer chromatography.

II. Processes

The processes and compounds described herein are useful for producing modified aspartic acid derivatives, such as aspartic acid aldehyde moieties. Aspartic acid derivatives are useful for preparing caspase inhibitors and/or prodrugs thereof.

The general synthetic procedure shown in Scheme 1 is useful for generating a wide array of chemical species which can be used in the manufacture of pharmaceutical compounds.

SCHEME 1

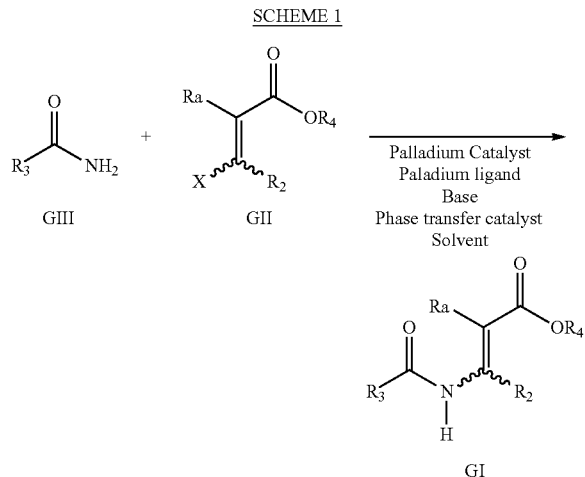

The process shown in Scheme 1 includes reacting a compound of formula GII with the amide GIII in the presence of a palladium catalyst, a palladium ligand and a base in a solvent optionally including a phase transfer catalyst and optionally including water to produce the amido carbonyl compound GI.

The moietys X, $R_a$, $R_2$, $R_3$ and $R_4$ are defined above. As drawn, GII refers to compounds in which X may be cis or trans to Ra, which provides for both the cis and trans compounds of GI, e.g., $R_2$ can be cis or trans to Ra.

In some embodiments, the process may be used to prepare a compound of formula XIV, when the moietys $R^2$ and $R^4$ shown in Scheme I form a substituted heterocyclic ring:

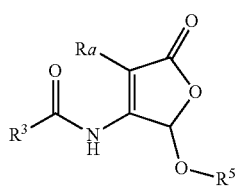

wherein $R^3$ and Ra are defined above and $R^5$ is an optionally substituted aliphatic, optionally substituted aralkyl, optionally substituted heterocyclylalkyl or optionally substituted aryl. Specifically, compound XIV may be produced by reacting a compound of formula XV:

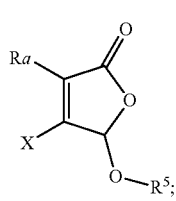

and a compound of formula XIII:

in the presence of a palladium catalyst, a palladium II ligand, a base, a solvent, and optionally a phase transfer catalyst; wherein X, $R^3$, and $R^5$ are defined above.

In carrying out the reaction shown in Scheme 1, the reactants and reagents may be used in any molar amount which provides the desired product. In some embodiments, the ratio of the molar amounts of palladium II salt to palladium ligand is between 1:1 to about 1:5. The ratio of the molar amounts of palladium II salt to the reactant GIII can be between about 1:200 to about 1:1, about 1:100 to about 1:25, or about 1:50 to about 1:10. The ratio of the molar amount of the base relative to the GIII is between about 1:2 to about 10:1. The two reactants, GII and GIII, and the base can be used in nearly equal molar amounts. In some embodiments, the ratio of GII and GIII can be between about 1:3 to about 3:1.

The reaction in Scheme I may be conducted at a temperature between 25° C. and 120° C., e.g., about 50° C., in any solvent that does not adversely interfere with the palladium catalyst, the palladium ligand, and the reactants. Examples of suitable solvents are described herein and can include toluene, dioxane, THF, and mixtures thereof. In some embodiments, the solvent may include water.

After obtaining the compound XIV, the compound of formula XVI:

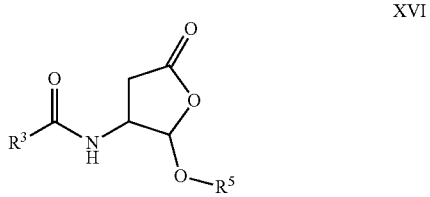

may be obtained by reducing the furanone ring double bond.

The reduction of a furanone ring double bond may be accomplished with a hydride reducing agent, especially a borohydride. Examples of such borohydrides include sodium or lithium borohydride, sodium or lithium triacetoxyborohydride, sodium or lithium cyanoborohydride, tetrabutylammonium cyanoborohydride, sodium or lithium trialkylborohydride, preferably sodium cyanoborohydride. Typically the reaction mixture is adjusted to be mildly acidic, preferably at a pH between 3.0 and 6.0 with acids such as HCl, HBr, acetic acid, formic acid, trifluoroacetic acid, $BF_3.OEt_2$, aluminum trichloride, zinc chloride, or titanium tetrachloride. Optionally, the reaction may be buffered with 1.0-5.0 equivalents of sodium acetate. Optionally, the reaction may be catalyzed by the addition of 1-5% $CoCl_2$/semicorrin, $ZnCl_2$, or 1-2 equivalents of chlorotrimethylsilane. Chiral hydride reducing agents are known such as R- or S-Alpine Hydride® (lithium B-isopinocampheyl-9-bora-bicyclo[3.3.1]nonyl hydride) to provide asymmetric reduction.

Reduction of the ring double bond in, e.g., XIV may also be accomplished by hydrogenation. This is useful when $R^5$ is stable to the hydrogenation conditions, such as when $R^5$ is alkyl. Typical hydrogenation conditions include hydrogen gas at a pressure in the range of about one to 100 atmospheres, usually between about 1 to about 20, or about 1 to about 10 atmospheres, and a catalyst present in the range of about 0.01 to 0.5 equivalents per equivalent of XIV (for example). Suitable catalysts include Pd/C, Pd(OH)2, PdO, Pt/C, PtO$_2$, preferentially Pt/C or Pd/C. Suitable solvents include ethyl acetate, alcohols, such as methanol, ethanol, isopropanol, aromatic hydrocarbons, such as benzene, toluene, xylene, ethereal such as THF, DME, dioxane, preferentially ethanol or THF. When $R^5$ is alkyl or aralkyl, such as benzyl, a rhodium (I) or ruthenium (II) catalyst is preferred for stereoselective reduction. Such catalyst is formed by reacting the metal as one of its various complexes with chiral forms of ligands such as methyl- or ethyl-DuPHOS (1,1-bis-2,5-dialkylphospholano)benzene, DIOP (2,3-O-isopropylidene-2,3-dihydroxy-1,4-bis(diphenylphosphino)butane), BINAP (2,2'-bis(diphenylphosphino)-1,1'-binaphthyl), CHIRAPHOS (bis(diphenylphosphino)butane), BPPM (N-t-butoxycarbonyl-2-(diphenylphosphino)methyl-4-(diphenylphosphino)pyrrolidine), BPPFA (N,N-dimethyl-1-[1',2-bis(diphenylphosphino) ferrocenyl]ethylamine), DEGPHOS (N-benzyl-3,4-bis(diphenylphosphino)pyrrolidine), or alkyl-BPE (bisphospholanoethane). Many other suitable ligands are known in the art. Preferred catalysts are 1,2-bis(2,5-dialkyl-phospholano)benzene (cyclooctadiene)rhodium(I) trifluoromethanesulfonate, where alkyl is a straight chain or branched alkyl group of 1-8 carbons, optionally substituted with an aromatic hydrocarbon such as phenyl.

Use of the (R, R) isomer of these ligands will lead to the (S)-configuration of the α-amino carbon in the product and use of the (S, S) isomer will lead to the (R)-configuration. Suitable solvents include ethyl acetate, alcohols, such as methanol, ethanol, or isopropanol, aromatic hydrocarbons, such as benzene, toluene, or xylene, ethers such as THF, DME, or dioxane. Preferred solvents are toluene or methanol. The reaction concentration of XIV will typically be in the range of about 0.01M to 1.0M, preferably about 0.1M to 1.0M. The reaction temperature is usually in the range of about 0° C. to about 60° C., preferably between about 20° C. to about 40° C. (For the use of rhodium catalysts see: G. Zhu, Z. Chen, X. Zhang; *J. Org. Chem.* (1999) 64, 6907-6910; M. J. Burk, J. G. Allen, W. F. Kiesman; *J. Amer. Chem. Soc.*, (1998), 120, 657-663; M. J. Burk, J. E. Feaster, W. A. Nugent, R. L. Harlow; *J. Amer. Chem. Soc.*, (1993), 115, 10125-10138; For the use of ruthenium catalysts see: J. M. Brown, M. Rose, F. I. Knight, A. Wienand; *Recl Trav Chim Pays-Bas*, (1995), 114, 242-251; M. Saburi, M. Ohnuki, M. Ogasawara, T. Takahashi, Y. Uchida; *Tetrahedron Lett.* (1992), 33, 5783-5786; U. Matteoli, V. Beghetto, A. Scrivanti; *J Molecular Catalysis A: Chemical* 140 (1999) 131-137).

In certain embodiments, when the moiety $R^3$ includes a chiral carbon bound to the carbonyl of the amide, GIII has the stereochemistry shown in

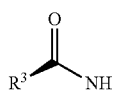

GIV as for example in the structure GIV'

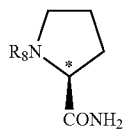

GIV'

The reaction of GIV provides the compound of the formula

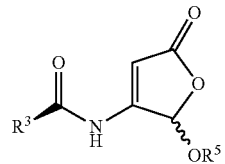

GV

The stereoisomers of GV may be purified by selective crystallization, dynamic crystallization or chromatography.

As described herein, $R^3$ is any organic moiety. Specifically, it will be understood that the $R^3$ group may be selected from any organic moiety that is stable to conditions of the coupling reaction shown in Scheme I, such as those conditions described herein.

In specific embodiments, the general process shown in Scheme 1 is useful for producing caspase inhibitors, such as prodrugs of caspase inhibitors, e.g., ICE inhibitors, and intermediates thereof. In these embodiments, $R^3$ is preferably any moiety that, taken as a whole with the rest of the molecule, provides such an inhibitor. Typically, for caspase inhibitors, the $R^3$ moiety is specifically referred to in the art as a $P_2$, $P_3$, $P_4$, or combination thereof, moiety or site. Examples of $P_2$, $P_3$, $P_4$ moieties are describe in more detail below.

The $P_x$ moiety terms refer to the amino acid sequence next to the aspartyl cleavage site of a particular caspase substrate. $P_1$ refers to the aspartyl residue of the substrate where caspase-induced cleavage occurs in the natural substrate. In the design of new, nonpeptidic caspase inhibitors, the $P_x$ designation is often retained to show which portion of the amino acid sequence has been replaced by the non-peptidic moiety. As used herein, the term "$P_2$-$P_4$" moiety refers to either the amino acid sequence described above or a chemical moiety known to replace such a sequence for the purpose of being a caspase substrate, and in particular an ICE substrate.

Examples of $P_2$-$P_4$ moieties that are non-peptidic are described in U.S. Pat. No. 5,919,790 (Allen et al.); U.S. Pat. No. 5,874,424 (Batchelor et al.); U.S. Pat. No. 5,847,135 (Bemis et al.); U.S. Pat. No. 5,843,904 (Bemis et al.); U.S. Pat. No. 5,756,466 (Bemis et al.); U.S. Pat. No. 5,716,929 (Bemis et al.); U.S. Pat. No. 5,656,627 (Bemis et al.); WO 99/36426 (Warner-Lambert); Dolle et al., *J. Med. Chem.*, 40, 1941 (1997); WO 98/10778 (Idun); WO 98/11109 (Idun); WO 98/11129 (Idun) and WO 98/16502 (Warner Lambert), all of which are incorporated by reference.

As would be recognized by skilled practitioners, a P moiety is not necessarily an amino acid residue. For example, a P4 group could be referred to as an amino capping group (e.g., phenyl-C(O)—). Such P4 groups are exemplified herein.

In another embodiment, this invention provides a process for preparing a compound of formula XVI:

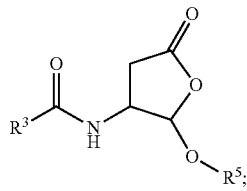

XVI wherein $R^3$ is a $P_4$—$P_3$—$P_2$ moiety of a caspase inhibitor, or portion thereof. Each $P_2$, $P_3$, and $P_4$ group may be incorporated into XVI either individually or together. For example, if $R^3$ is a group other than a $P_2$ group (e.g., a protecting), the $R^3C$=O group may be removed to provide a compound with a free amine group. That amine group and an appropriate $P_2$ moiety may be coupled under, e.g., standard coupling conditions to provide a compound wherein $R^3$ is a $P_2$ moiety of a caspase inhibitor. A $P_3$ and a $P_4$ group may be added together or individually in a similar manner. For example, if the $P_2$ moiety is protected, the protecting group may be removed and a $P_3$ or a $P_4$—$P_3$— moiety (optionally protected) may be incorporated. If a capping group other than a typical protecting group is desired on any of the terminal $P_2$, $P_3$, or $P_4$ residues, such a group may be added routinely by methods known to skilled practitioners.

Accordingly, one embodiment provides a process wherein $R^3$ is a $P_2$— moiety of a caspase inhibitor.

Another embodiment provides a process wherein $R^3$ is a $P_3$—$P_2$— moiety of a caspase inhibitor.

Yet another embodiment provides a process wherein $R^3$ is a $P_4$—$P_3$—$P_2$— moiety of a caspase inhibitor.

Another embodiment provides a process wherein $R^3$ is a $P_4$—$P_3$—$P_2$— moiety of a caspase inhibitor, and wherein said moiety is one of the groups listed in Table 1 below; or wherein said moiety is one of the groups listed in Table 2 below.

According to another embodiment, $R^3$ is a $P_4$—$P_3$—$P_2$— moiety wherein the $P_4$ portion thereof is selected from R—CO, ROC=O, RNHC=O, RC(O)C=O or $RSO_2$ and R is one of the groups listed in Table 3.

According to yet another embodiment, $R^3$ is a $P_4$—$P_3$—$P_2$— moiety selected from one of the groups listed in Table 4.

In any of the embodiments herein, $R^5$ is alternatively an optionally substituted group selected from an aliphatic group, aralkyl group, heterocyclylalkyl group and an aryl group. In more specific embodiments, $R^5$ is methyl, ethyl, propyl, 2-propyl, butyl, pentyl, hexyl, 4-methylpentyl, 2-methylpropyl, cyclopentyl, cyclohexyl, cyclopentylmethyl, cyclohexylmethyl, phenylethyl, phenylpropyl, phenylbutyl, (d)-menthyl, (l)-menthyl, 1-adamantyl, 2-adamantyl, 1-indanyl, 2-indanyl, bornyl, 3-tetrahydrofuranyl, benzyl, α-methylbenzyl, 4-chlorobenzyl, 4-fluorobenzyl, 4-methylbenzyl, 4-(2-propyl)benzyl, or 4-trifluoromethylbenzyl. More specifically, $R^5$ is ethyl or an optionally substituted benzyl; or $R^5$ is ethyl or benzyl.

In any of the embodiments herein, X is preferably Br.

In a specific embodiment, the invention provides a process for preparing a compound of formula I:

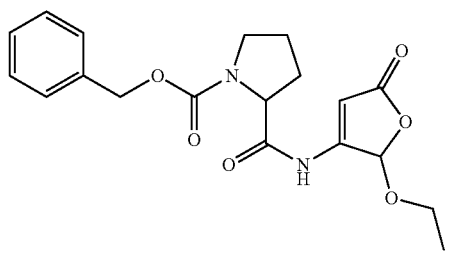

comprising:
(a) reacting a compound of formula II:

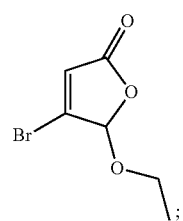

and a compound of formula III:

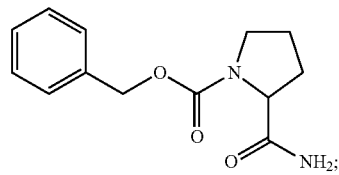

in the presence of a palladium catalyst, a palladium ligand, a base, optionally a phase transfer catalyst and a solvent to provide the compound of formula I.

According to another embodiment, this invention provides a process for preparing a compound of formula IV:

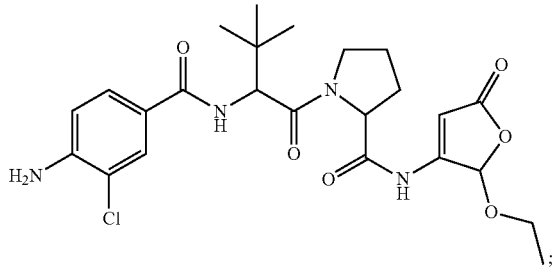

comprising reducing and deprotecting a compound of formula I:

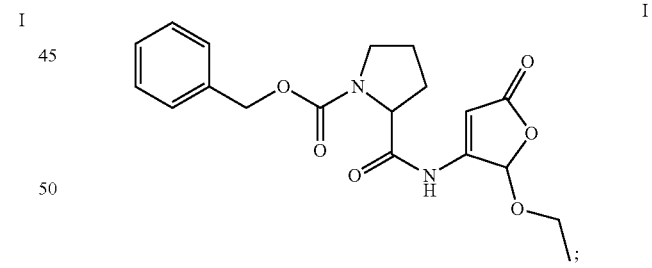

to provide a compound of formula V:

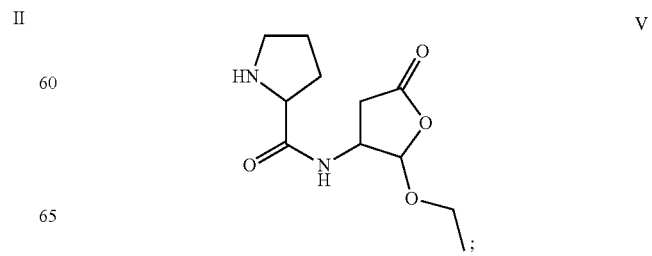

reacting the compound of formula V with cbz-tert-leucine, under appropriate coupling conditions, to provide a compound of formula VI:

VI

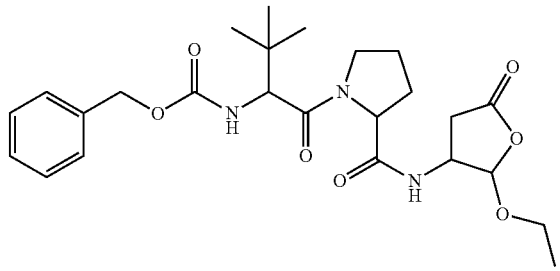

reacting the compound of formula VI under conditions for removing the cbz group; appropriate conditions would be those that provide an amine (or amine salt) (i.e., under conditions for deprotecting the cbz-protected amine of the tert-leucine, such as, e.g., $H_2$ Pd/C, citrate acid (($CO_2H)_2$)); after deprotection the resultant amine is reacted with 4-amino-3-chlorobenzoic, or a derivative thereof that is suitable for coupling to an amine (e.g., 4-amino-3-chlorobenzoyl chloride), under appropriate coupling conditions, to provide the compound of formula IV.

According to another embodiment, the invention provides a process for preparing a compound of formula IV:

IV

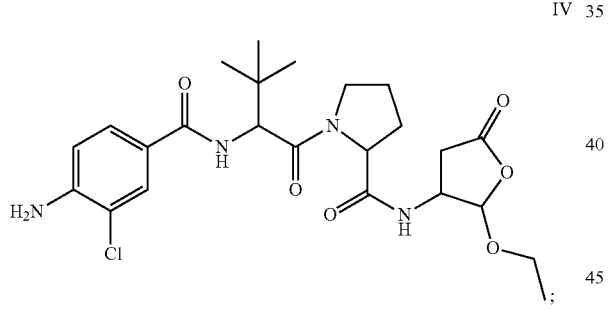

comprising reacting a compound of formula I:

I

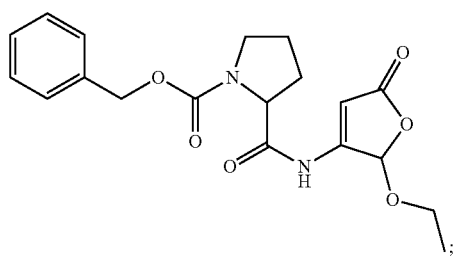

under deprotection conditions, that is, under conditions suitable to remove the cbz group of the proline residue, to provide a compound of formula VII:

VII

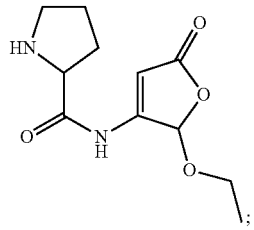

reacting the compound of formula VII with cbz-tert-leucine, under appropriate coupling conditions, to provide a compound of formula VIII:

VIII

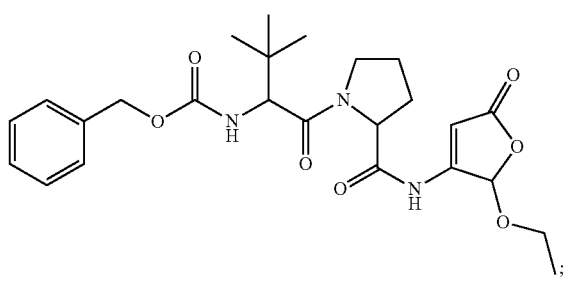

reducing and deprotecting the compound of formula VIII to provide a compound of formula IX:

IX

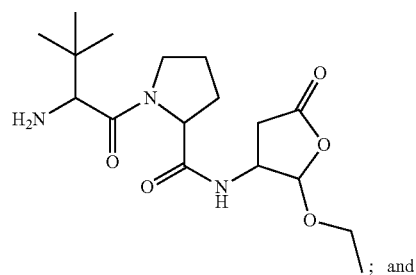

; and reacting a compound of formula IX and 4-amino-3-chlorobenzoic acid, or a derivative thereof that is suitable for coupling to an amine (e.g., the 4,6-dimethoxy-2-hydroxypyrazine ester of 4-amino-3-chlorobenzoic acid), under appropriate coupling conditions, to provide the compound of formula IV.

This invention also provides a compound of formula X, wherein the compound is prepared according to the methods herein:

X

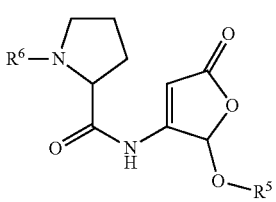

wherein:

R⁵ is an optionally substituted group selected from an aliphatic group, aralkyl group, heterocyclylalkyl group or aryl group; and R⁶ is H or an amine capping group.

The processes described herein are useful for producing a of formula I:

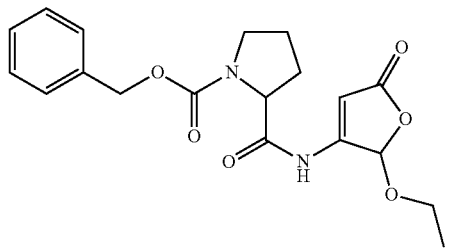

I

The process may also be used to produce substantially pure, diastereomers of compound I shown as formulae IA, IB, IC, and ID.

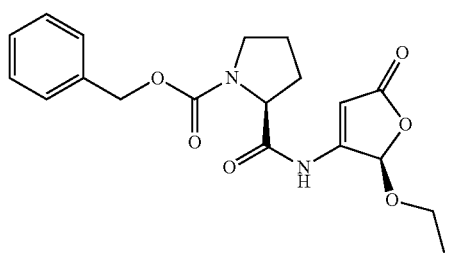

IA

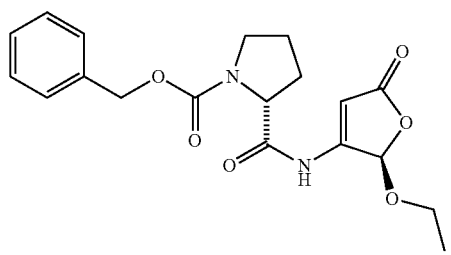

IB

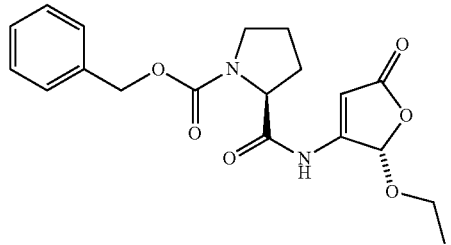

IC

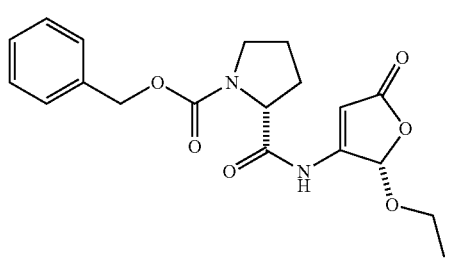

ID

Scheme 1 may also produce a mixture of diastereomers IA and IC:

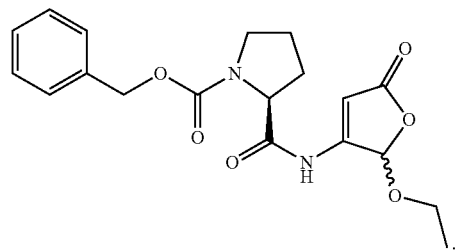

IA/C

According to another embodiment, this invention provides a process for preparing a compound of formula IA:

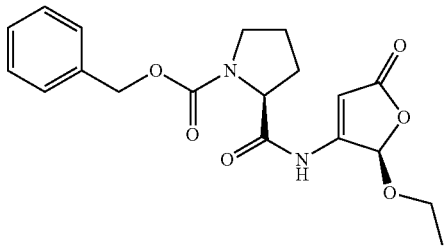

IA comprising the step of selectively crystallizing a compound of formula:

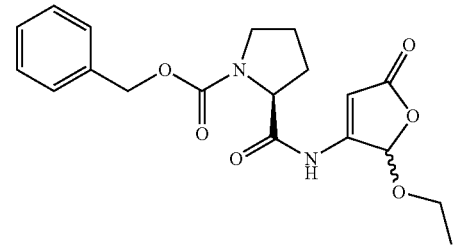

IA/C from toluene.

This selective crystallization step comprises combining the compound of formula IA/C (i.e., a mixture of IA and IC) and toluene (either at room temperature or above) and warming the combination with stirring to dissolve the compound of formula IA/C and cooling the combination with stirring. Upon cooling, the compound of formula IA is obtained as a crystalline solid (about 96:4 to about 97:3 mixture).

According still to another embodiment, this invention provides a process for preparing a compound of formula IA:

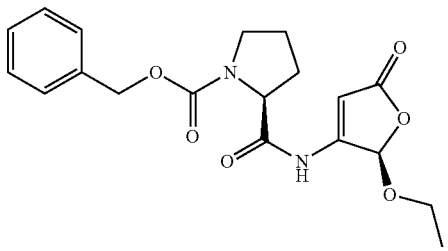

IA comprising the step of dynamic crystallization of a compound of formula:

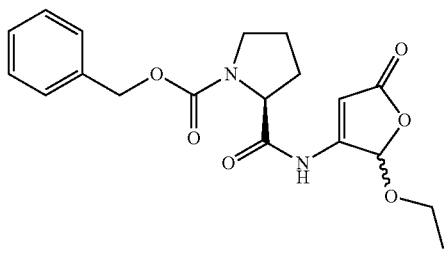

IA/C under in the presence of a Lewis acid and a solvent, optionally including a protic acid. In certain embodiments, the dynamic crystallization is performed with Al(Oalkyl)$_3$ in toluene. In other embodiments, dynamic crystallization is performed with a lewis acid in a solvent containing a protic acid such as HCl, HBr, triflic acid, sulfuric acid, phosphoric acid, or combinations thereof.

In still other embodiments, the isomers IA and IC may be purified and isolated by known chromatographic methods.

In any of the embodiments of this invention involving a compound of formula I, one form of I is represented by the structure:

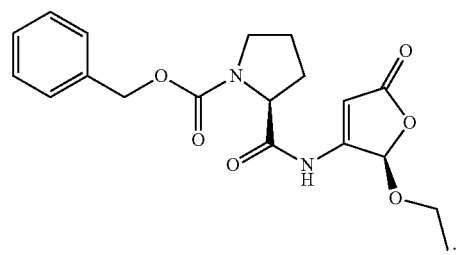

IA

In any of the embodiments of this invention involving a compound of formula II, one form of II is represented by the structure:

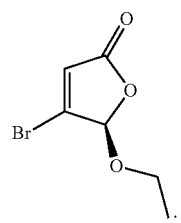

IIA

In any of the embodiments of this invention involving a compound of formula III, one form of III is represented by the structure:

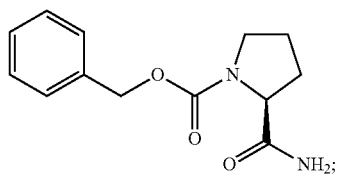

IIIA

In any of the embodiments of this invention involving a compound of formula IV, one form of IV is represented by the structure:

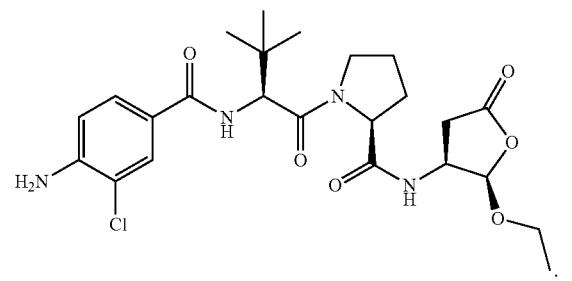

IVA

In any of the embodiments of this invention involving a compound of formula V, one form of V is represented by the structure:

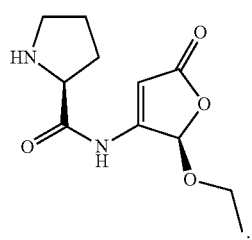

VA

In any of the embodiments of this invention involving a compound of formula VI, one form of VI is represented by the structure:

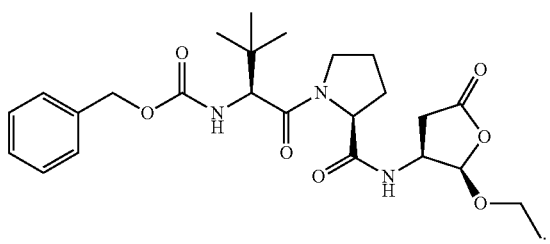

VIA

In any of the embodiments of this invention involving a compound of formula VII, one form of VII is represented by structure:

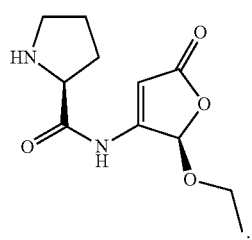

VIIA

In any of the embodiments of this invention involving a compound of formula VIII, one form of VIII is represented by structure:

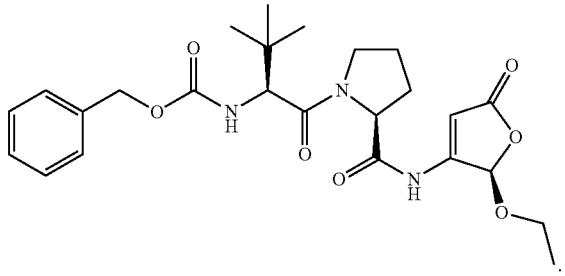

VIIIA

In any of the embodiments of this invention involving a compound of formula IX, one form of IX is represented by structure:

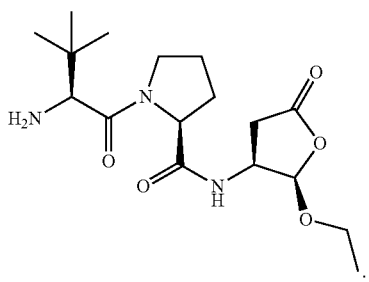

IXA

Also provided are compounds formula XA, XB, XC, or XD, wherein the compound is prepared according to the methods herein:

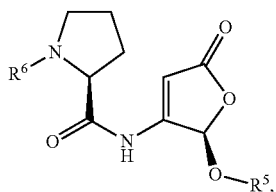

XA

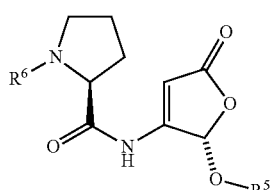

XB

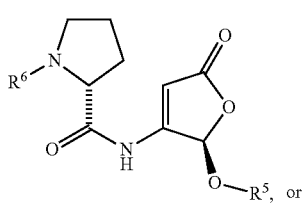

XC, or

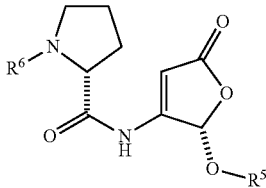

XD wherein:
R$^5$ is optionally substituted aliphatic, aralkyl, or aryl; and
R$^6$ is H or an amine capping group.

In one embodiment, R$^5$ is an optionally substituted group selected from an aliphatic group, aralkyl group, heterocyclylalkyl group and an aryl group.

In another embodiment, R$^5$ is methyl, ethyl, propyl, 2-propyl, butyl, pentyl, hexyl, 4-methylpentyl, 2-methylpropyl, cyclopentyl, cyclohexyl, cyclopentylmethyl, cyclohexylmethyl, phenylethyl, phenylpropyl, phenylbutyl, (d)-menthyl, (l)-menthyl, 1-adamantyl, 2-adamantyl, 1-indanyl, 2-indanyl, bornyl, 3-tetrahydrofuranyl, benzyl, α-methylbenzyl, 4-chlorobenzyl, 4-fluorobenzyl, 4-methylbenzyl, 4-(2-propyl)benzyl, or 4-trifluoromethylbenzyl.

In another embodiment, R$^5$ is ethyl or an optionally substituted benzyl.

In yet another embodiment, R$^5$ is ethyl or benzyl.

In one embodiment of this invention, R$^6$ is an amine capping group and the amine capping group is —C(O)R$^7$ or —C(O)OR$^7$, and the R$^7$ is (C6-C10)-aryl- or (C6-C10)-aryl-(C1-C12)aliphatic-, wherein the aryl is optionally substituted. In one form of this embodiment, —C(O)OR$^7$, wherein R$^7$ is optionally substituted benzyl, preferably benzyl.

Any amines obtained as described herein, may be used with or without isolation from the reaction mixture. The desired caspase inhibitor prodrug may be derived from, e.g., V, VII, or the free amine of XIV (either as depicted or in the reduced form) by attaching the appropriate P$_2$. P$_2$—P$_3$, or P$_2$—P$_3$—P$_4$ moiety. A coupling of an amine with such a moiety may be carried out using the corresponding carboxylic acid, or reactive equivalent thereof, under standard amide bond-forming or coupling conditions. A typical coupling reaction includes a suitable solvent, the amine in a concentration ranging from about 0.01 to 10M, preferably about 0.1 to 1.0M, the requisite carboxylic acid, a base and a peptide coupling reagent.

If an amine is used without isolation, the coupling may be carried out in situ in the solvent of the reaction mixture used in the preparation of the amine, or in a different solvent. To this reaction mixture, the requisite carboxylic acid may be added and the reaction maintained at a temperature in the range of about 0° to 100° C., preferably between about 20° to about 40° C. The base and peptide coupling reagent are then added to the mixture, which is maintained at a temperature in the range of about 0° to about 60° C., preferably between about 20° to about 40° C. The base is typically a tertiary amine base, such as triethylamine, diisopropylethylamine, N-methylmorpholine, DBU, DBN, N-methylimidazole, preferably triethylamine or diisopropylethylamine. The amount of base used is generally up to about 20 equivalents per equivalent of the amine (e.g., IV), preferably at least about 3 equivalents of base. Examples of peptide coupling reagents include DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl-3-ethylcarbodiimide hydrochloride), cyanuric fluoride, cyanuric chloride, TFFH (tetramethyl fluoroformamidinium hexafluorophosphate), DPPA (diphenylphosphorazidate), BOP (benzotriazol-1-yloxytris(dimethylamino)phosphonium hexafluorophosphate), HBTU (O-benzotriazol-1-yl-N,N,N',N'-tetramethyluronium hexafluorophosphate), TBTU (O-benzotriazol-1-yl-N,N,N',N'-tetramethyluronium tetrafluoroborate), TSTU(O—(N-succinimidyl)-N,N,N',N'-tetramethyluronium tetrafluoroborate), HATU (N-[(dimethylamino)-1-H-1,2,3-triazolo[4,5,6]-pyridin-1-ylmethylene]-N-methylmethanaminium hexafluorophosphate N-oxide), BOP-Cl (bis(2-oxo-3-oxazolidinyl)phosphinic chloride), PyBOP ((1-H-1,2,3-benzotriazol-1-yloxy)-tris(pyrrolidino) phosphonium tetrafluorophopsphate), BrOP (bromotris(dimethylamino)phosphonium hexafluorophosphate), DEPBT (3-(diethoxyphosphoryloxy)-1,2,3-benzotriazin-4(3H)-one) PyBrOP (bromotris(pyrrolidino)phosphonium hexafluorophosphate). EDC, HOAT, BOP-Cl and PyBrOP are preferred peptide coupling reagents. The amount of peptide coupling reagent is in the range of about 1.0 to about 10.0 equivalents. Optional reagents that may be used in the amide bond-forming reaction include DMAP (4-dimethylaminopyridine) or active ester reagents, such as HOBT (1-hydroxybenzotriazole), HOAT (hydroxyazabenzotriazole), HOSu (hydroxysuccinimide), HONB (endo-N-hydroxy-5-norbornene-2,3-dicarboxamide), in amounts ranging from about 1.0 to about 10.0 equivalents.

Alternatively, one may treat an amine with a reactive equivalent of the $R^3COOH$ carboxylic acid, such as $P_2$—, $P_3$—$P_2$—, or $P_4$—$P_3$—$P_2$—$C(=O)X^1$, where $C(=O)X^1$ is a group that is more reactive than COOH in the coupling reaction. Examples of —$C(=O)X^1$ groups include groups where $X^1$ is Cl, F, OC(=O)R (R=aliphatic or aryl), SH, SR, SAr, or SeAr.

A number of chemical groups are known that may be used as the $P_3$—$P_2$— portion of the ICE or caspase inhibitor prodrug. Examples of such $P_3$—$P_2$— groups are shown in Table 1 as part of a $P_4$—$P_3$—$P_2$— moiety.

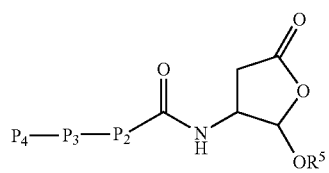

TABLE 1

$P_4$—$P_3$—$P_2$— Groups

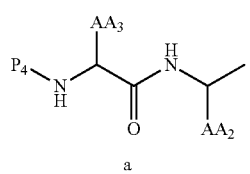

a

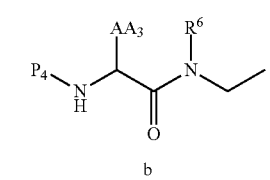

b

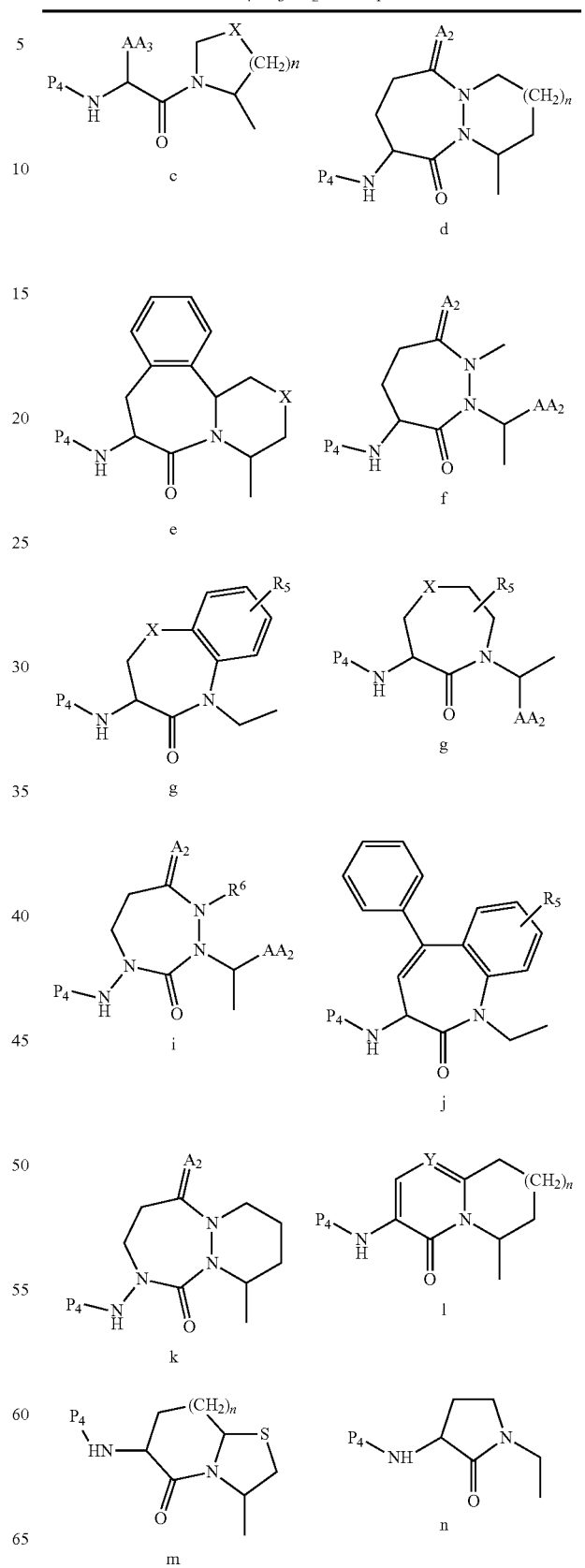

TABLE 1-continued

P$_4$—P$_3$—P$_2$— Groups

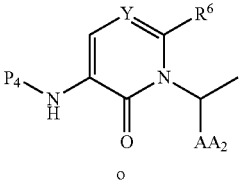

where n is zero to three; AA refers to an amino acid side chain; X is N, O, S, SO, SO$_2$, CHF, CF$_2$, C(R$^3$)$_2$, C=O, or C=NOR; A$^2$ is O, S or H$_2$; Y is N or CH; R is hydrogen, C$_{1-12}$ alkyl group, aryl group, or heteroaryl group, the R groups being optionally substituted with one or more halogen; R$^3$ is an alkyl having one to six carbons; R$^4$ is R—CO, ROC=O, RNHC=O, RC(O)C=O, or RSO$_2$; and R$^5$ is hydrogen, halo, alkyl, alkoxy, haloalkyl, haloalkoxy, amino, phenyl, phenoxy, hydroxy, alkoxycarbonyl, carboxyl, alkylcarbonyl, alkylsulfonyl, alkylsulfoxyl, alkylcarbonylamino, alkylcarbonylalkylamino, alkylamino, dialkylamino, aminosulfonyl, or cyano; and R$^6$ and R$^7$ are independently selected from R$^3$, aryl, heteroaryl, (C$_{1-12}$ alkyl)aryl, (C$_{1-12}$)benzocycloalkyl, or (C$_{1-12}$ alkyl)heteroaryl.

Preferred P$_4$—P$_3$—P$_2$— groups are shown in Table 2.

TABLE 2

Preferred P$_4$—P$_3$—P$_2$—Groups

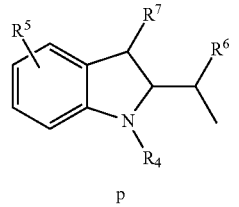
a-1

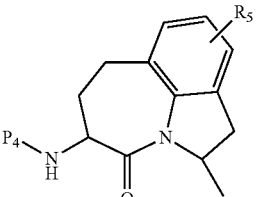
b-1

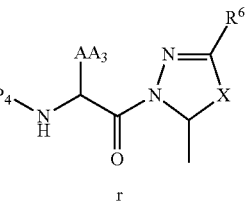
c-1

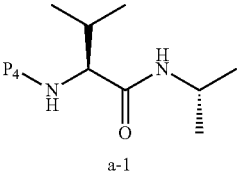
c-2

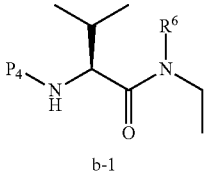
c-3

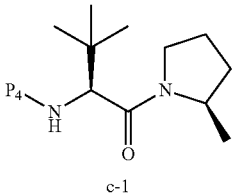
c-4

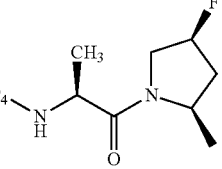
c-5

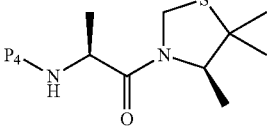
c-6

TABLE 2-continued
Preferred P₄—P₃—P₂—Groups
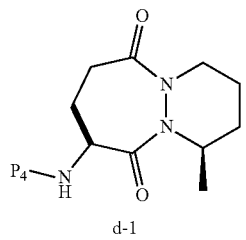
d-1
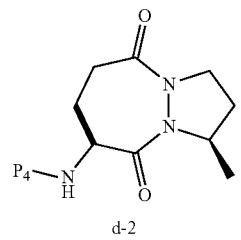
d-2
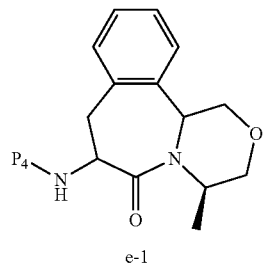
e-1
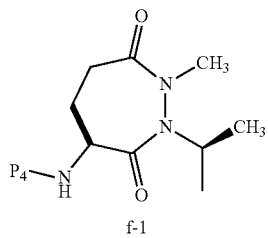
f-1
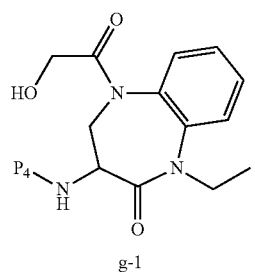
g-1
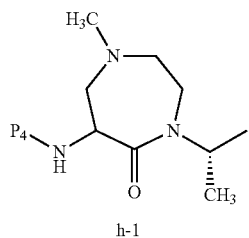
h-1
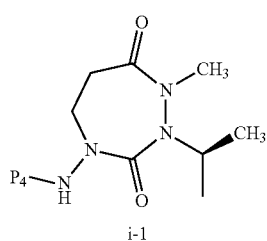
i-1
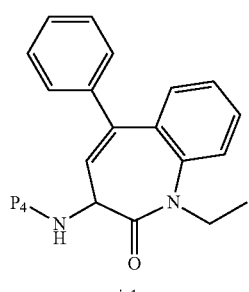
j-1
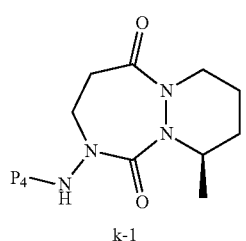
k-1
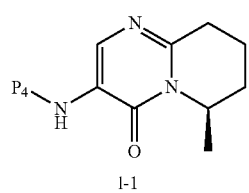
l-1
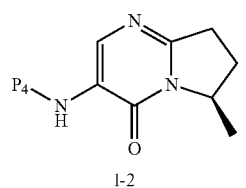
l-2
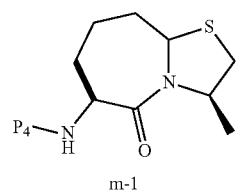
m-1

TABLE 2-continued
Preferred P₄—P₃—P₂—Groups
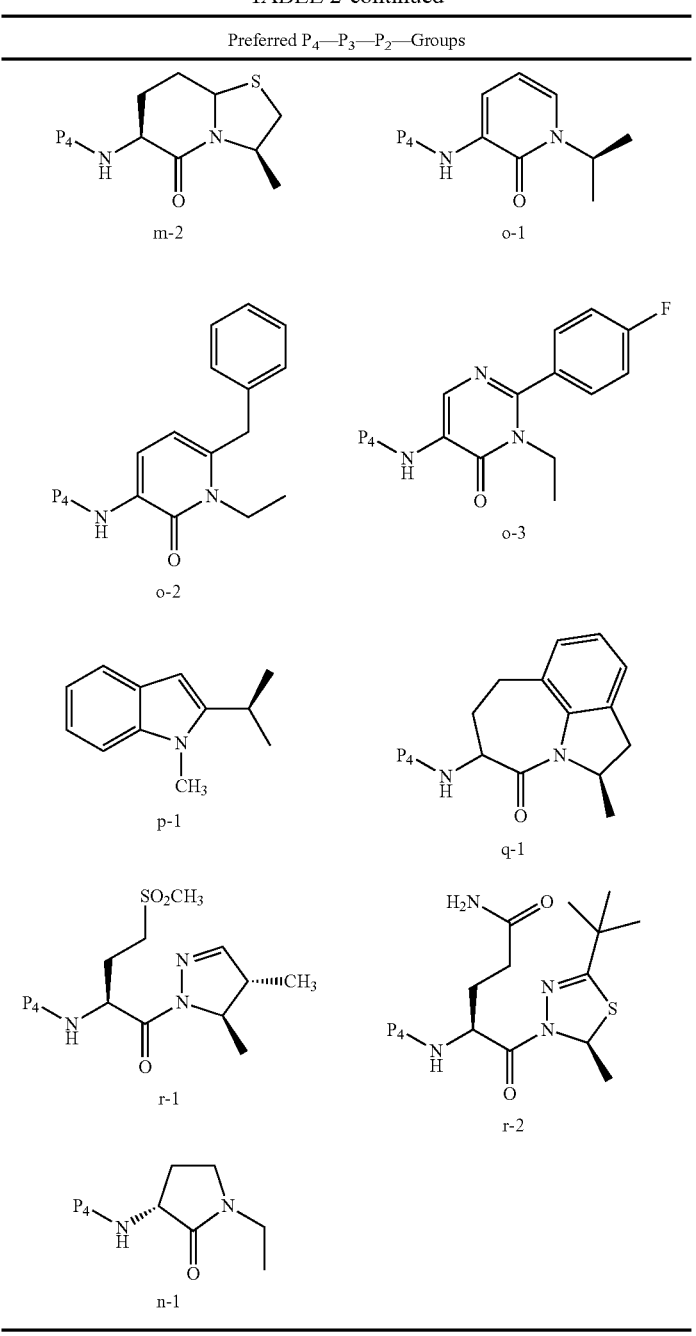
where R⁶ is an optionally substituted benzyl as described below or 2-indanyl, and the P₄ moiety is represented by R-T-, wherein R-T- is R—CO, ROC=O, RNHC=O, RC(O)C=O, or RSO₂.
Preferred R groups of P₄ are shown in Table 3.
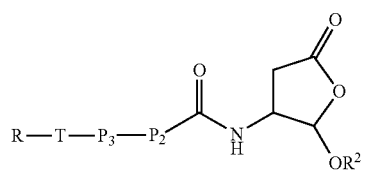
TABLE 3
Preferred R Groups of P₄
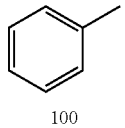
100
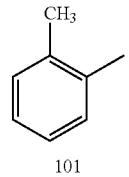
101

TABLE 3-continued
Preferred R Groups of P₄
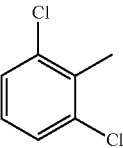
102
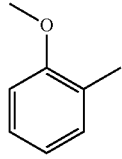
103
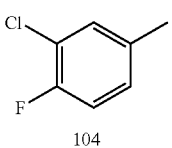
104
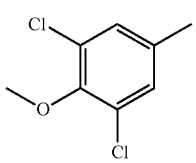
105
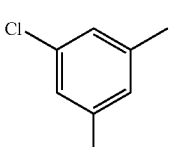
106
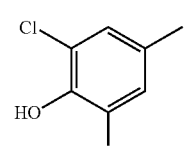
107
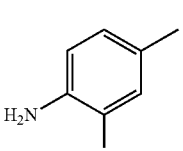
108
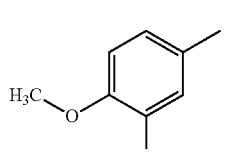
109
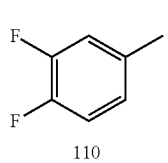
110
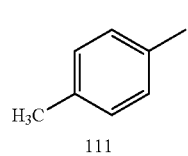
111
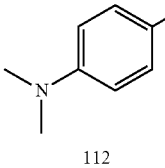
112
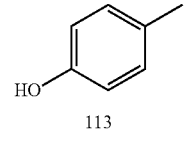
113
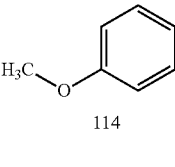
114
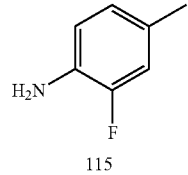
115
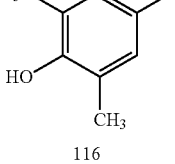
116
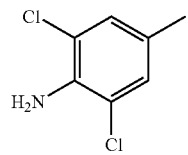
117
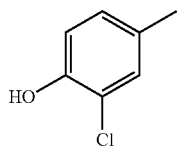
119
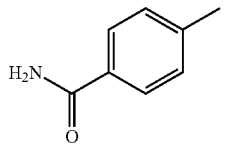
120
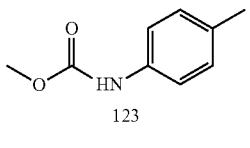
122
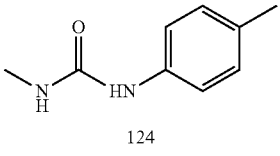
123
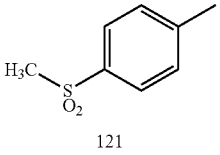
124
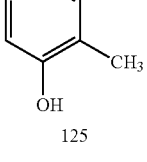
121
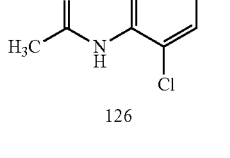
125
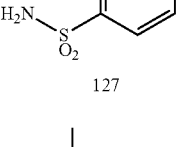
126
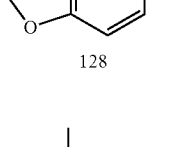
127
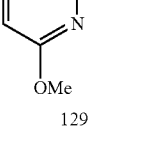
128
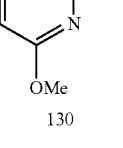
129
130
131
132
133
134

TABLE 3-continued

Preferred R Groups of P$_4$

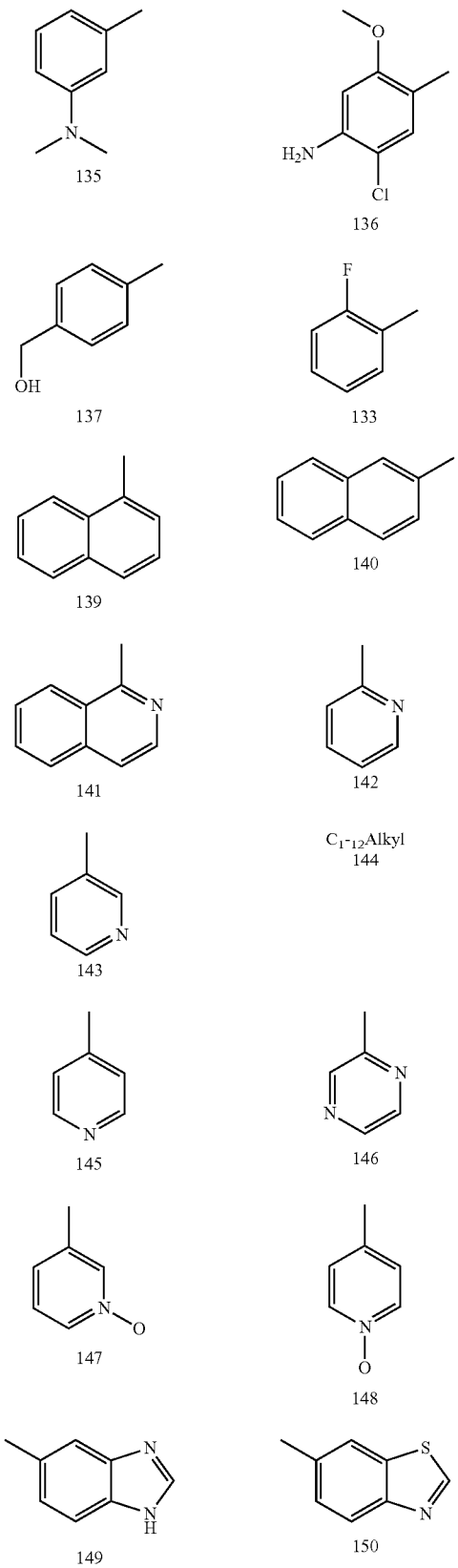

In specific embodiments, R-T- is R—CO where R is 1-naphthyl, 2-naphthyl, 1-isoquinolinyl, or

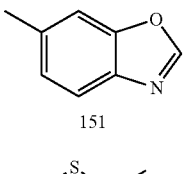

where positions 3 and 5 of R are independently and optionally substituted by halogen, preferably chloro, or C$_{1-3}$ alkyl, and position 4 is optionally substituted by amino, acetamido, hydroxy or methoxy.

The most preferred P$_4$—P$_3$—P$_2$— groups are shown in Table 4.

TABLE 4

Most Preferred P$_4$—P$_3$—P$_2$— Groups

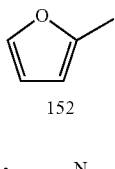

TABLE 4-continued

Most Preferred P$_4$—P$_3$—P$_2$— Groups b-1b d-1a g-1a g-2a o-2a c-7a c-1a c-6a where R is, referring to Table 3, one of the following groups: 100, 105, 107, 108, 114, 117, 119, 126, 136, 139, 140, and 141.

In attaching the P$_4$—P$_3$—P$_2$— moiety, or portion thereof, the moiety may be attached in one piece as or subunits of the moiety may be added in a sequential manner as described above. For example, Cbz-protected proline may be coupled to XV (or if R$^5$ is ethyl with II):

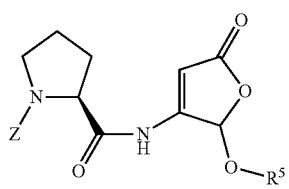

After removal of the Cbz group, a P$_3$ or P$_3$—P$_4$ moiety may be attached by alkylation or acylation of the proline nitrogen.

In certain embodiments, methods of the present process proceed through the butenolactone XV where X is chloro, bromo or iodo:

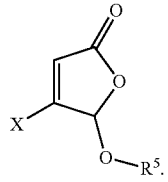

XV

A preferred starting butenolactone is the bromofuranone XV (wherein X=Br), which may be obtained according to Escobar et al., *An. Quim.*, 1971, 67, 43. Alternatively, other reactants of the formula GIIA and GIIB may be commercially available or produced from know methods. See, for example, "Comprehensive Organic Transformations: A Guide to Functional Group Preparations," 2nd Edition, by Richard C. Larock, pages 638, 659, 661, 724.

Also within the scope of this invention, another embodiment of the coupling reaction of an amine proceeds by acylation of the anion of the amine using a reactive equivalent of the carboxylic acid, such as P$_2$—, P$_2$—P$_3$—, or P$_2$—P$_3$—P$_4$—C(=O)X$^1$, where C(=O)X$^1$ is as described above. The anion of the amine is first generated by treating the amine in a solvent with any suitable base. Examples of solvents that may be used include ethereal solvents such as THF, DME, dioxane, diethyl ether, methyl-tert-butyl ether; aromatic hydrocarbons, such as benzene, toluene, xylene; halogenated hydrocarbons, such as dichloromethane, carbon tetrachloride, dichloroethane; or other organic solvents, such as acetonitrile. Preferred solvents include THF, DME, toluene or dichloromethane. Suitable bases for generating the anion include organic bases such as an alkali metal hydride, an alkali metal tert-butoxide, an alkyl or aryl lithium, such as methyl-, butyl- or phenyllithium; an alkali metal amide, such as lithium-, sodium- or potassium bis(trimethylsilyl)amide, diisopropylamide, or tetramethylpiperidine. Preferred bases include lithium bis(trimethylsilyl)amide, lithium diisopropylamide, or lithium tetramethylpiperidine. The anion of the amine is treated with the carboxylic acid equivalent at a reaction temperature that may be in the range of about –78° C. to 120° C., preferably between about 0° C. to 60° C.

Reduction conditions for reducing the double bond in the furanone ring may also be used as deprotection conditions. For example, when R$^3$ (in XIV) or R$^6$ (in X) is cbz, conditions may be used to reduce the double bond and to also remove the cbz group.

Methods herein describe a sequence in which the butenolactone is first coupled to a caspase P$_x$ or P$_{x-y}$ moiety and then the ring double bond is reduced. Alternatively, the reduction and coupling may be performed in reverse order.

In still another embodiment, this invention provides a process for preparing a compound of formula XVI:

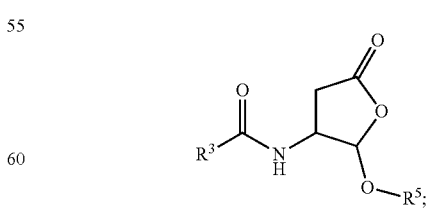

XVI wherein R$^3$ is a P$_4$—P$_3$—P$_2$ moiety of a caspase inhibitor, the P$_4$—P$_3$—P$_2$ is c-1 of Table 2, the P$_4$ is 108 of Table 3, R$^5$ is as defined herein (e.g., ethyl) and the process is according to the methods herein.

This invention also provides a process for preparing a compound of formula IVA:

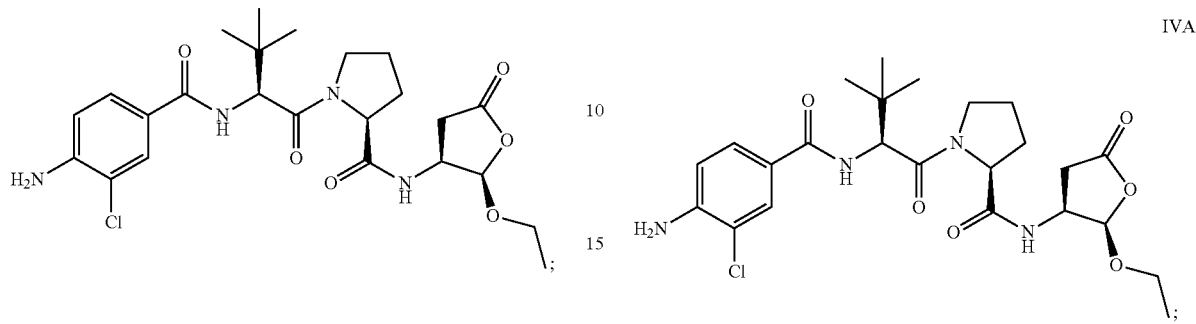

comprising selective crystallization of a compound of formula:

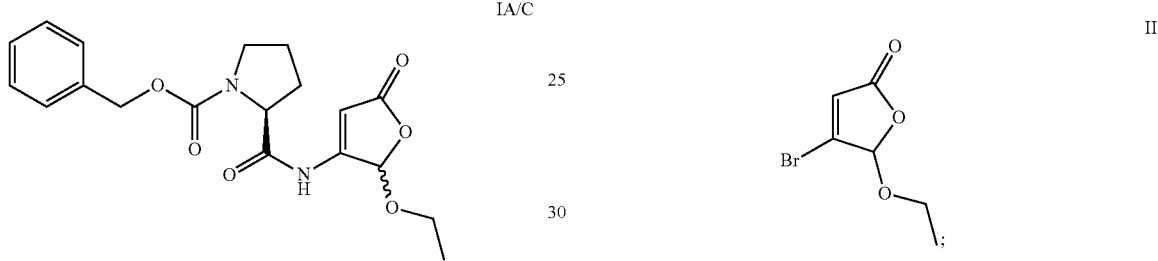

from toluene.

Alternatively, a process for preparing a compound of formula IVA:

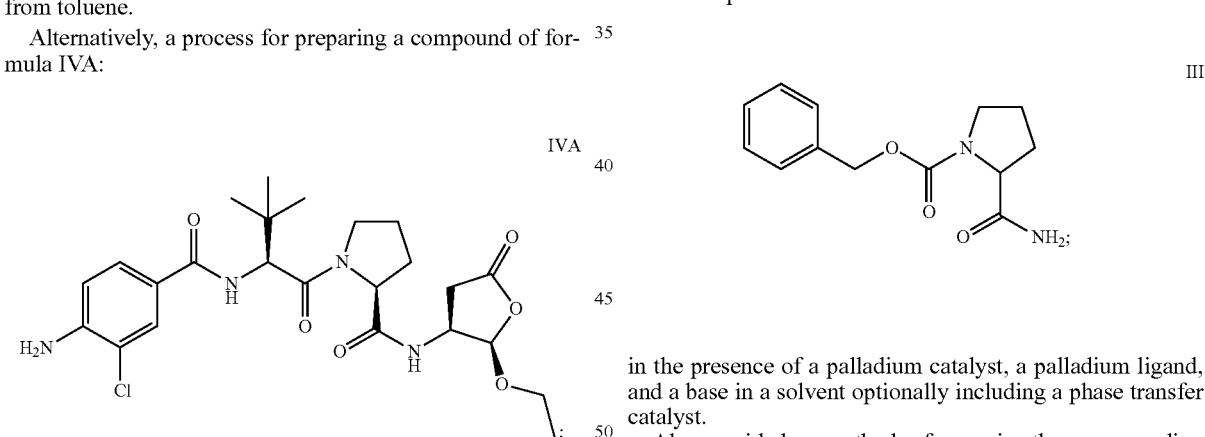

comprises dynamic crystallization of a compound of formula:

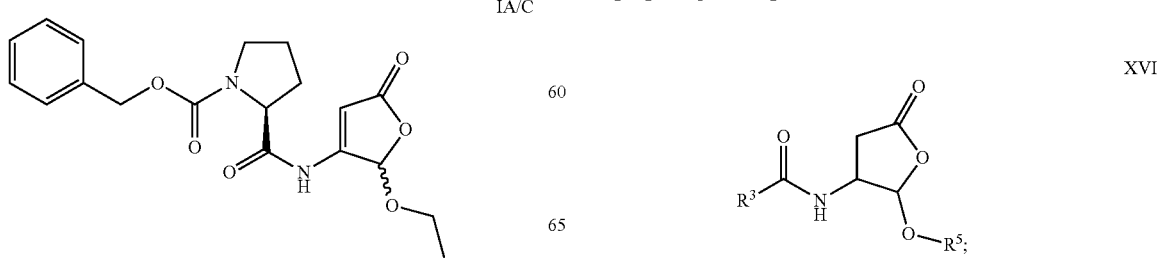

by contacting the mixture of IA/C with a Lewis acid in a solvent optionally including a protic acid.

This invention also provides a process for preparing a compound of formula IVA:

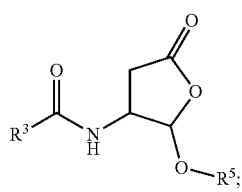

comprising, reacting a compound of formula II:

II and a compound of formula III:

III in the presence of a palladium catalyst, a palladium ligand, and a base in a solvent optionally including a phase transfer catalyst.

Also provided are methods of preparing the corresponding aldehyde compound (of e.g., XVI) by these processes. For example, compound IV prepared according to this invention, may be converted to the corresponding aldehyde compound, that is by converting the furanone to an aldehyde.

In another embodiment, this invention provides a process for preparing a compound of formula XVI:

XVI wherein $R^3$ is a $P_4$—$P_3$—$P_2$ moiety of a caspase inhibitor, the $P_4$—$P_3$—$P_2$ is d-1 of Table 2, $P_4$ is 141 of Table 3, $R^5$ is as defined herein (e.g., ethyl), and the process is according to the methods herein.

Accordingly, this compound (see compound 412f and/or corresponding compound 412 as disclosed in WO 97/22619, which is incorporated herein by reference) is prepared by reacting a compound of formula II:

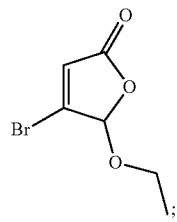

II and an appropriate amide compound, in the presence of a palladium catalyst, a palladium ligand, a base, optionally a phase transfer catalyst and an appropriate solvent. An appropriate amide compound would be derived from the P4-P3-P2 group d-1a in Table 4, i.e., a compound:

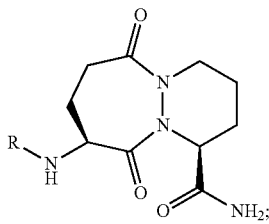

wherein R is either H or an isoquinolinoyl (i.e., the P4 group 141 in Table 3, wherein there is a carbonyl linker between the compound and the isoquinolinoyl group.

In still further embodiments, the invention provides a process of preparing a beta-amido carbonyl compound of formula XXX:

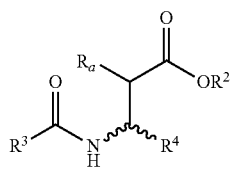

XXX comprising the steps of:
a) reacting a compound of formula XII:

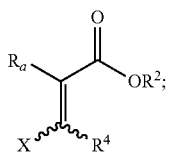

XII with a compound of formula XIII:

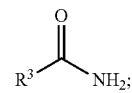

XIII in the presence of a palladium catalyst, a palladium ligand, a base, in a solvent optionally a phase transfer catalyst, to produce a compound of the formula XXXI

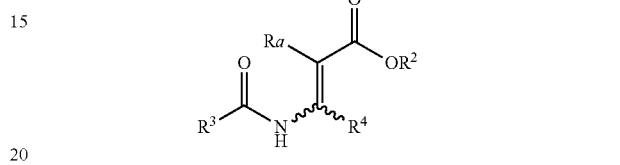

XXXI wherein:
X is a leaving group;
Each $R_a$ is H, an optionally substituted alkyl, an optionally substituted aryl, —CN, —C(O)—Oalkyl or halogen;
Each $R^2$ is independently an optionally substituted aliphatic group, an optionally substituted heterocyclic group, and an optionally substituted aryl group;
Each $R^4$ is independently an optionally substituted aliphatic, an optionally substituted heterocycle, an optionally substituted aryl, or $R^2$ and $R^4$ together with the groups to which they are bound, form an optionally substituted 5- to 8-membered heterocyclic ring;
Each $R^3$ is an optionally substituted aliphatic, an optionally substituted aryl, an optionally substituted heteroalkyl, a protecting group, $P_2$—, $P_3$—$P_2$—, or $P_4$—$P_3$—$P_2$—;
$P_2$— is

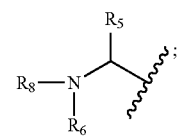

$P_3$—$P_2$ is

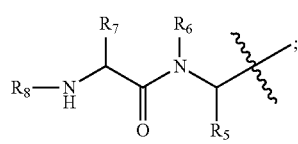

$P_4$—$P_3$—$P_2$— is

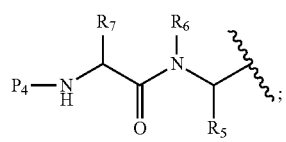

$P_4$ is R-T;
T is —C(O)—, —O—C(O)—, —NHC(O)—, —C(O)C(O)— or —SO$_2$—;

Each R is independently an optionally substituted aliphatic, an optionally substituted aryl, or $P_2$ Each $R_5$ is independently H, an optionally substituted aliphatic, an optionally substituted heteroalkyl, an optionally substituted heteroaryl, or an optionally substituted phenyl;

Each $R_6$ is independently an optionally substituted aliphatic, an optionally substituted heteroalkyl, an optionally substituted heteroaryl, an optionally substituted phenyl, or $R_5$ and $R_6$ taken together with the atoms to which they are attached form a 5 to 7 membered, optionally substituted monocyclic heterocycle, or a 6 to 12 membered, optionally substituted bicyclic heterocycle, in which each heterocycle ring optionally contains an additional heteroatom selected from —O—, —S— or —$NR_{50}$;

Each $R_7$ is independently H, an optionally substituted aliphatic, an optionally substituted heteroalkyl, an optionally substituted heteroaryl, or an optionally substituted phenyl, or $R_7$ and $R_6$ together with the atoms to which they are attached form a 5 to 7 membered, optionally substituted monocyclic heterocycle or aryl (see, for example, compounds f, h, i, n, and o shown in Table 1 and compounds o-1, o-2, and o-3 shown in Table 2), or a 6 to 12 membered, optionally substituted bicyclic fused ring system, in which each of the fused rings optionally contains an additional heteroatom selected from —O—, —S— or —$NR_{50}$— (see, for example, compounds g and j shown in Table 1, and compounds g-1 and j-1 shown in Table 2), or when $R_5$ and $R_6$ together to with the atoms to which they are attached form a ring, $R_7$ and the ring system formed by $R_5$ and $R_6$ form a 8- to 14-membered optionally substituted bicyclic fused ring system (see, for example, compounds g, k, l, and m, shown in Table 1 and compounds d-1, d-2, k-1, l-1, l-2, m-1, and m-2 shown in Table 2), wherein the bicyclic fused ring system is optionally further fused with an optionally substituted phenyl to form an optionally substituted 10- to 16-membered tricyclic fused ring system (see, for example, compounds e and q shown in Table 1, and compounds e-1 and q-1 shown in Table 2);

Each $R_8$ is independently H or a protecting group; and

Each $R_{50}$ is independently H, an optionally substituted aliphatic, an optionally substituted heteroalkyl, an optionally substituted heteroaryl, or an optionally substituted phenyl; and m is 0 to 2.

In some embodiments, $R_3$ is an organic moiety.

In certain embodiments, the variable R in $P_4$ may be an aliphatic, aryl, or heteroaryl, each optionally substituted with 1 to 3 aliphatic, halo, alkoxy, —CN, —$NO_2$, —$N(R_{50})_2$, —$SO_mN(R_{50})_2$, —$NC(O)R_{50}$, —$SO_mR_{50}$ or heterocycloalkyl.

The process further comprises reducing the compound of formula XXXI to produce a compound of Formula XXX.

In some embodiments $P_2$— has the structure

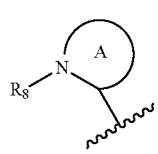

in which Ring A is a 5 to 7 membered, optionally substituted monocyclic heterocycle, or a 6 to 12 membered, optionally substituted bicyclic heterocycle, in which each heterocycle ring optionally contains an additional heteroatom selected from —O—, —S— or —$NR_{50}$—, $R_{50}$ is H, an optionally substituted aliphatic, an optionally substituted heteroalkyl, an optionally substituted heteroaryl, or an optionally substituted phenyl.

In specific embodiments, Ring A has the structure:

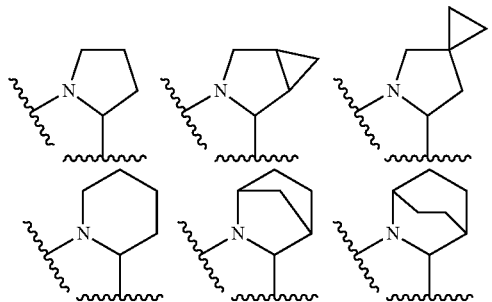

$P_2$— has the structure

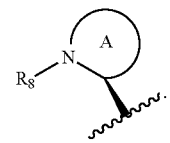

In certain embodiments, Ring A has the structure

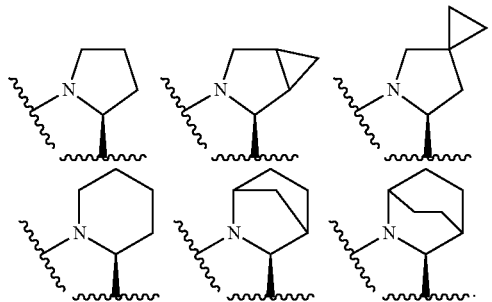

In specific embodiments $P_2$— has the structure

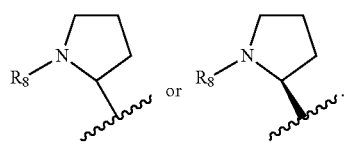

In another embodiment, the a process for producing a compound of the formula comprises:

a) reacting a compound of the formula:

with a compound of the formula:

in the presence of a palladium catalyst, a palladium ligand, a base, optionally a phase transfer catalyst and a solvent, to produce a compound of the formula wherein:

X is a leaving group such as Br;

Each $R_a$ is H, an optionally substituted alkyl, an optionally substituted aryl, —CN, —C(O)—Oalkyl or halogen;

Each $R^2$ is independently an optionally substituted aliphatic group, an optionally substituted heterocyclic group, and an optionally substituted aryl group;

Each $R^4$ is independently an optionally substituted aliphatic, an optionally substituted heterocycle, an optionally substituted aryl, or $R^2$ and $R^1$ together with the groups to which they are bound, form an optionally substituted 5- to 8-membered heterocyclic ring;

$P_2$ is

T is —C(O)—, —O—C(O)—, —NHC(O)—, —C(O)C(O)— or —SO$_2$—;

Each R is independently an aliphatic, or aryl, each optionally substituted with 1 to 3 aliphatic, halo, alkoxy, —CN, —NO$_2$, —N(R$_{50}$)$_2$, —SO$_m$N(R$_{50}$)$_2$, —NC(O)R$_{50}$, —SO$_m$R$_{50}$ or heterocycloalkyl;

Each $R_5$ is independently H, an optionally substituted aliphatic, an optionally substituted heteroalkyl, an optionally substituted heteroaryl, or an optionally substituted phenyl;

Each $R_6$ is independently H, an optionally substituted aliphatic, an optionally substituted heteroalkyl, an optionally substituted heteroaryl, an optionally substituted phenyl, or $R_5$ and $R_6$ taken together with the atoms to which they are attached form a 5 to 7 membered, optionally substituted monocyclic heterocycle, or a 6 to 12 membered, optionally substituted bicyclic heterocycle, in which each heterocycle ring optionally contains an additional heteroatom selected from —O—, —S— or —NR$_7$—;

Each $R_7$ is independently H, an optionally substituted aliphatic, an optionally substituted heteroalkyl, an optionally substituted heteroaryl, or an optionally substituted phenyl;

$R_8$ is H or a protecting group; and m is 0 to 2.

In a specific embodiment, a compound of the formula in which $R^9$ is $C_1$-$C_5$ alkyl, is reacted with to produce the compound The process may further comprise the step of contacting a racemic mixture of compounds of the formula in which $R_8$ is a protecting group, with a Lewis acid, optionally in the presence of a protic acid, in an organic solvent to provide compounds having the structure

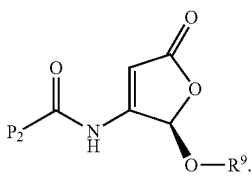

In some embodiments, resolution of the alkoxyfuranones may be achieved by selectively recrystallization from an organic solvent.

The process may include reducing the double bond in XXXI. For instance, the compound of the formula

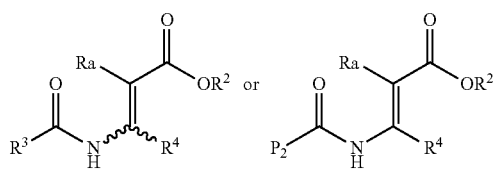

is reduced under conditions described herein to provide a compound of the formula

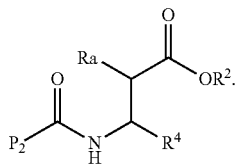

After producing this compound, $P_3$— and $P_4$— moieties may be coupled to the compound as described above.

In still another embodiment, the process for producing a compound of the formula

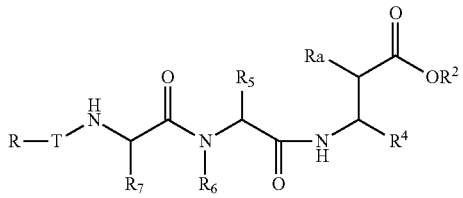

comprises:
(a) reducing the compound of the formula

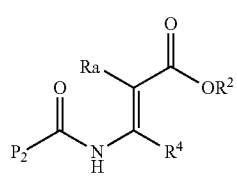

to provide a compound of the formula

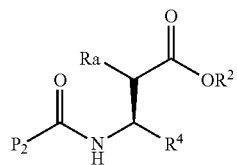

wherein

Each $R_a$ is H, an optionally substituted alkyl, an optionally substituted aryl, —CN, —C(O)—Oalkyl or halogen;

Each $R^2$ is independently an optionally substituted aliphatic group, an optionally substituted heterocyclic group, and an optionally substituted aryl group;

Each $R^4$ is independently an optionally substituted aliphatic, an optionally substituted heterocycle, an optionally substituted aryl, or $R^2$ and $R^1$ together with the groups to which they are bound, form an optionally substituted 5- to 8-membered heterocyclic ring;

$P_2$ is

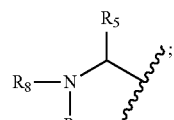

T is —C(O)—, —O—C(O)—, —NHC(O)—, —C(O)C(O)— or —SO$_2$—;

Each R is independently an aliphatic, or aryl, each optionally substituted with 1 to 3 aliphatic, halo, alkoxy, —CN, —NO$_2$, —N(R$_{50}$)$_2$, —SO$_m$N(R$_{50}$)$_2$, —NC(O)R$_{50}$, —SO$_m$R$_{50}$ or heterocycloalkyl;

Each $R_5$ is independently H, an optionally substituted aliphatic, an optionally substituted heteroalkyl, an optionally substituted heteroaryl, or an optionally substituted phenyl;

Each $R_6$ is independently H, an optionally substituted aliphatic, an optionally substituted heteroalkyl, an optionally substituted heteroaryl, an optionally substituted phenyl, or $R_5$ and $R_6$ taken together with the atoms to which they are attached form a 5 to 7 membered, optionally substituted monocyclic heterocycle, or a 6 to 12 membered, optionally substituted bicyclic heterocycle, in which each heterocycle ring optionally contains an additional heteroatom selected from —O—, —S— or —NR$_{50}$—;

Each $R_{50}$ is independently H, an optionally substituted aliphatic, an optionally substituted heteroalkyl, an optionally substituted heteroaryl, or an optionally substituted phenyl;

$R_8$ is a protecting group; and m is 0 to 2.

A process for producing a compound of the formula

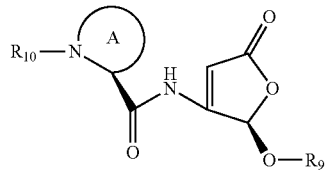

comprises:

a) contacting a racemic mixture of compounds represented by the formula

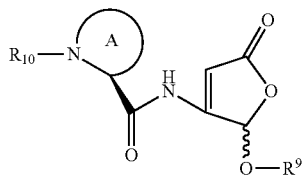

with a Lewis acid in an organic solvent optionally including a protic acid, wherein Ring A is a 5 to 7 membered, optionally substituted monocyclic heterocycle, or a 6 to 12 membered, optionally substituted bicyclic heterocycle, in which each heterocycle ring optionally contains an additional heteroatom selected from —O—, —S— or —NR$_{50}$—;

Each R$^9$ is a C$_1$-C$_5$ alkyl;

Each R$^{10}$ is H, a protecting group, P$_3$— or P$_4$—P$_3$—;

P$_3$ is

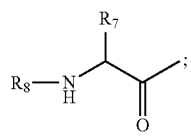

P$_4$ is R-T;

T is —C(O)—, —O—C(O)—, —NHC(O)—, —C(O)C(O)— or —SO$_2$—; and

Each R is independently an aliphatic, aryl, or a heteroaryl, each optionally substituted with 1 to 3 aliphatic, halo, alkoxy, —N(R$_{50}$)$_2$, —SO$_m$N(R$_{50}$)$_2$, —NC(O)R$_{50}$, —SO$_m$R$_{50}$ or heterocycloalkyl;

Each R$_7$ is independently H, an optionally substituted aliphatic, an optionally substituted heteroalkyl, an optionally substituted heteroaryl, or an optionally substituted phenyl, or R$_7$ and the Ring A form a 8- to 14-membered optionally substituted bicyclic fused ring system, wherein the bicyclic fused ring system is optionally further fused with an optionally substituted phenyl to form an optionally substituted 10- to 16-membered tricyclic fused ring system;

Each R$_{50}$ is independently H, an optionally substituted aliphatic, an optionally substituted heteroalkyl, an optionally substituted heteroaryl, or an optionally substituted phenyl;

R$_8$ is a protecting group; and m is 0 to 2.

Alternatively, resolution of

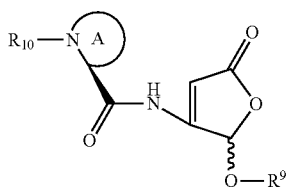

may be achieved by chromatography or selective crystallization from an organic solvent.

A process for producing a compound of the formula

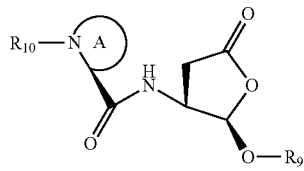

comprises:

a) reducing the compound of the formula

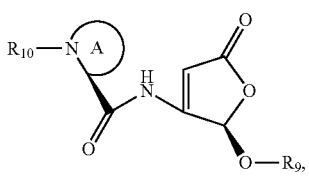

wherein

Each R$^{10}$ is H, a protecting group, P$_3$— or P$_4$—P$_3$—;

P$_3$— is

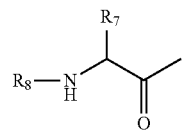

P$_4$—P$_3$— is

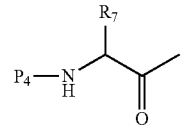

P$_4$ is R-T-;

T is —C(O)—, —O—C(O)—, —NHC(O)—, —C(O)C(O)— or —SO$_2$—;

Each R is independently an aliphatic, aryl, or heteroaryl, each optionally substituted with 1 to 3 aliphatic, halo, alkoxy, —CN, —NO$_2$, —N(R$_{50}$)$_2$, —SO$_m$N(R$_{50}$)$_2$, —NC(O)R$_{50}$, —SO$_m$R$_{50}$ or heterocycloalkyl;

Each R$_7$ is independently H, an optionally substituted aliphatic, an optionally substituted heteroalkyl, an optionally substituted heteroaryl, or an optionally substituted phenyl, or R$_7$ and the Ring A form a 8- to 14-membered optionally substituted bicyclic fused ring system, wherein the bicyclic fused ring system is optionally further fused with an optionally substituted phenyl to form an optionally substituted 10- to 16-membered tricyclic fused ring system;

Each R$_{50}$ is independently H, an optionally substituted aliphatic, an optionally substituted heteroalkyl, an optionally substituted heteroaryl, or an optionally substituted phenyl;

R$_8$ is a protecting group; and m is 0 to 2.

The processes described herein can be used to produce aspartic acid derivatives such as aspartic acid aldehyde moieties. For instance, the processes described herein can be used to produce compounds containing the P4-P3-P2- moieties shown in Tables 1, 2, 3, and 4 shown above and the specific compounds in Tables 5 and 6 below. Additionally, the processes described herein may be used to produce known compounds. Specifically, the processes are useful for preparing the compounds disclosed in WO 95/35308, WO 99/47545, WO 04/058718, WO 04/002961, WO 04/106304, WO 03/088917, WO 03/068242, WO 03/042169, WO 98/16505, WO 93/09135, WO 00/55114, WO 00/55127, WO 00/61542, WO 01/05772, WO 01/10383, WO 01/16093, WO 01/42216, WO 01/72707, WO 01/90070, WO 01/94351, WO 02/094263, WO 01/81331, WO 02/42278, WO 03/106460, WO 03/103677, WO 03/104231, U.S. Pat. Nos. 6,184,210, 6,184,244, 6,187,771, 6,197,750, 6,242,422, 6,235,899, April 2001 American Chemical Society (ACS) meeting in San Diego, Calif., USA, WO 02/22611, US2002/0058630, WO 02/085899, WO 95/35308, U.S. Pat. No. 5,716,929, WO 97/22619, U.S. Pat. No. 6,204,261, WO 99/47545, and WO 01/90063, all of which, as set forth herein, are incorporated herein by reference. Preferred compounds for use in accordance with this invention are described in WO 04/058718, WO 04/002961, WO 95/35308, U.S. Pat. No. 5,716,929, WO 97/22619, U.S. Pat. No. 6,204,261, WO 99/47545, and WO 01/90063, all of which, as set forth herein, are incorporated herein by reference.

TABLE 5

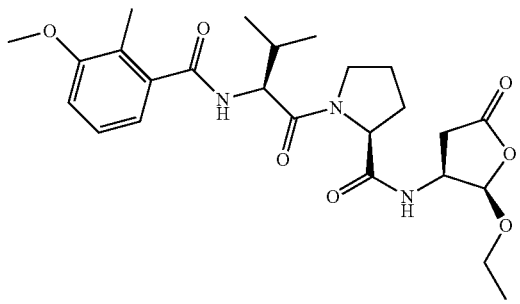

I-1

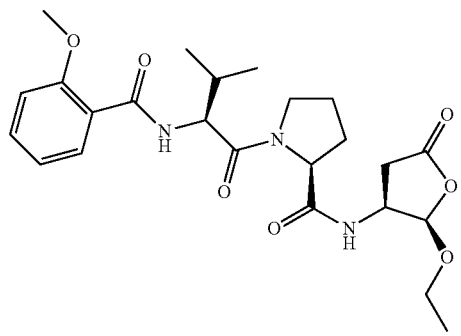

I-2

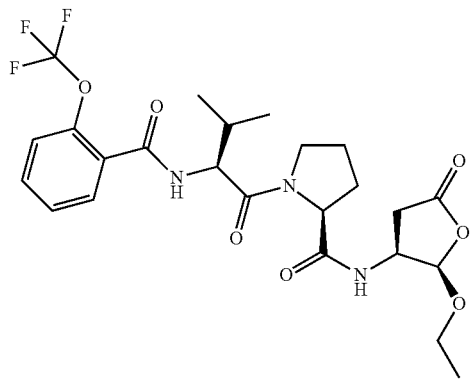

I-3

TABLE 5-continued

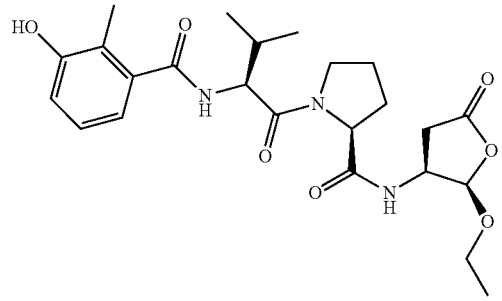

I-4

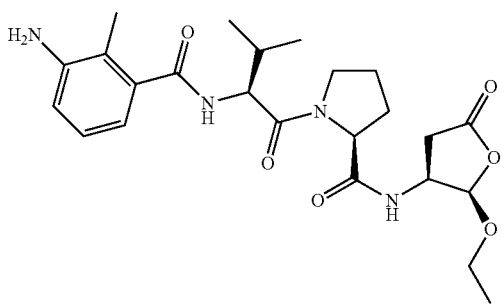

I-5

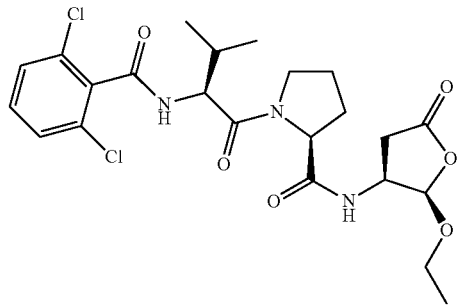

I-6

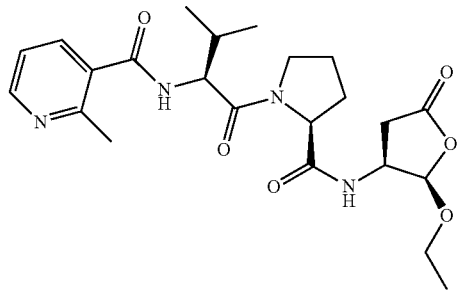

I-7

TABLE 5-continued
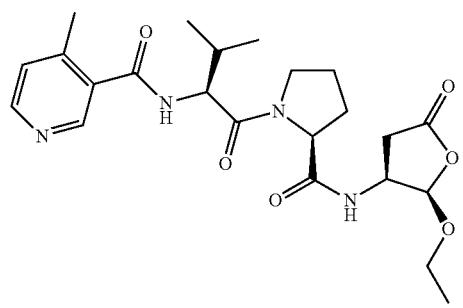
I-8
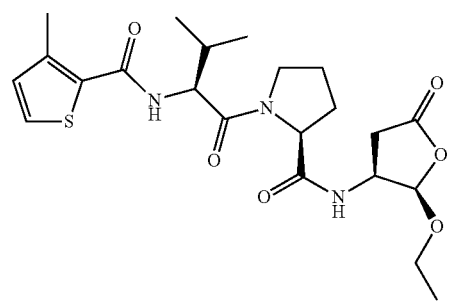
I-9
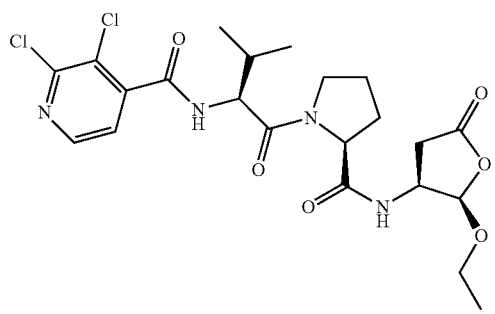
I-10
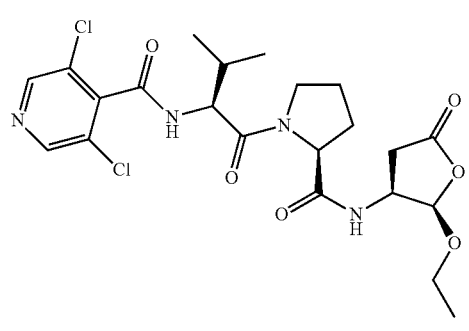
I-11
TABLE 5-continued
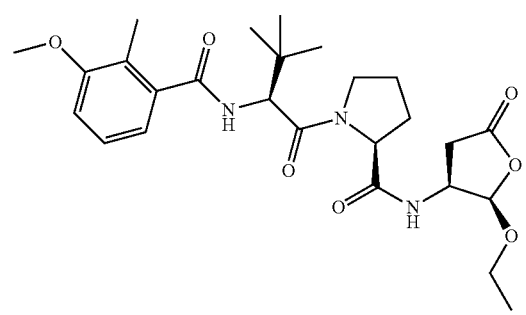
I-12
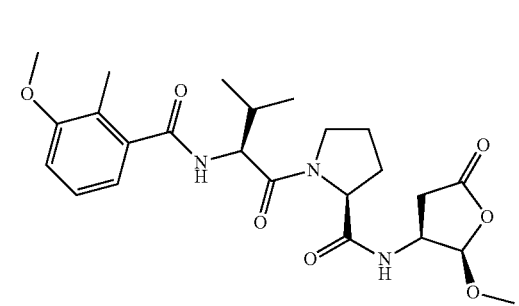
I-13
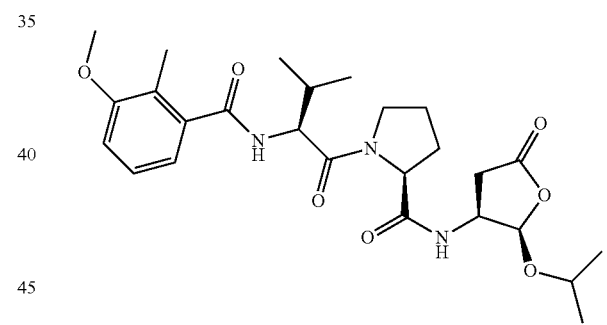
I-14
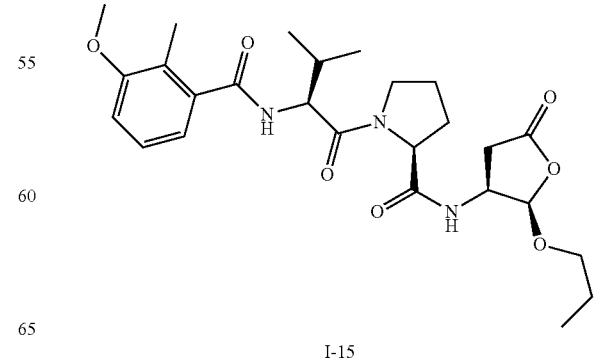
I-15

TABLE 5-continued
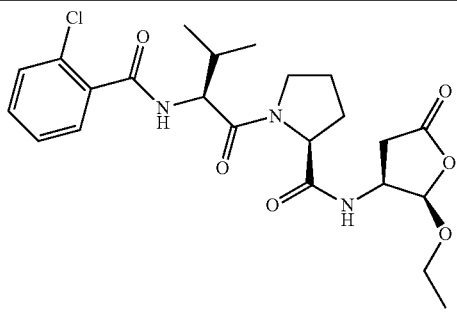
I-16
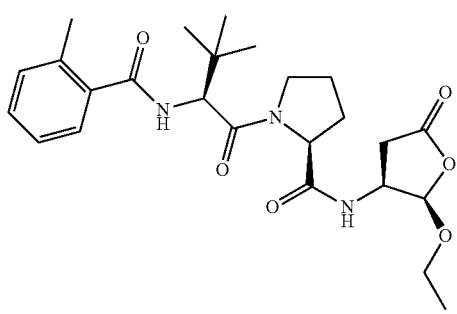
I-17
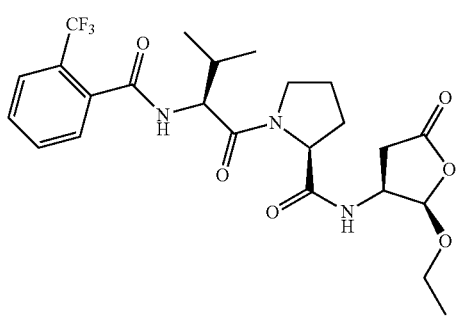
I-18
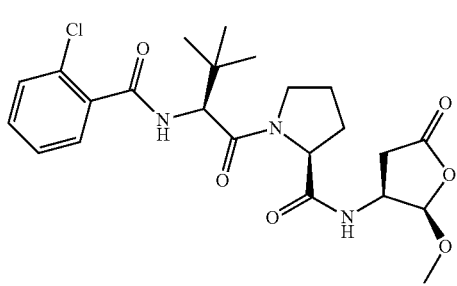
I-19
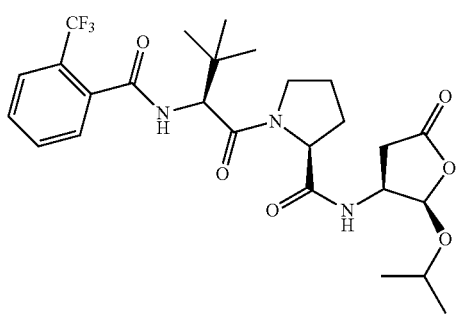
I-20
TABLE 5-continued
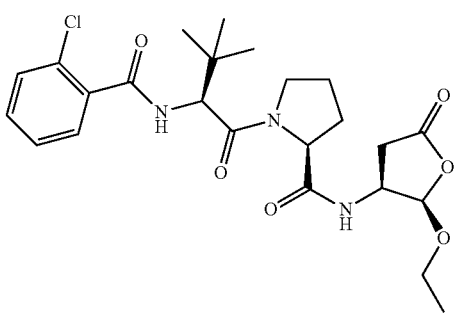
I-21
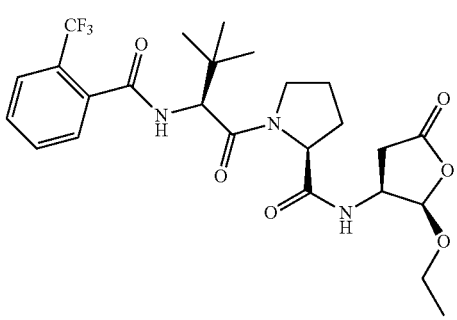
I-22
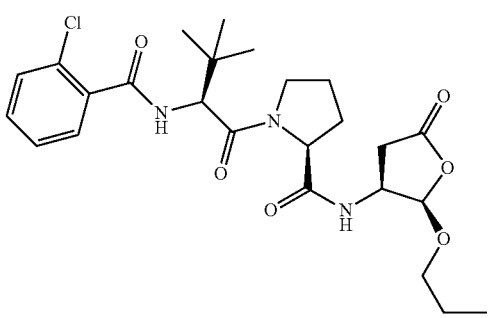
I-23
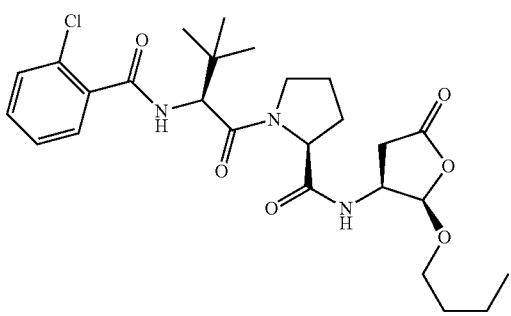
I-24

TABLE 5-continued
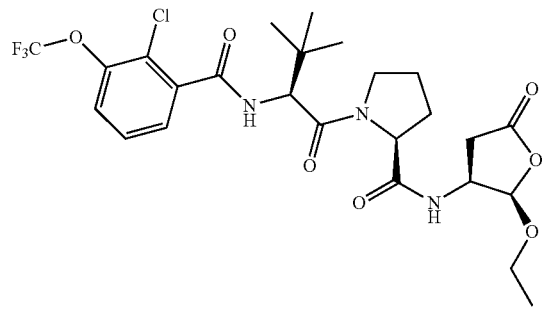
I-25
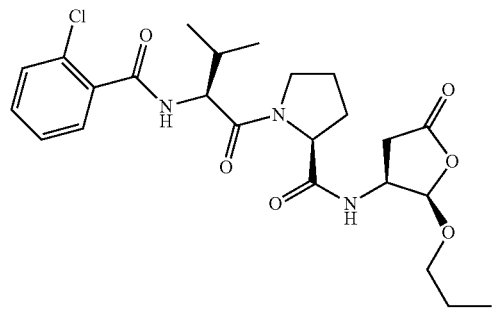
I-26
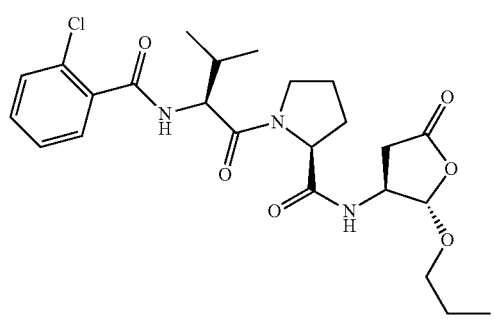
I-27
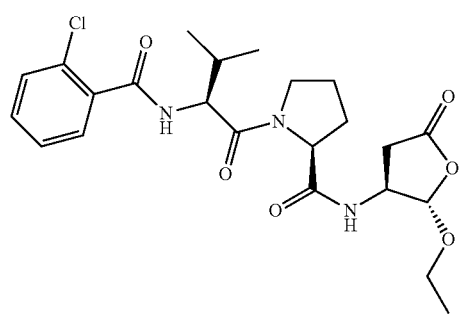
I-28
TABLE 5-continued
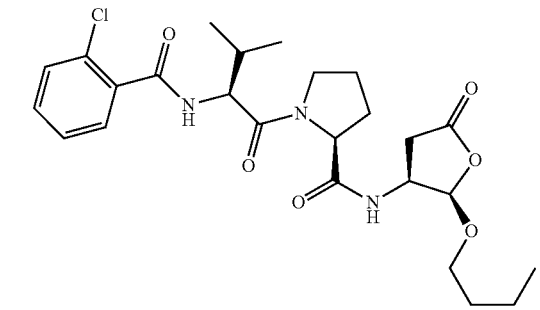
I-29
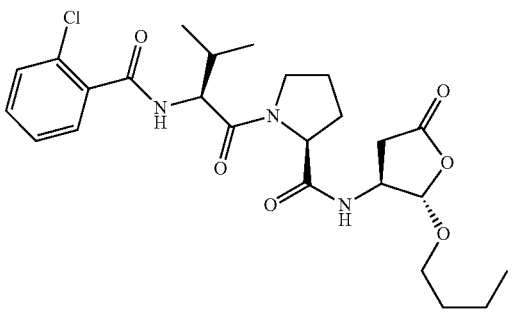
I-30
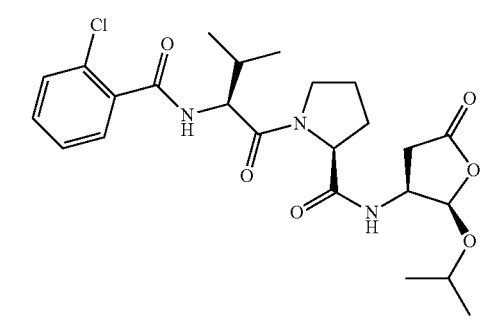
I-31
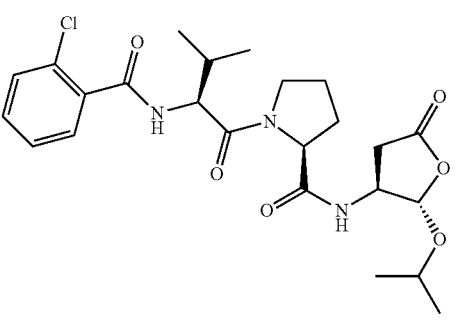
I-32

TABLE 5-continued
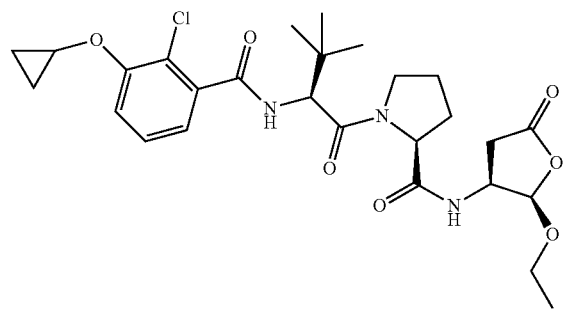
I-33
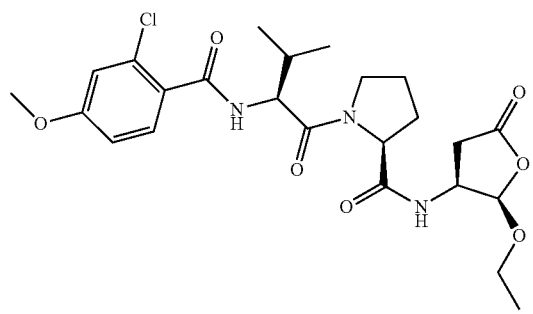
I-37
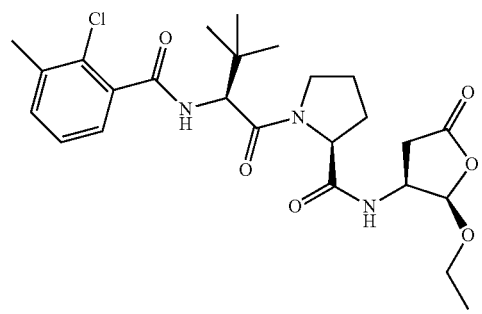
I-34
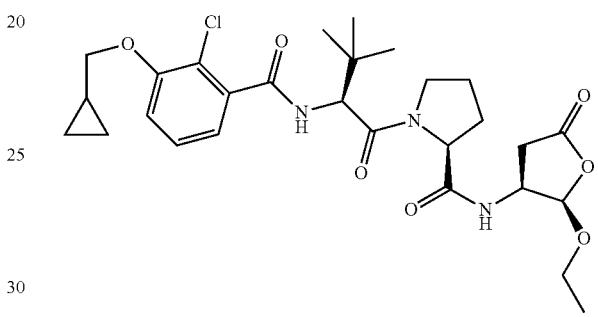
I-38
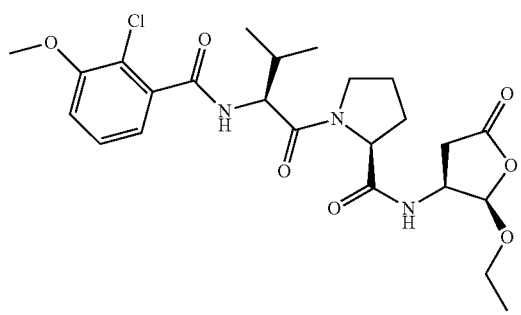
I-35
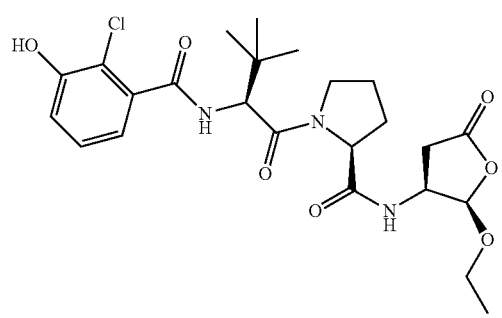
I-39
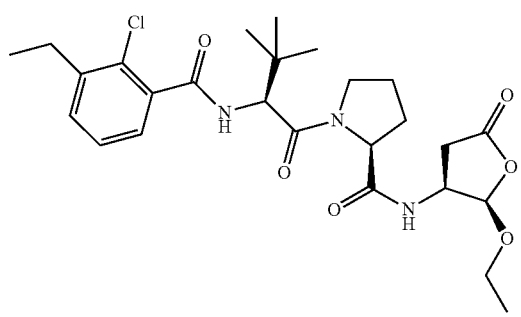
I-36
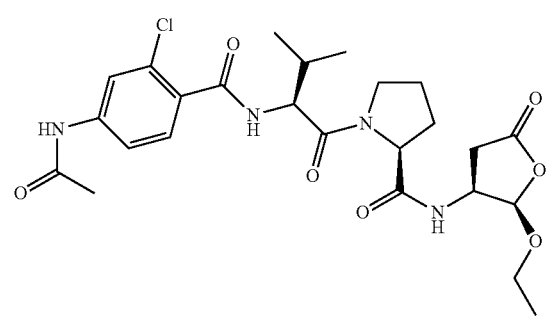
I-40

TABLE 5-continued
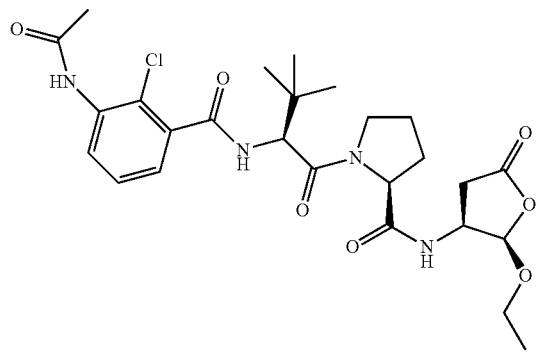
I-41
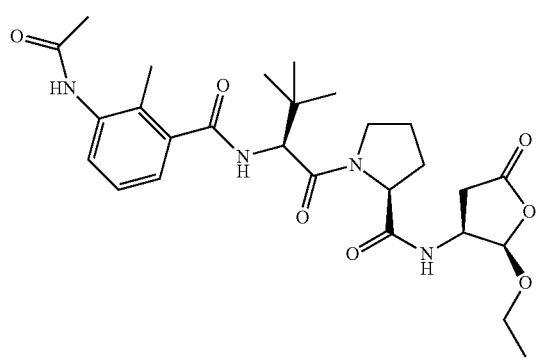
I-42
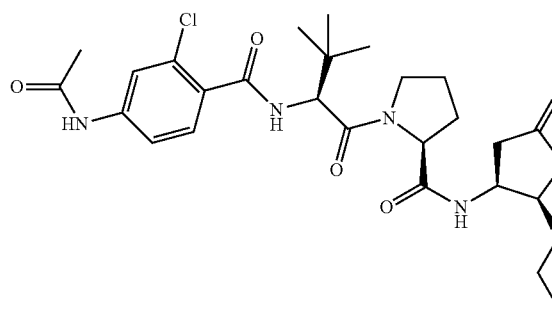
I-43
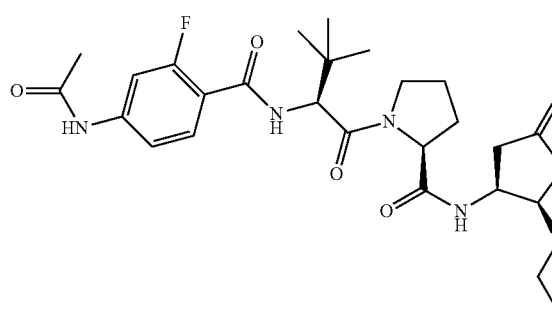
I-44
TABLE 5-continued
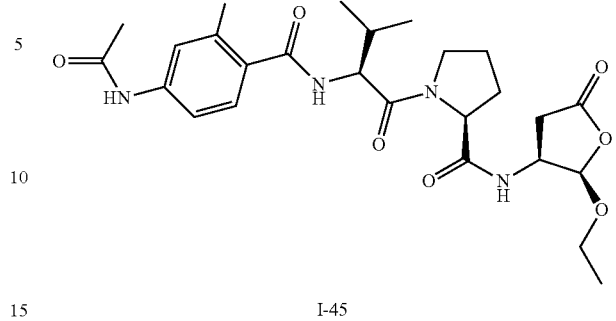
I-45
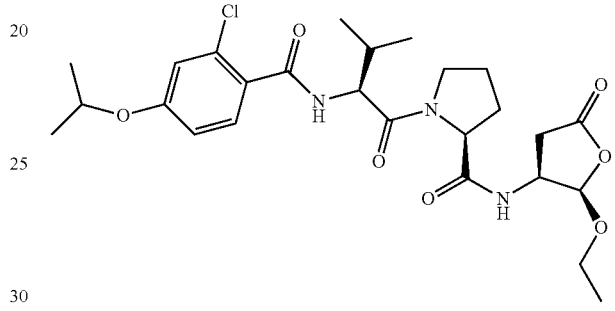
I-46
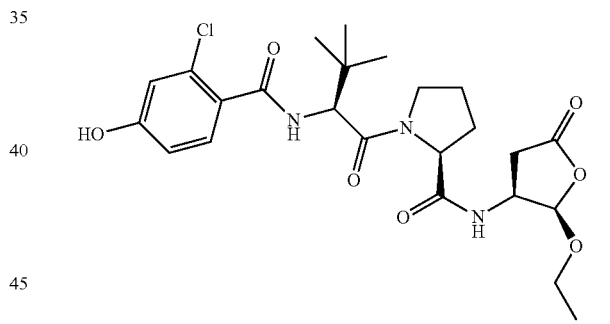
I-47
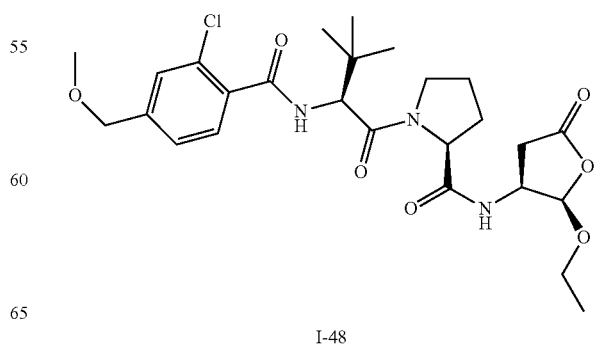
I-48

TABLE 5-continued
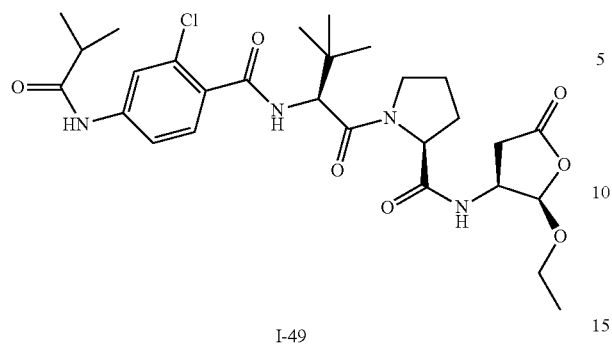
I-49
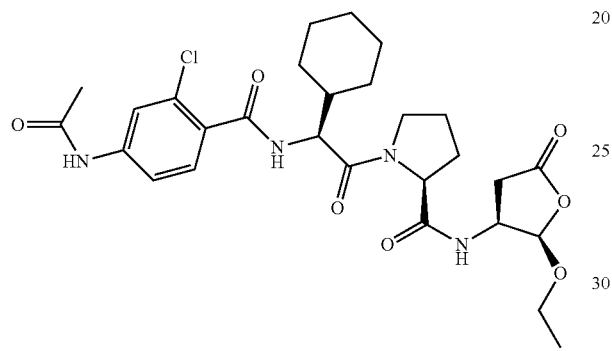
I-50
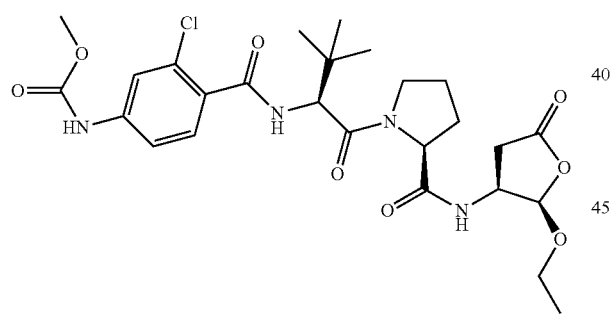
I-51
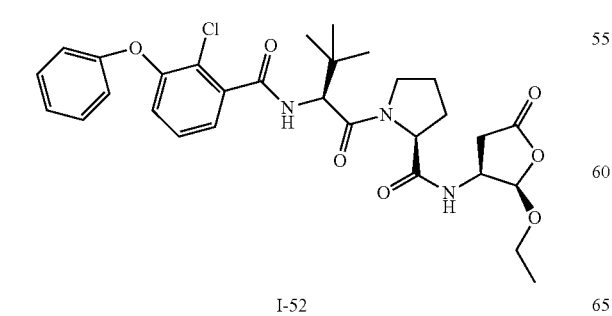
I-52
TABLE 5-continued
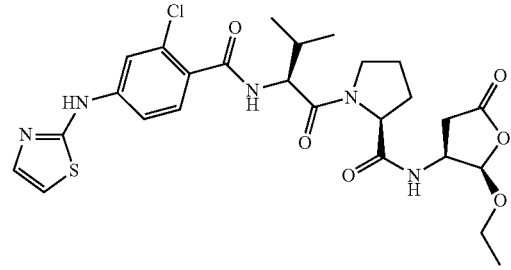
I-53
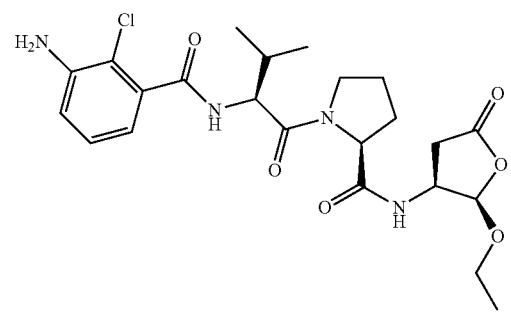
I-54
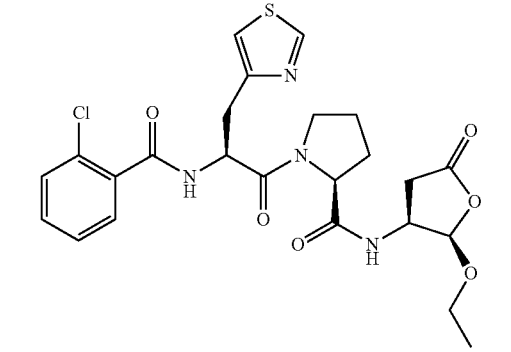
I-55
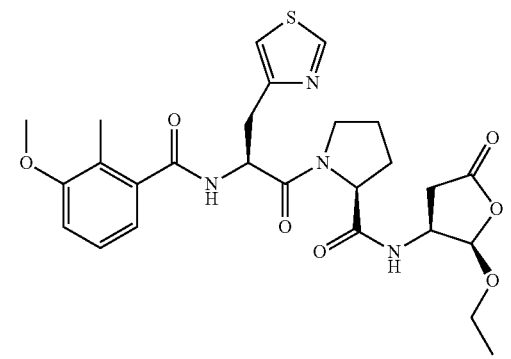
I-56

TABLE 5-continued
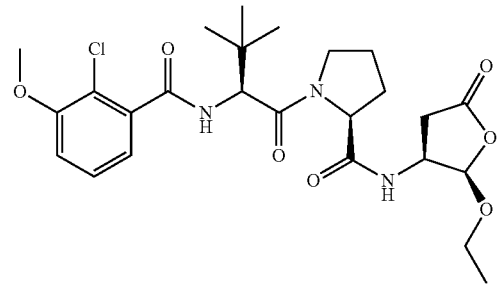
I-57
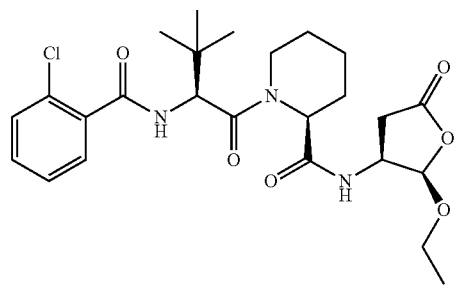
I-58
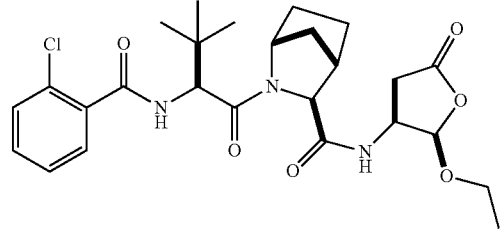
I-60
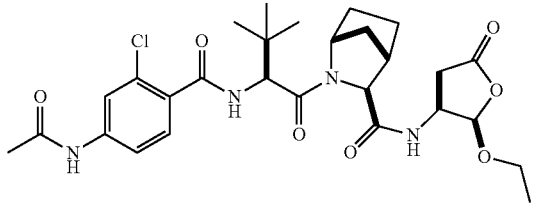
I-61
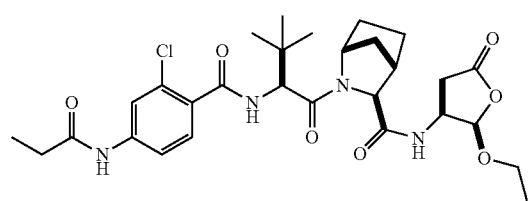
I-62
TABLE 5-continued
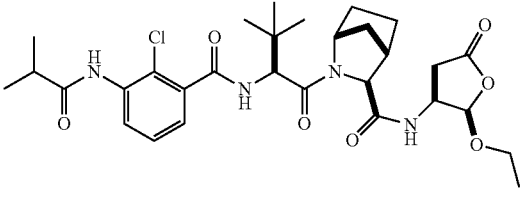
I-63
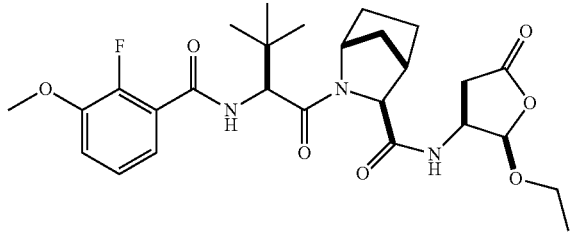
I-64
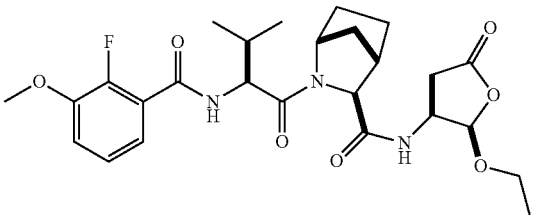
I-65
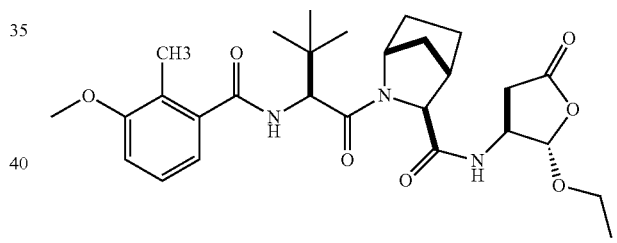
I-66
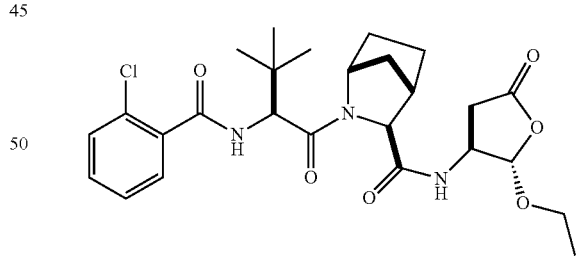
I-67
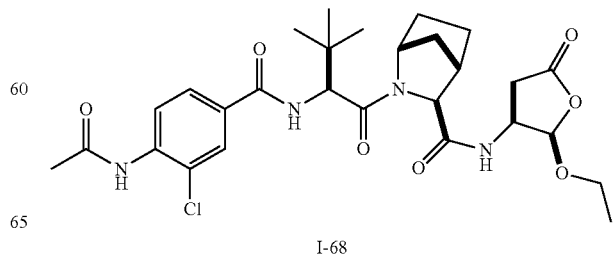
I-68

TABLE 5-continued
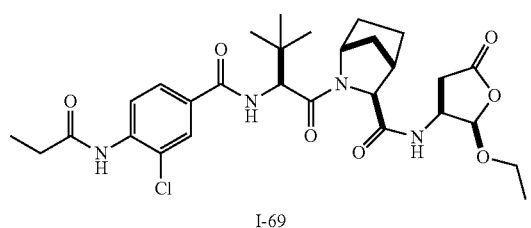
I-69
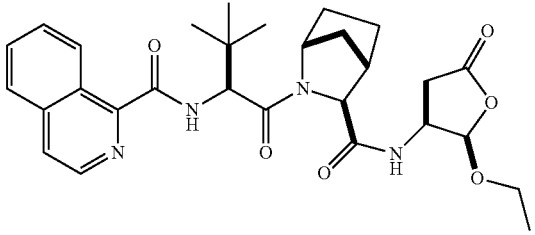
I-70
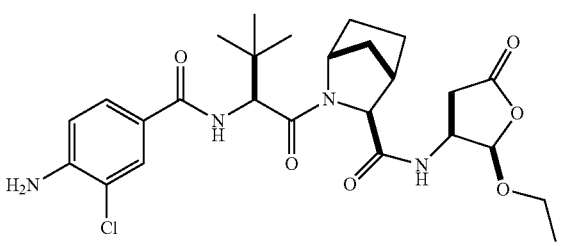
I-71
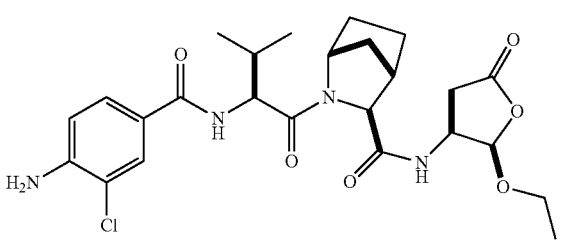
I-72
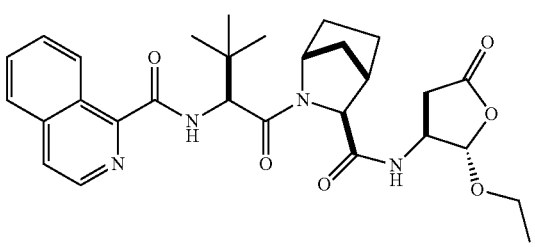
I-73
TABLE 6
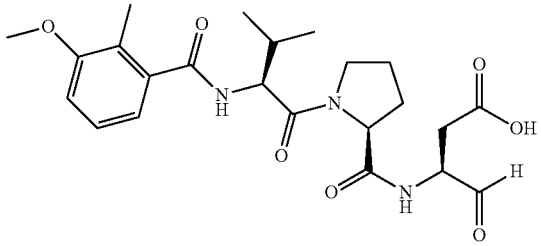
II-1
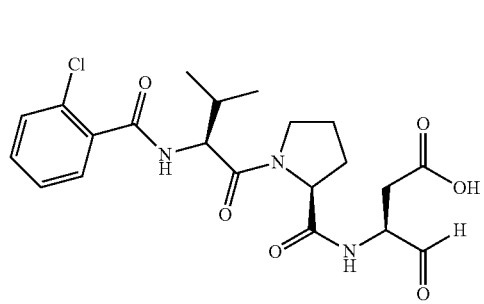
II-2
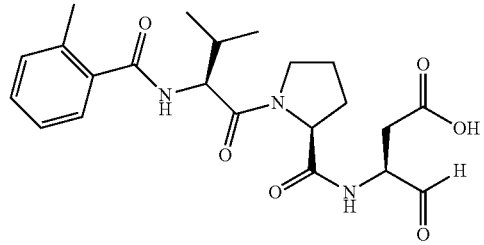
II-3
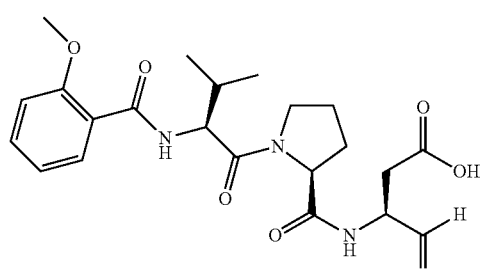
II-4
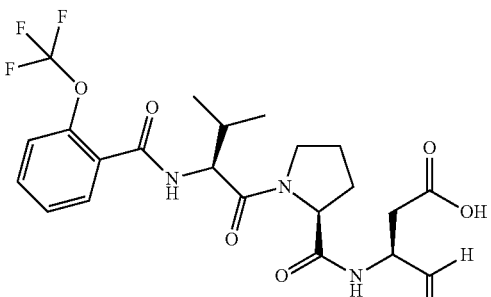
II-5

TABLE 6-continued
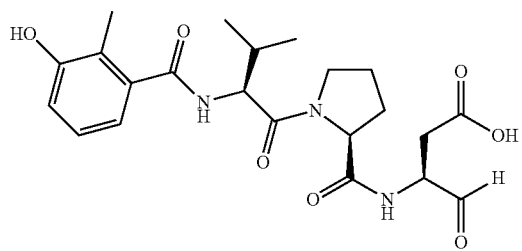
II-6
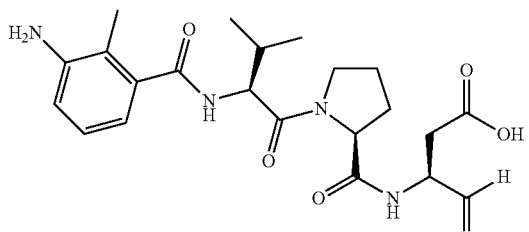
II-7
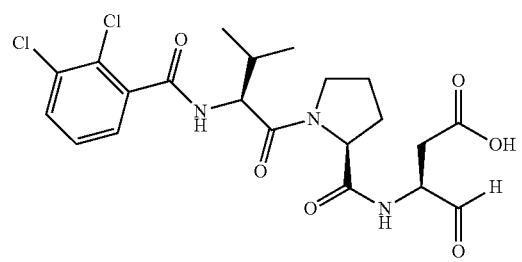
II-8
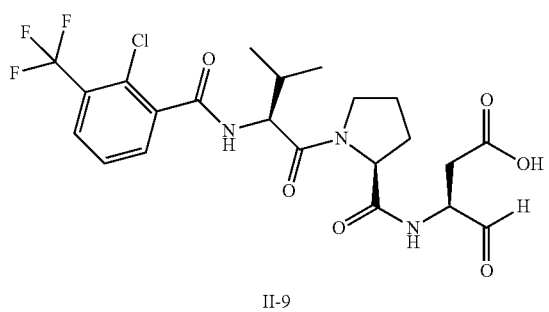
II-9
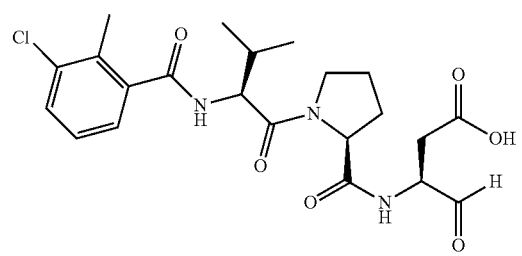
II-10
TABLE 6-continued
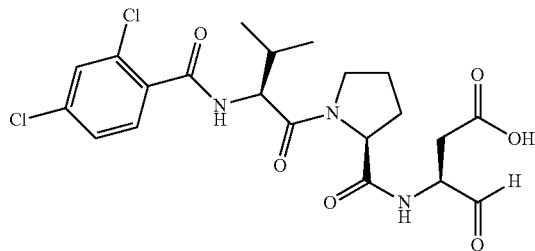
II-11
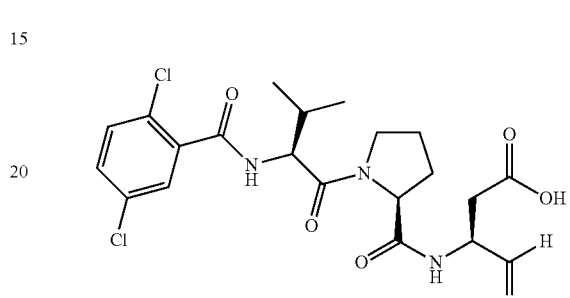
II-12
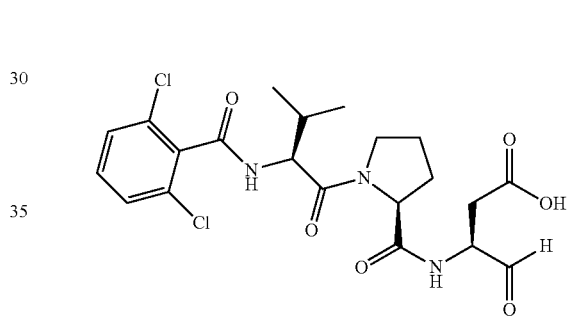
II-13
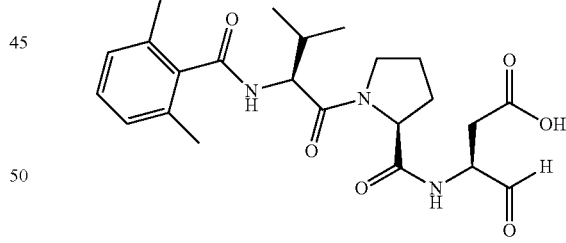
II-14
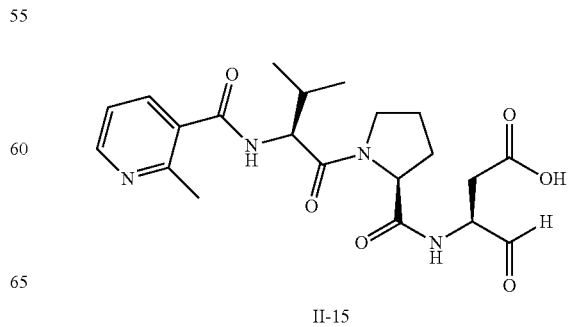
II-15

TABLE 6-continued
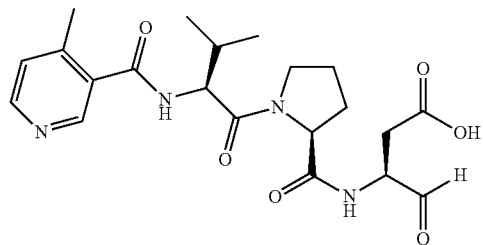
II-16
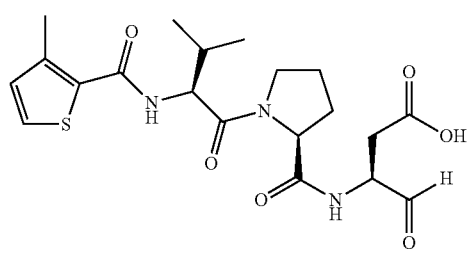
II-17
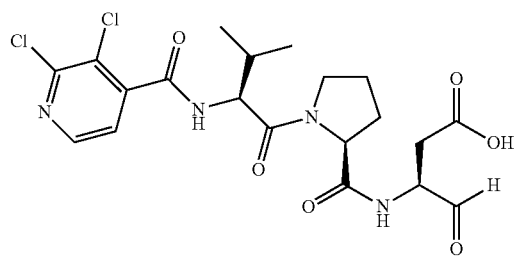
II-18
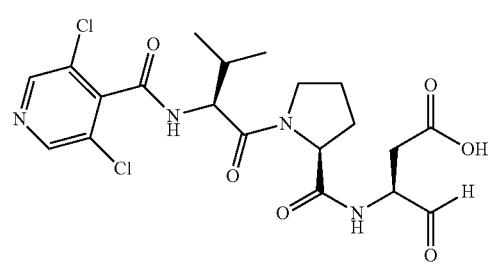
II-19
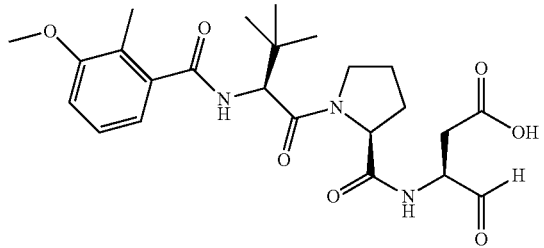
II-20
TABLE 6-continued
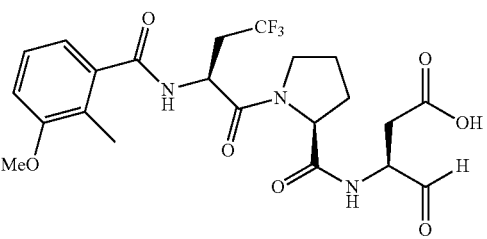
II-21
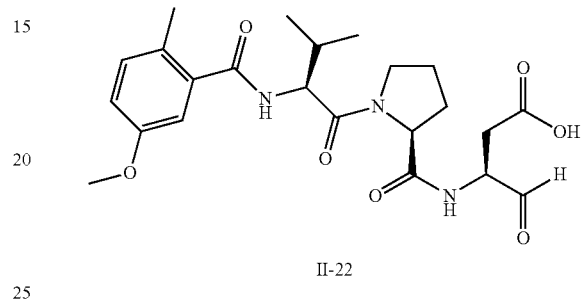
II-22
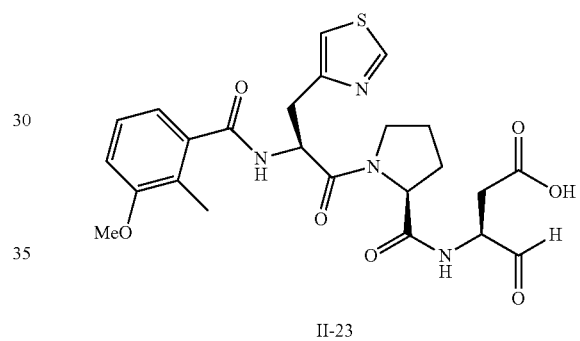
II-23
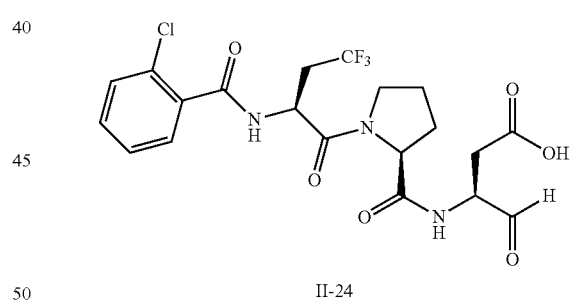
II-24
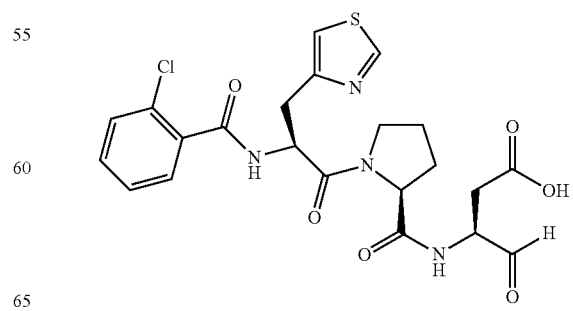
II-25

TABLE 6-continued
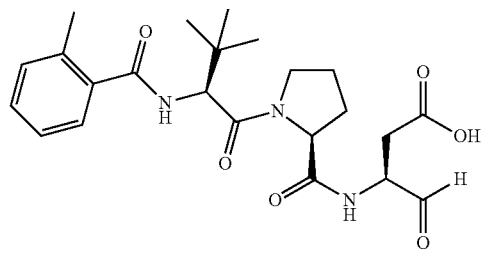
II-26
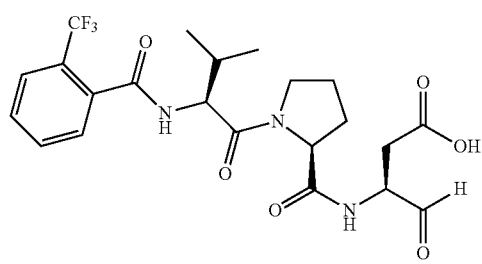
II-27
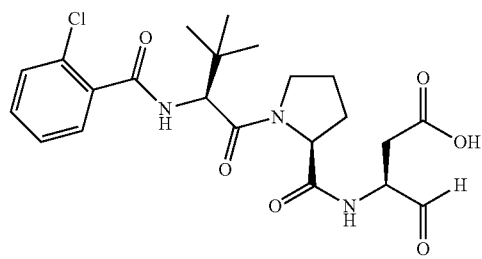
II-28
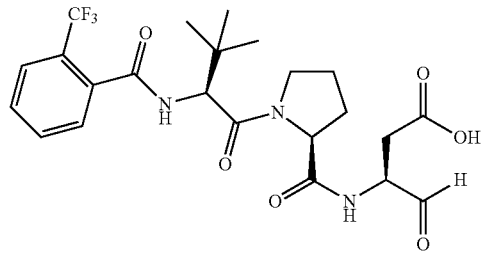
II-29
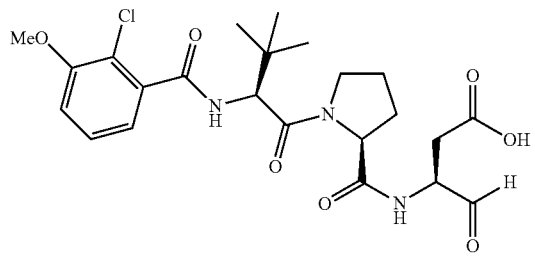
II-30
TABLE 6-continued
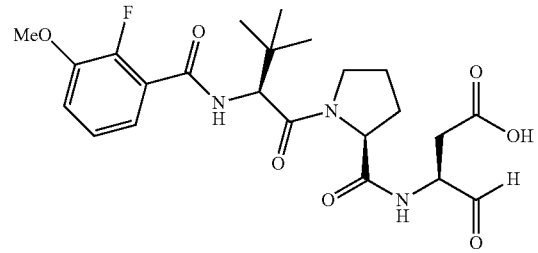
II-31
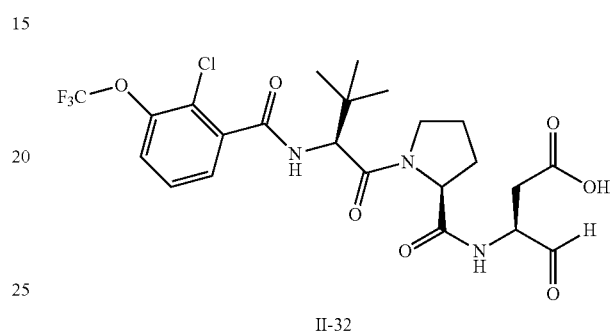
II-32
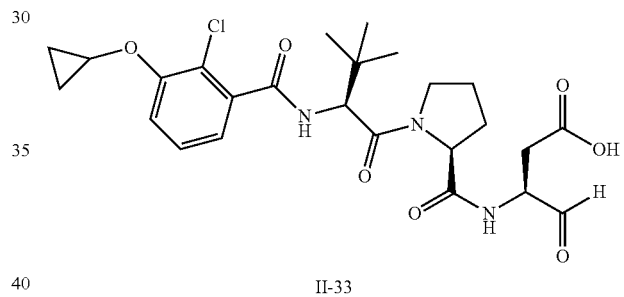
II-33
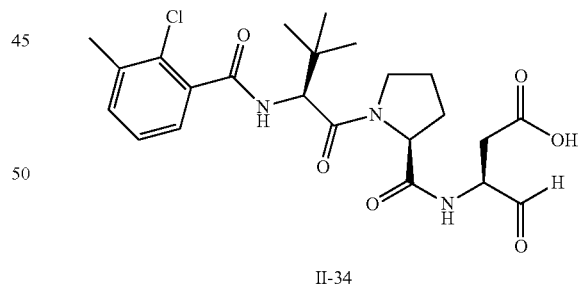
II-34
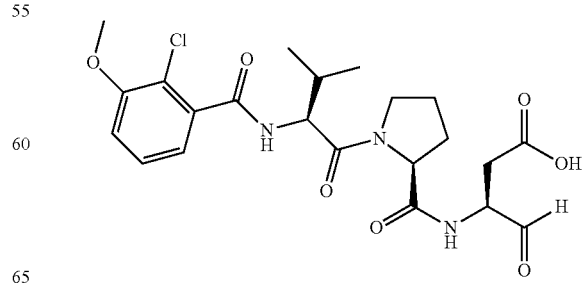
II-35

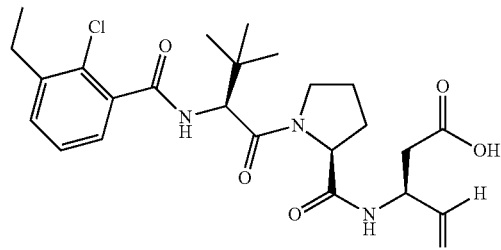
II-36
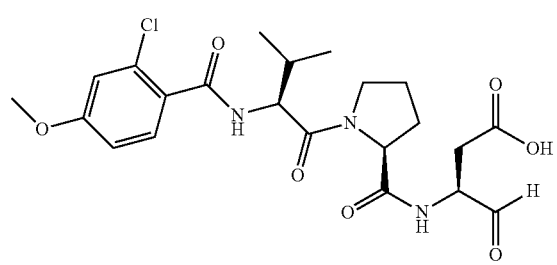
II-37
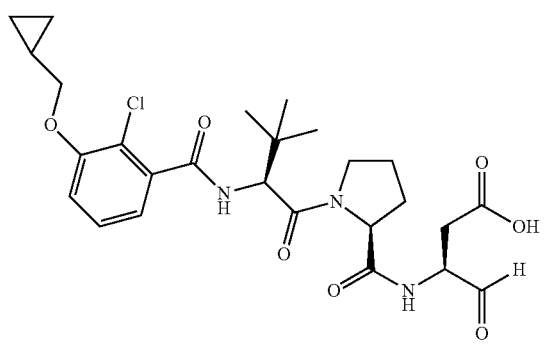
II-38
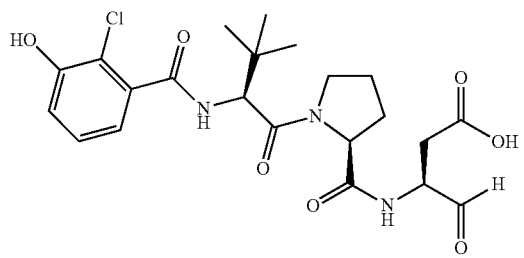
II-39
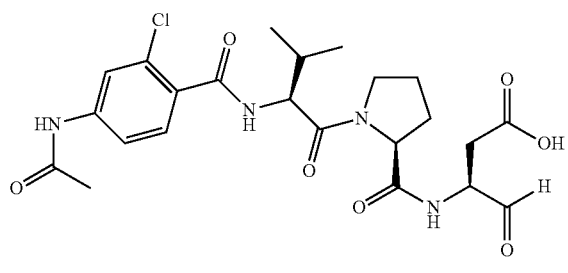
II-40
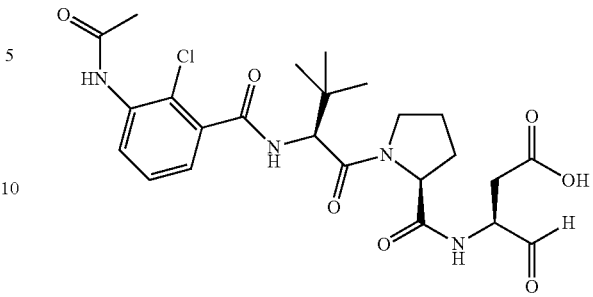
II-41
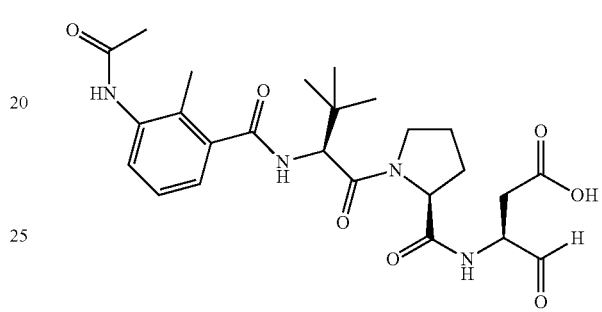
II-42
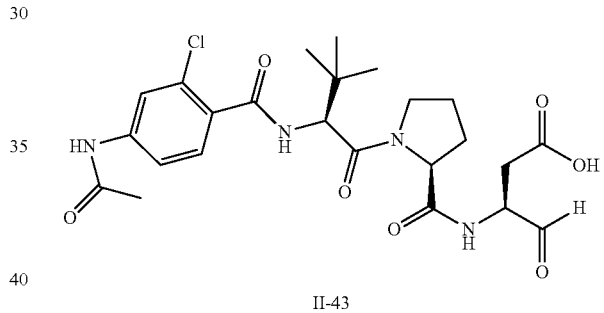
II-43
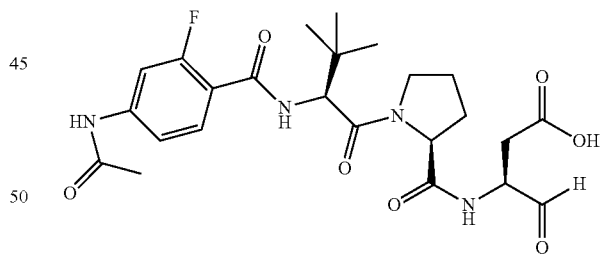
II-44
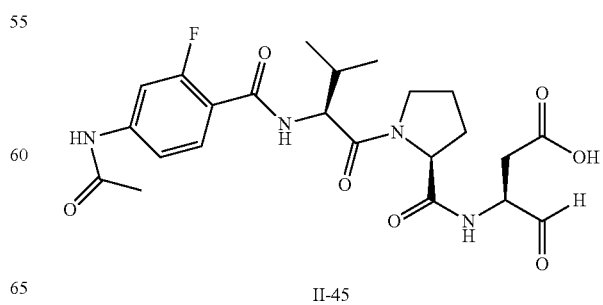
II-45

TABLE 6-continued
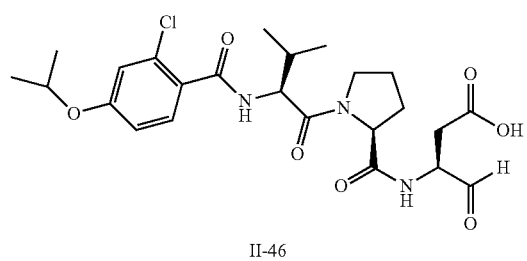
II-46
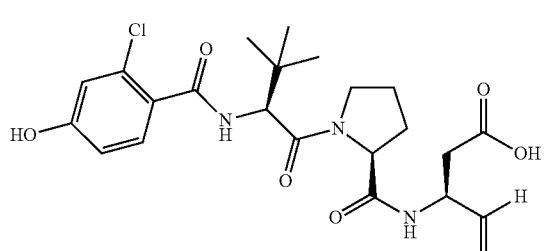
II-47
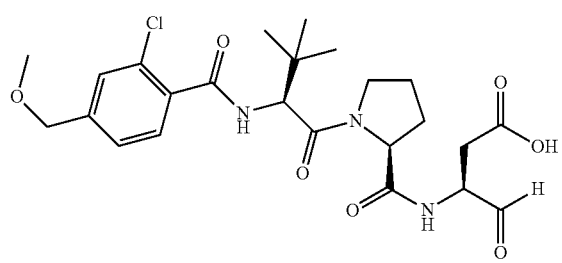
II-48
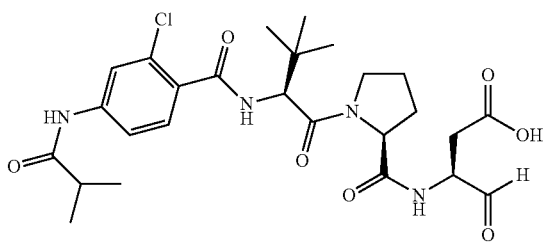
II-49
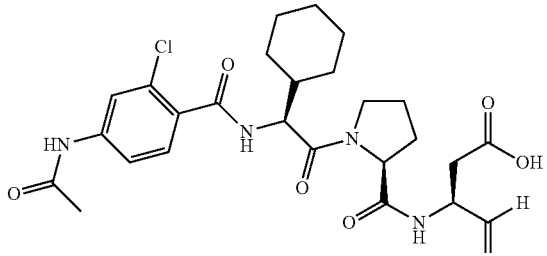
II-50
TABLE 6-continued
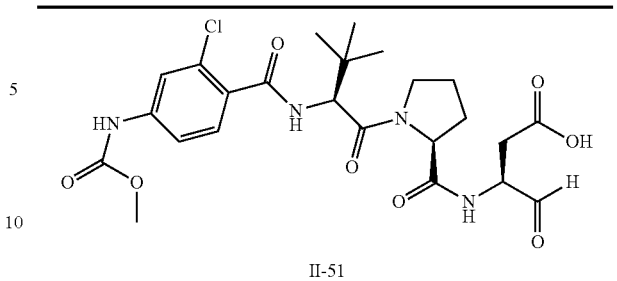
II-51
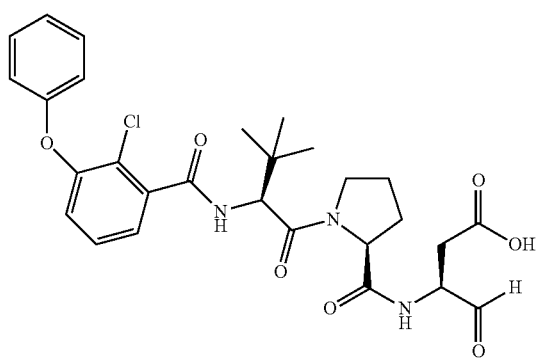
II-52
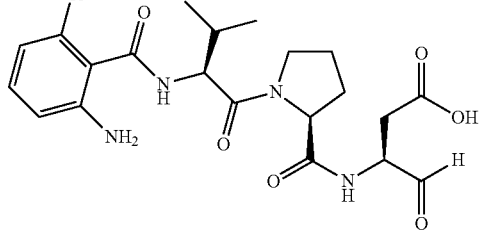
II-53
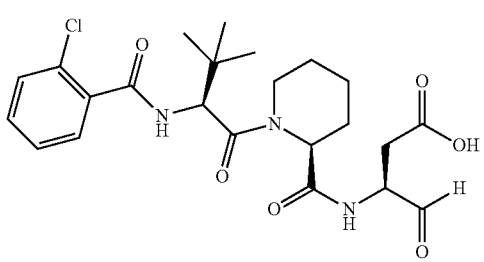
II-54
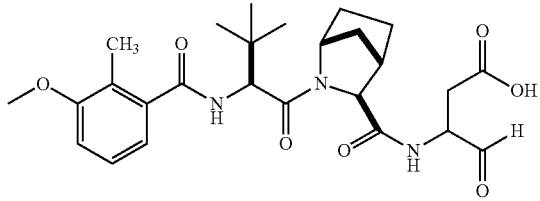
II-55

TABLE 6-continued

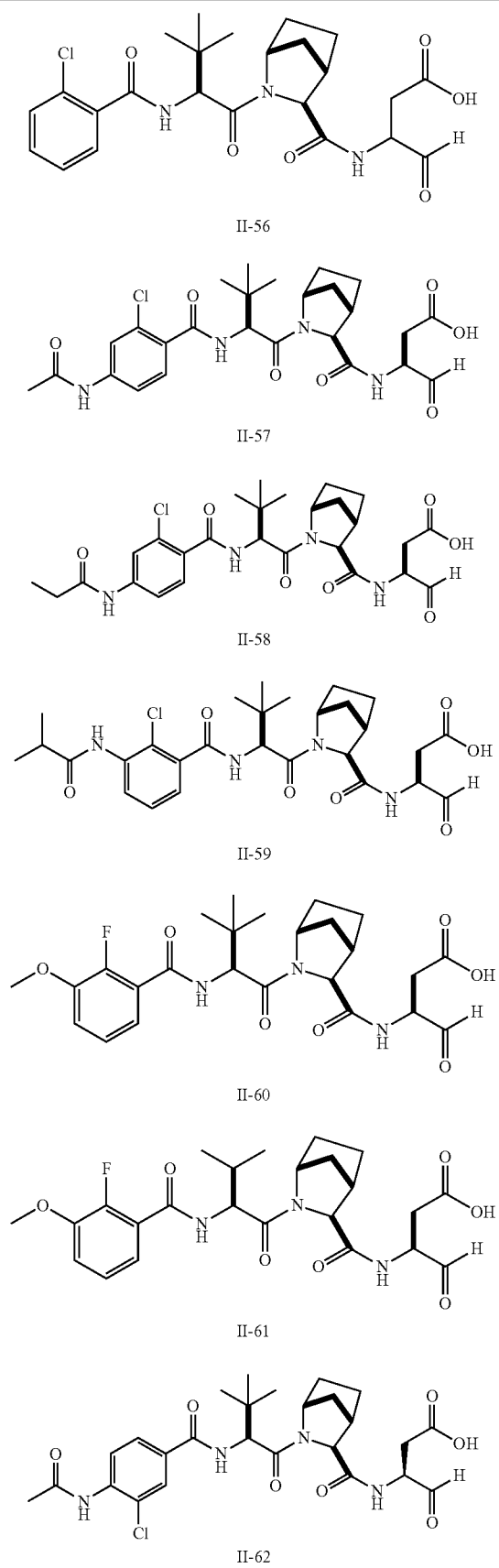

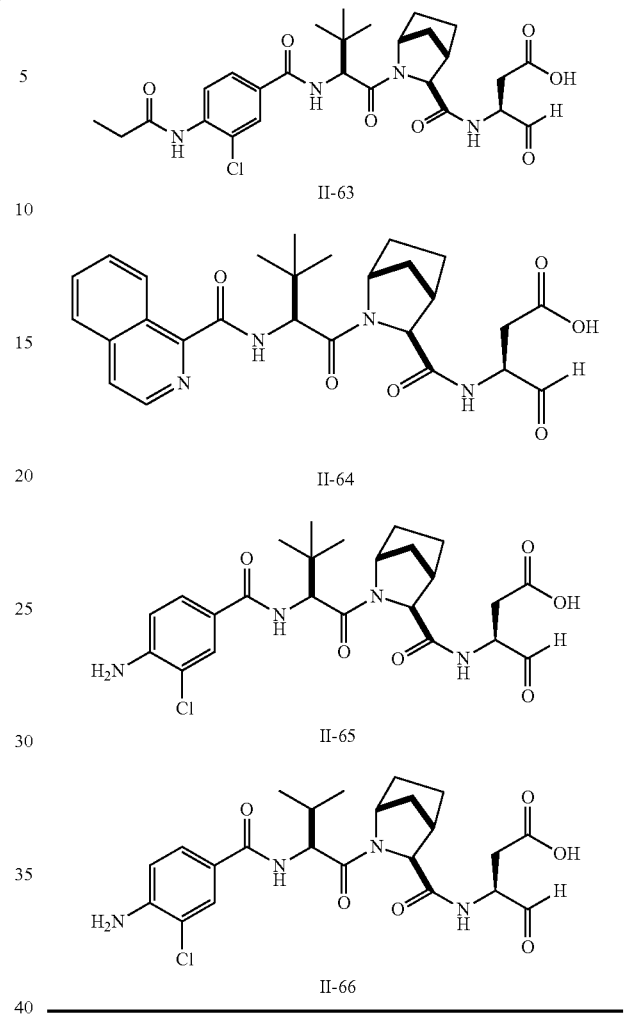

In order that this invention be more fully understood, the following preparative examples are set forth. These examples are for the purpose of illustration only and are not to be construed as limiting the scope of the invention in any way.

EXAMPLES

The abbreviations used herein are known to skilled practitioners. Scheme 1 the syntheses that are exemplified below.

Scheme 2. Synthetic Examples

STEP 1

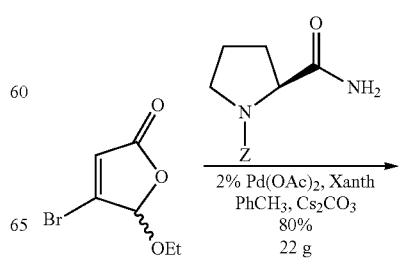

-continued

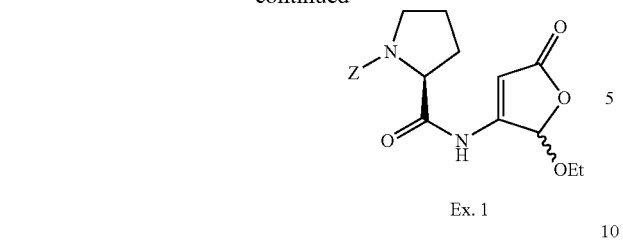

Ex. 1

STEP 2

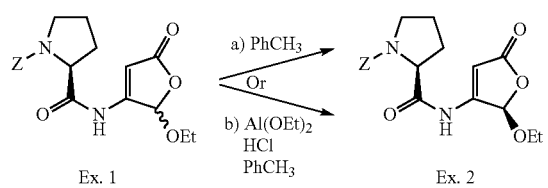

STEP 3

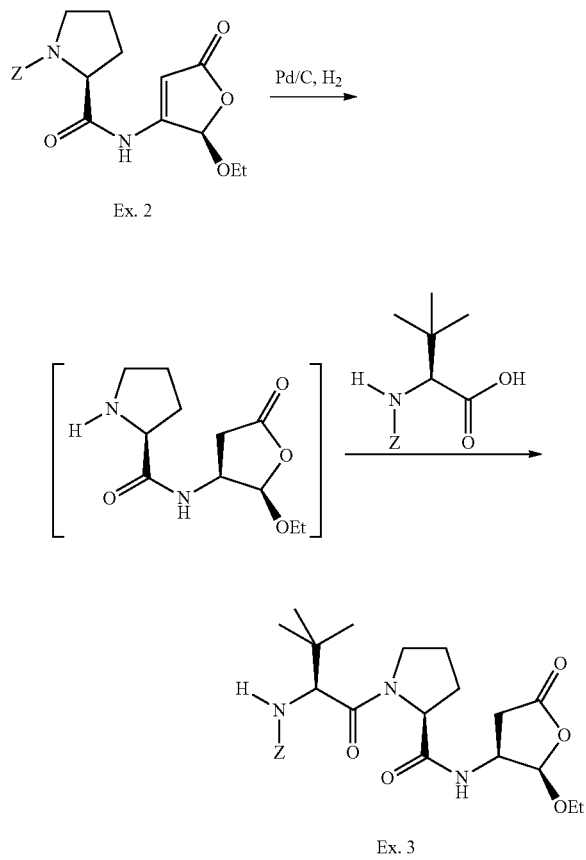

Ex. 2

Ex. 3

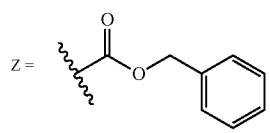

Example 1

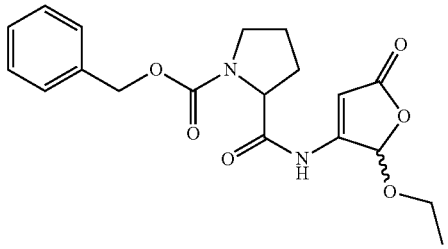

1

Preparation of 4-bromo-5-ethoxy-5H-furan-2-one

This procedure may be carried out in a manner similar to that described by C. Escobar, et al., *Ann. Quim.* (1971), 67, 43-57.). To a solution of 5-ethoxy-5H-furan-2-one (II, $R^1$=Et) (10.0 g, 78.0 mmol) in carbon tetrachloride (50 mL) at 0° C. is added over 0.5 h a solution of bromine (4.05 mL, 78.2 mmol) in carbon tetrachloride (25 mL). The reaction is stirred 1 h at 0° C., then 2 h at room temperature. The solvents are removed under reduced pressure and the residue was short-path distilled at pump vacuum (about 0.5 mm). The fraction collected at 100° C.-120° C. provided 4-bromo-5-ethoxy-5H-furan-2-one (13.2 g, 82% yield) as a yellow oil. $^1$H-NMR (500 MHz, CDCl$_3$) δ 6.24 (s, 1H), 5.63 (s, 1H), 3.71 (m, 1H), 3.63 (m, 1H), 1.14 (t, J=7.1 Hz, 3H) ppm.

Pd-Catalyzed Coupling of CBZ-Pro-NH$_2$ and Bromoethoxyfuranone

To a 1 L round bottom flask, CBZ-Pro-NH$_2$ (20 g, 80.4 mmol), Pd(OAc)$_2$ (0.36 g, 1.6 mmol), XANTPHOS (1.4 g, 2.4 mmol) was charged. The system was purged with nitrogen gas for 10 min. Toluene was added (200 mL), and the reaction was stirred with warming to 50° C. After reaching 50° C., the reaction was stirred for 30 min. The mixture changed from a yellow slurry to a brick-red solution as the amide dissolved and the (XANTPHOS)Pd(OAc)$_2$ complex formed. A solution of K$_2$CO$_3$ (26.6 g, 192 mmol) in water (200 mL) was added and the reaction was allowed to warm to 50 C.

To a beaker, bromoethoxyfuranone (18.3 g, 88.4 mmol) and toluene (30 mL) was charged. The reaction is stirred until a solution is formed (slight warming may be necessary because the dissolution is endothermic). The solution of the bromide is added slowly to the catalyst/amide solution at 50° C. over 3-3.5 hr. After the addition was complete, stirring of the reaction mixture was continued at 50° C. for 4 hours. While still at 50° C., the phases were separated and the aqueous phase discarded. The organic phase was washed with water (100 mL) at 50° C. The phases were separated and the aqueous phase discarded. The organic phase was concentrated to ½ volume and cooled to ambient temperature. Seeds were added (50 mg) if crystallization has not begun. The mixture was stirred at ambient temperature for 15 hr (overnight), cooled to 0° C. and stirred for 3-5 hr. The solid was filtered and rinsed with cold toluene. The solid was dried in vacuo at 40-50° C. to give a white crystalline solid (10.8 g, 36% yield).

In an alternative synthesis, a flask was charged with Pd$_2$(dba)$_3$ (4.18 g, 4.6 mmol), Xantphos (7.90 g, 13.7 mmol), CBZ-Proline amide (50 g, 201 mmol), Cs$_2$CO$_3$ (65.5 g, 201 mmol) and toluene (770 mL). The mixture was stirred at 35° C. for 30 min, to give a brown/yellow mixture.

Bromoethoxyfuranone (41.7 g, 201 mmol) as a solution in 30 mL toluene was added to the brown/yellow mixture. The solution was warmed to 80° C. After 15 min, HPLC analysis showed 90% reaction complete (comparing CBZ-proline amide and product), and no bromoethoxyfuranone remained. Another 4.1 g of bromoethoxyfuranone was added to the reaction mixture at 85° C. After stirring for 30 min, HPLC analysis showed 97% reaction completion. Another 2.8 g of bromoethoxyfuranone was added. After stirring for 45 min, HPLC analysis showed no CBZ-proline amide remaining. The mixture was cooled to 20-25° C., and water (200 mL) was added, followed by saturated aqueous sodium hydrogen sulfate (400 mL). Gas evolution was observed. The phases were separated and the organic phase was washed with saturated aqueous sodium hydrogen sulfate, then water. The organic phase was dried over sodium sulfate, filtered, and the solvent was removed in vacuo. The resulting crude material was purified by flash chromatography (1:1 EtOAc:hexanes, then 3:1 EtOAc:hexanes) to give 55.7 g (74% yield) of the desired product as a light brown oil.

$^1$H-NMR (d$_6$-DMSO): δ 10.20 (s, 0.5 H); 10.00 (s, 0.5 H); 7.55 (br s, 5H); 6.35 (s, 1H); 5.85 (s, 0.5H); 5.70 (s, 0.5H); 5.30 (m, 2H); 4.60 (br s, 1H); 4.05 (m, 1H); 3.85 (m, 1H); 3.65 (m, 1H); 3.55 (m, 1H); 2.05 (m, 4H); 1.40 (m, 3H).

Example 2

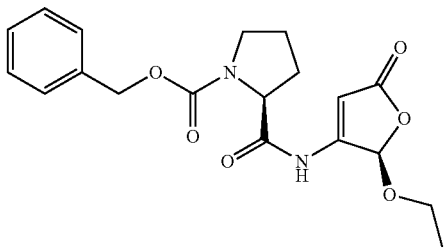

2

To a flask was charged the crude product produced as described above (37.36 g, 0.1 mol) and toluene (187 mL). The mixture was stirred to give a beige/brown solution. Seeds of compound 2 (226 mg) were added and the mixture was stirred at ambient temperature for 3 days, at 0-5° C. for 8 hr, then at ambient temperature for another 7 days. The solution was cooled again to 0-5° C. and stirred for 3 hr, filtered, and the solid was rinsed with toluene. The solid was dried in the air to give 5.61 g (15% yield) of the title compound as a 97:3 mixture of anomers.

$^1$H-NMR (d$_6$-DMSO): δ 7.35-7.25 (m, 5H); 5.75 (d, 1H); 5.70 (d, 1H); 5.1-4.9 (m, 2H); 4.35 (m, 1H); 3.70 (m, 1H); 3.60 (m, 1H); 3.40 (m, 2H); 2.15 (m, 1H) 1.80 (m, 2H); 1.20 (t, 1.5H); 1.10 (t, 1.5H)

Example 3

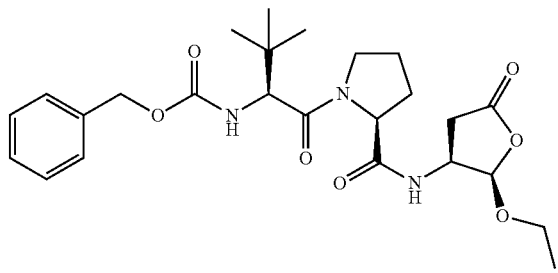

To a flask was charged the compound described in Example 2 (5.00 g, 13.3 mmol), 20% Pd(OH)$_2$/C (1.00 g, 50% wet), isopropyl acetate (30 mL), and DMF (10 mL). The mixture was hydrogenated under 50 psig H$_2$ at 0-5° C. for 5 hr, then at ambient temperature for 21 hr. HPLC analysis showed the reaction to be 97% complete. The mixture was filtered through celite and the solids were rinsed with a 3:1 isopropyl acetate:DMF solution to provide the unprotected compound of example 2.

To Cbz-t-leu-OH dicyclohexylamine salt was added isopropyl acetate (30 mL) and 1.0 M H$_2$SO$_4$ (30 mL). The mixture was agitated until two clear phases were obtained. The aqueous phase was discarded and the organic phase was washed with water (30 mL). The organic phase was collected. To the organic phase was added DMF (10 mL), then hydroxybenzotriazole (2.2 g, mmol). EDC (2.8 g) was added and the mixture was stirred for 1 hr. To this mixture was added the above hydrogenation solution. The mixture was stirred at ambient temperature for 8.5 hr. Water (100 mL) was added and the mixture was stirred for 1 hr. The phases were separated and the organic phase was washed with aqueous 0.5 M NaHSO$_4$, saturated aqueous sodium chloride, and water. The solution was concentrated to dryness to give 4.04 g (62% yield) of the title compound.

Alternatively, a 2 liter Parr pressure reactor was charged with 100.0 g (0.267 moles) a compound described in Example 2, and 10.0 g of 10% Pd/C (50% wet). The reactor was purged with nitrogen for 10 minutes. 800.0 mL of ethyl acetate, followed by 19.5 mL of trifluoroacetic acid were then added. The reactor was then closed, pressurized to 60 psi with hydrogen followed by venting. This cycling was repeated twice. The reaction was stirred for 2 hours under hydrogen (60 psi). The palladium catalyst was filtered through a pad of celite, and the filtrate was held at 4° C. until needed for the subsequent coupling step.

To a 3 liter, 3-neck round bottom flask equipped with mechanical stirring and a thermocouple was charged 43.3 g of 1-Hydroxybenzotriazole (anhydrous, 0.320 moles). To this flask was added a solution of Cbz-t-leucine (70.8 g in 430 mL of EtOAc). DMF (190 mL was charged to this suspension, and a clear light yellow solution was achieved. To this solution was charged 1-[3-(Dimethylamino)propyl]-3-ethylcarbodiimide hydrochloride (EDC, 56.3 g, 0.294 moles). A thin suspension formed, and was stirred for 2 hours at 22° C. To this suspension was charged the solution of the unprotected compound of example 2 (TFA salt). Triethylamine (112 mL, 0.801 moles) was added dropwise over 30 minutes, and the resulting suspension was stirred at 22° C. for 2 hours. Water (400 mL) was added, and the biphasic mixture was stirred for 12 hours at 22° C. This biphasic mixture was then transferred to a 4-liter separatory funnel, and the aqueous layer was removed. The organic layer was washed with 400 mL of saturated sodium bicarbonate solution followed by water (2×400 mL). The ethyl acetate was distilled under vacuum to a final volume of approximately 400 mL. To this crude solution was charged 200 mL of heptane, followed by seeding with 1.0 g of the compound of example 3. The cloudy suspension was then cooled to 5° C., which resulted in the formation of a thick slurry. Additional heptane was charged (400 mL) over a three hour period while maintaining the batch at 5° C. The solids were isolated by vacuum filtration, rinsing the filter cake with a 2:3 EtOAc/Heptane mixture (2×100 mL). The solids were dried for 12 hours in a vacuum oven at 22° C., with a nitrogen bleed (80% yield for 2 steps).

$^1$HNMR (CDCl$_3$) δ 7.5 (d, 1H, J=7.8 Hz); 7.4-7.3 (m, 5H); 5.5 (overlapping d, m, 2H, J=5.3 Hz); 5.1 (d, 1H, J=12.3 Hz); 5.1 (d, 1H, J=12.2 Hz); 4.7-4.6 (m, 2H); 4.4 (d, 1H, J=9.7 Hz); 3.9 (m, 1H); 3.8 (q, 1H, J=8.4 Hz); 3.7-3.6 (m, 2H); 2.8 (dd, 1H, J=17.2, 8.4 Hz); 2.4-2.3 (overlapping m, dd, 2H, J=17.2, 10.4 Hz); 2.1 (m, 1H); 2.0 (m, 1H); 1.9 (m, 1H); 1.3 (t, 3H, J=7.2 Hz); 1.0 (s, 9H).

Example 4

Scheme 3 and Synthetic Examples

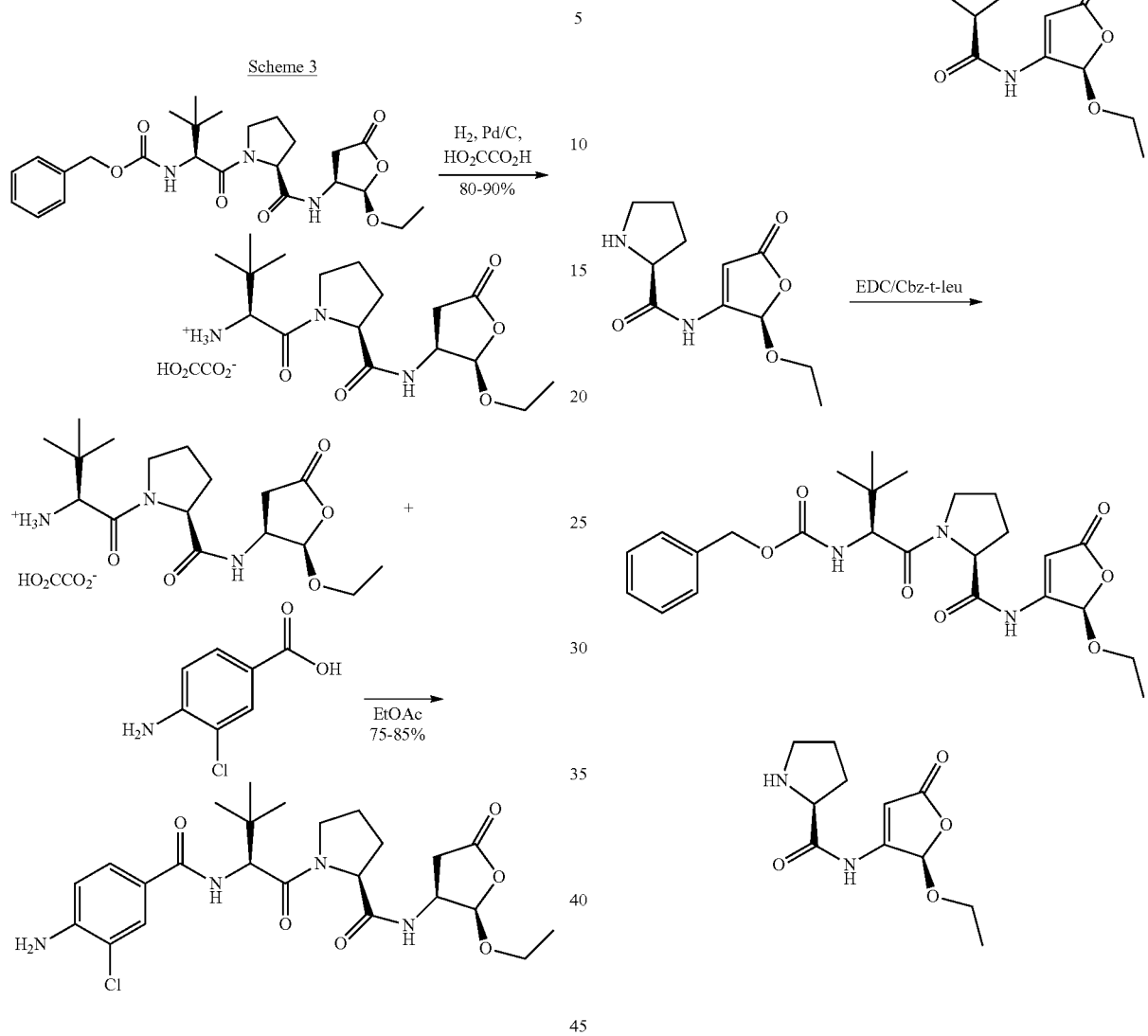

The compound described in Example 3 may be further modified by removing the protecting group and coupling additional moieties to the Leucine amine.

Example 4

Scheme 4 and Alternative Procedures

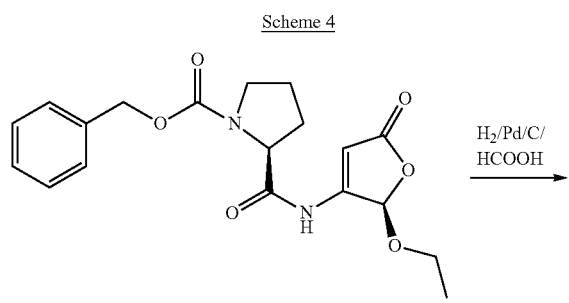

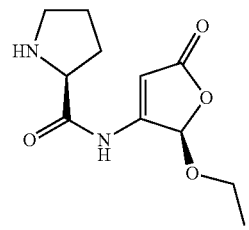

To a 1-liter, 3-neck round bottom flask equipped with mechanical stirring and a nitrogen inlet was charged 50.0 g of the compound of example 2 (0.134 moles), and 10.0 g of 10% Pd/C (50% wet). The vessel was purged with nitrogen for 10 minutes. Formic acid (500 mL) was added, and the suspension was stirred under nitrogen for 16 hours at 22° C. The reaction mixture was filtered through celite, and to the filtrate was added 20.6 mL of trifluoroacetic acid. The formic acid was distilled under vacuum, and the remaining formic acid was removed by azeotropic distillation with toluene. The crude oil that was obtained was dissolved in 150 mL of ethyl acetate, and methyl-tert-butyl ether (100 mL) was charged dropwise over 2 hours to crystallize the trifluoroacetate salt. The suspension was cooled to 5° C., and the solids were collected by vacuum filtration, rinsing with a 3:2 EtOAc/MTBE solution (2×50 mL) to furnish the desired product as a TFA salt in 55% yield.

$^1$HNMR (d$_6$-DMSO) δ 11.6 (br. s, 1H); 9.1 (br. s, 2H); 6.15 (s, 1H); 6.05 (s, 1H); 4.5 (m, 1H); 3.75 (m, 2H); 3.3 (m, 2H); 2.35 (m, 1H); 1.95 (m, 3H); 1.2 (t, 3H, J=6.7 Hz)

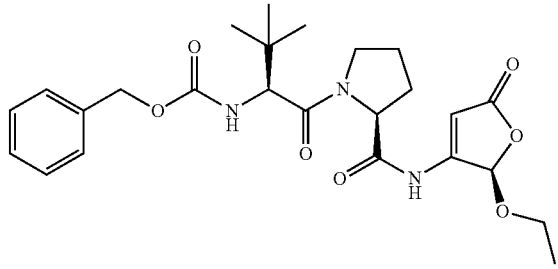

To a 1-liter, 3-neck round bottom flask equipped with mechanical stirring, addition funnel and nitrogen inlet was charged a solution of Z-tert-Leucine (20.6 g, 0.0776 moles) in dichloromethane (250 mL). Anhydrous 1-Hydroxybenzotriazole (10.5 g, 0.0776 moles) was added to this solution, followed by 14.9 g of 1-[3-(Dimethylamino)propyl]-3-ethylcarbodiimide (EDC, 0.0776 moles). A homogenous solution was achieved, and was stirred for 2 hours at 22° C. To this reaction was charged 25.0 g of the unprotected proline analog (TFA salt, 0.0706 moles), followed by 4-methylmorpholine (15.5 mL, 0.141 moles). The solution was stirred for 3 hours at 22° C. The reaction mixture was transferred to a separatory funnel, and washed with aqueous saturated sodium bicarbonate (100 mL), followed by a 10% aqueous solution of citric acid (100 mL). The organic layer was purified by silica gel chromatography (50% EtOAc/Hexane) to afford the desired product in 60% yield.

$^1$HNMR (d$_6$-DMSO) δ 11.0 (s, 1H); 7.35 (m, 5H); 7.25 (d, 1H); 6.0 (br. s, 2H); 5.1 (d(ab), 1H); 5.0 (d(ab), 1H); 4.5 (br. s, 1H); 4.2 (d, 1H); 3.8 (m, 3H); 3.65 (m, 1H); 2.15 (m, 1H); 1.9 (m, 2H); 1.8 (m, 1H); 1.2 (t, 3H); 1.0 (s, 9H).

Scheme 5 and Synthetic Examples

Scheme 5

STEP 1:

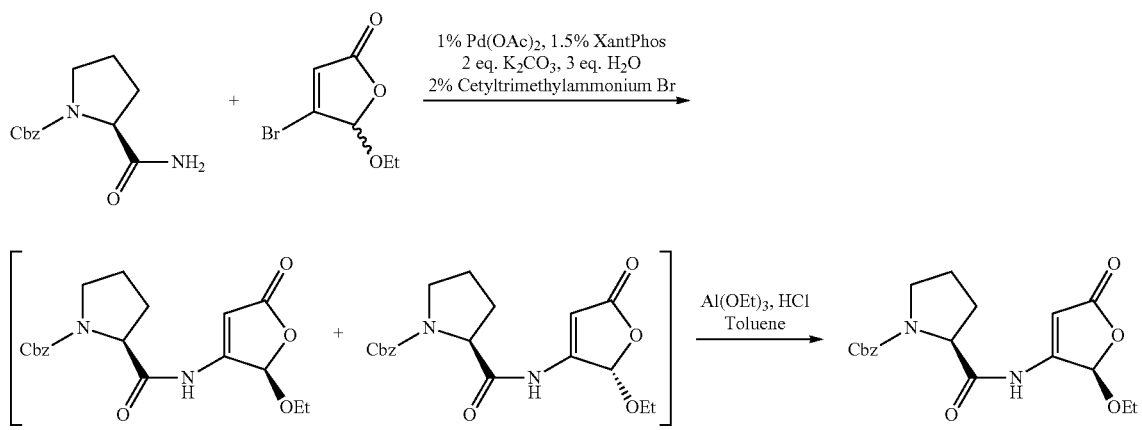

STEP 2:

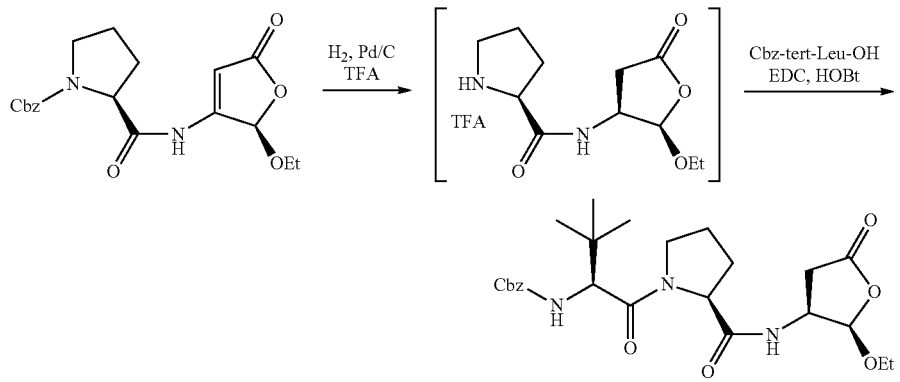

STEP 3:

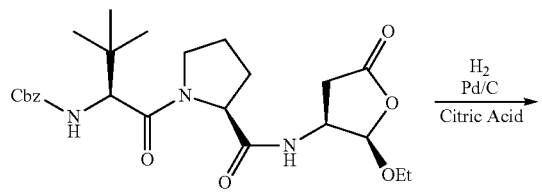

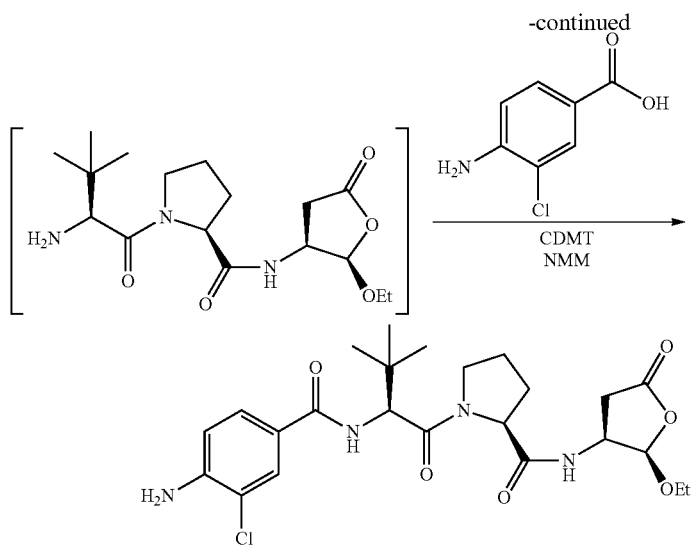

STEP 1:

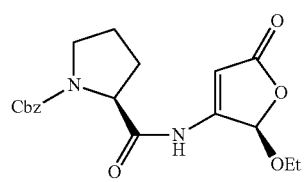

21.7 ml of water was added to a mixture of 100.0 g of CBZ-prolinamide, 0.92 g of Palladium acetate, 3.47 g of Xantphos, 111.2 g of Potassium carbonate and 2.93 g of Cetyltrimethylammonium bromide in Toluene (1000 ml) maintaining the temperature at T=20-25° C. All vessel chargings and additions were performed under nitrogen to avoid/limit oxidation of the Palladium catalyst. The reaction was then warmed to T=50-55° C. and stirred for about 2 hours. Separately, Bromoethoxyfuranone (91.5 g) and toluene (100 ml) were charged into a separate flask and stirred at 20-25° C. until complete dissolution occurred. The Bromoethoxyfuranone solution was then added to the initial reaction mixture over 3-3.5 hours at 50-55° C. and then stirred until the reaction was completed in quantitative yield in about 1 hour. The reaction mixture was filtered at T=50-55° C. and the solids were rinsed with Toluene (500 ml). The filtrate was washed with water (500 ml. The aqueous phase was discarded and the organic phase was concentrated to approximately 500 ml at <50° C. under vacuum. The solution was cooled to 5° C.-10° C. and 9.8 g Aluminum triethoxide were added.

Into a separate flask 11.3 ml Acetyl chloride was added to a solution made of 100 ml Toluene and 9.7 ml Ethanol, maintaining the temperature at T=5-10° C. (in situ generation of anhydrous HCl), then the mixture was stirred at T=5-10° C. for about 1 hour. The Toluene/Ethanol/HCl solution was then added to the previous reaction mixture over 15 minutes at T=5-10° C., then seeded with the product and stirred at T=5-10° C. for 12 hours, at T=20-25° C. for 48 hours, at T=5-10° C. for 12 hours. The product was filtered at T=5-10° C. and washed with 100 ml of Toluene. The wet material was dissolved at 70° C.-75° C.) in 1500 ml Toluene and the solution was filtered at 75° C. through Dicalite (filtration aid agent). The solids were rinsed with 100 ml Toluene. The organic solution was vacuum concentrated to 500 ml. The resultant slurry was cooled to 20-25° C. over 1 hour, stirred for 3-4 hours, filtered and the product rinsed with 100 ml toluene. The product was dried under vacuum at 35-40° C.

Step 2:

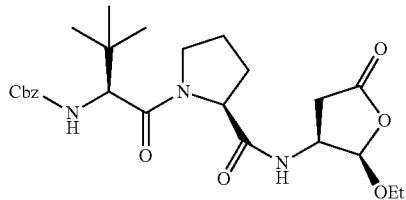

The furanone of Step 1 100 g was charged into a stainless steel (3 it) autoclave together with 20 g of 5% Palladium on charcoal (approx. 50% wet), followed by 800 ml of ethyl acetate and 19.5 ml of trifluoroacetic acid. The autoclave was pressurized with hydrogen (4 bars) and the temperature set at T=20-25° C. The hydrogenolysis was run for 2-3 hrs, periodically repressurizing to 4 bar as hydrogen uptake proceeds, until uptake of hydrogen ceased. The catalyst was filtered off and washed twice with 100 ml of ethyl acetate to give a solution of the deprotected proline compound.

Separately, a solution of sulfuric acid (14.6 ml) in water (330 ml) was added to a mixture of 119.2 g of Cbz-t-leucine dicyclohexylamine salt and 430 ml of Ethyl acetate. The resulting solution was stirred at T=20-25° C. for 30 minutes. The organic layer was separated, washed twice with 500 ml of water and added to 43.3 g of hydroxybenzotriazole. DMF (190 ml) was added to this mixture followed by 56.3 g of EDC which produced a cloudy reaction mixture from the clear yellowish solution. The reaction was stirred at T=20-25° C.

for 30-60 minutes. The solution of deprotected proline compound from the autoclave was charged to the reaction mixture, 81.1 g of Triethylamine was then added dropwise (over 20-30 minutes) and the resulting cloudy mixture was stirred at T=20-25° C. for 1.5-2 hours. 400 ml of water was added and the reaction stirred at 20-25° C. for 12 hours. The organic layer was separated and washed with 400 ml of an aqueous sodium bicarbonate (7.5%) solution and twice with 400 ml of water. These water washings were performed at 45-50° C. The organic phase was concentrated to 400 ml volume at 40-45° C. 300 ml of ethyl acetate were added and the mixture concentrated to 350 ml to remove residual water. The solution was cooled to 20-25° C. and 200 ml of N-heptane added over 1 hour at 20-25° C., and the mixture seeded with the compound shown in Example 3 above and stirred at T=20-25° C. for 1 hour. The resultant slurry was cooled to T=5-10° C. and stirred for an additional hour at the same temperature. 400 ml of N-Heptane were added over 2-3 hours at T=5-10° C., the slurry was filtered and rinsed twice with Ethyl acetate/N-heptane (40 ml, 60 ml respectively). The crystals were dried under vacuum at T=35-40° C. for at least 8 hours.

Step 3:

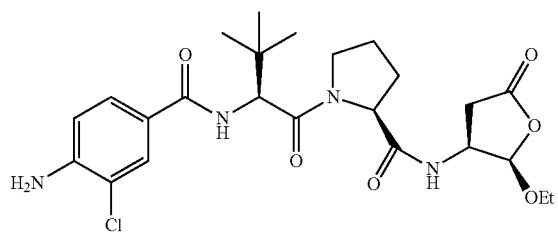

The product of step 2 (100 g), 5% Palladium on charcoal (approx. 50% wet, 20 g) 100 ml of DMF, 600 ml of ethyl acetate and 43.1 g of Citric acid monohydrate were charged into a stainless steel (3 it) autoclave. The stainless steel autoclave was pressurized with hydrogen (4 bar) and the temperature set at −2° to +2° C. The reaction was run for 2-3 hrs periodically repressurizing to 4 bar as hydrogen uptake proceeds. The catalyst was filtered off and washed with a mixture of 85 ml of ethyl acetate and 15 ml of DMF.

Separately, 23.5 g of N-Methylmorpholine is added to a mixture of 33.1 g of 4-Amino-chloro-benzoic acid 34.4 g of 2-Chloro-4,6-dimethoxytriazine (DMT-Cl) in 300 ml of ethyl acetate over 20-30 minutes at ambient temperature for 2-3 hours at 23-27° C. to obtain the DMT active ester of 4-Amino-3-chlorobenzoic acid. The mixture is cooled to 0° to +5° C. and 300 ml of purified water are added to the solution keeping temperature in the same range. The solution of the deprotected t-leucine product as the citrate salt is added at 0° C. to +5° C. over 30-60 minutes, the reaction mixture is then brought to pH 6.5-7.5 by adding 30% sodium hydroxide (approx. amount: 71 ml), and stirred 6-7 hrs at 20° to 25° C. After completion of the reaction, the phases are separated and the organic layer added to sodium bisulfate solution (15 g of sodium bisulfate in 235 ml of water) and stirred for 3 hrs at 20° C. to 25° C. The phases are separated and the organic layer is washed four times with water (150 ml each), twice with sodium bicarbonate solution (total: 20 g of sodium bicarbonate in 400 ml of water), and once with 150 ml of water. To the solution is added 10 g of activated charcoal and 10 g of Dicalite and filtered and the solids washed with 100 ml of ethyl acetate. The filtrate was distilled under vacuum to a volume of 200 ml at <40° C. when the resultant mixture crystallizes. Ethyl acetate (150 ml) was added to a total volume of 350 ml. N-heptane (300 ml) was added over 2 hrs and after stirring the slurry for 3 hrs at 20° to 25°, the solid was filtered, washed with ethyl acetate/N-Heptane (100 ml, 1:1) and dried at 60° C. under vacuum.

All of the documents cited herein are hereby incorporated herein by reference.

While we have described a number of embodiments of this invention, it is apparent that our basic examples may be altered to provide other embodiments which utilize the compounds and methods of this invention. For instance, protecting groups besides CBZ may be used to protect amines in one or more of the synthetic steps described above. Therefore, it will be appreciated that the scope of this invention is to be defined by the appended claims rather than by the specific embodiments which have been represented by way of example.

What is claimed is:

1. A process of producing a compound of

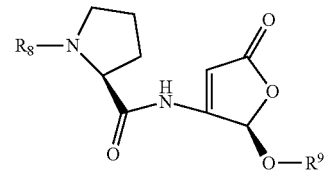

comprising purifying a mixture of

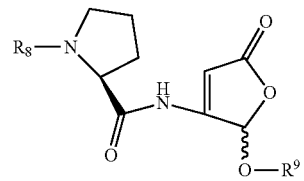

wherein $R^8$ is a protecting group and $R^9$ is $C_1$-$C_5$ alkyl, and purifying includes selectively crystallizing the mixture with an organic solvent, or dynamically crystallizing the mixture wherein:
  selective crystallization comprises combining the mixture and an organic solvent at or above room temperature and warming the combination with stirring to dissolve the mixture and then cooling the combination; and wherein:
  dynamically recrystallizing the mixture comprises contacting the mixture with a Lewis acid and a solvent optionally including a protic acid; wherein:
  the organic solvent is selected from toluene, dioxane, THF, or mixtures thereof;
  the lewis acid is selected from $BF_3$-etherates, metal halides, alkoxides, or mixed halide/alkoxides;
  the mixed halide alkoxides are selected from $Al(Oalkyl)_2Cl$ or $Al(Oalkyl)Cl_2$);
  the alkyl group of the alkyl or alkoxide is a straight or branched chain having one to twelve carbon atoms;
  the metal is aluminum, titanium, zirconium, magnesium, copper, zinc, iron, tin, boron, ytterbium, lanthanum, or samarium; and
  the protic acid is selected from HCl, HBr, triflic acid, sulfuric acid, phosphoric acid, or combinations thereof.

2. The process of claim 1, wherein the step of purifying the mixture comprises selectively crystallizing the mixture with an organic solvent.

3. The process of claim 1, wherein the step of purifying comprises dynamic crystallization which comprises contacting the mixture with a lewis acid and a solvent optionally including a protic acid.

4. The process of claim 3, wherein the step of purifying comprises contacting the mixture with $Al(Oalkyl)_3$ in a solvent including a protic acid.

5. The process of claim 4, wherein the mixture is epimerized with $Al(OEt)_3$ in toluene in the presence of HCl.

6. The process of claim 2, wherein the organic solvent is toluene.

* * * * *